(12) United States Patent
Groves et al.

(10) Patent No.: US 11,242,248 B2
(45) Date of Patent: Feb. 8, 2022

(54) IRON PORPHYRAZINES AS EFFICIENT, CATALYTIC AND SCALABLE METHOD TO PRODUCE CHLORINE DIOXIDE

(71) Applicant: The Trustees of Princeton University, Princeton, NJ (US)

(72) Inventors: John T. Groves, Princeton, NJ (US); Roy Xiao, Princeton, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 322 days.

(21) Appl. No.: 16/400,277

(22) Filed: May 1, 2019

(65) Prior Publication Data

US 2019/0256355 A1    Aug. 22, 2019

Related U.S. Application Data

(63) Continuation of application No. 15/228,629, filed on Aug. 4, 2016, now Pat. No. 10,414,651, which is a continuation-in-part of application No. 13/818,575, filed as application No. PCT/US2011/048396 on Aug. 19, 2011, now Pat. No. 9,527,734.

(Continued)

(51) Int. Cl.
| | | |
|---|---|---|
| C01B 11/02 | (2006.01) |
| B01J 31/22 | (2006.01) |
| B01J 31/26 | (2006.01) |
| D21C 9/14 | (2006.01) |
| C02F 1/76 | (2006.01) |
| A61L 2/18 | (2006.01) |
| C07F 15/02 | (2006.01) |
| C02F 103/02 | (2006.01) |
| B01J 31/18 | (2006.01) |

(52) U.S. Cl.
CPC .............. *C01B 11/024* (2013.01); *A61L 2/18* (2013.01); *B01J 31/2295* (2013.01); *B01J 31/26* (2013.01); *C07F 15/025* (2013.01); *D21C 9/14* (2013.01); *B01J 31/183* (2013.01); *B01J 31/1815* (2013.01); *B01J 2531/025* (2013.01); *B01J 2531/842* (2013.01); *C02F 1/76* (2013.01); *C02F 2103/023* (2013.01); *C02F 2303/04* (2013.01)

(58) Field of Classification Search
CPC ...... C01B 11/024; A61L 2/18; B01J 31/2295; B01J 31/26; C07F 15/025; D21C 9/14; C02F 1/76; C02F 2303/04
USPC .......................................................... 502/62
See application file for complete search history.

(56) References Cited

U.S. PATENT DOCUMENTS

| 2,966,453 A | 12/1960 | Gleim et al. |
| 3,749,672 A | 7/1973 | Golton et al. |

(Continued)

OTHER PUBLICATIONS

Moreira et al., "Iron porphyrins immobilized on silica surface and encapsulated in silica matrix: a comparison of their catalytic activity in hydrocarbon oxidation", Journal of Molecular Catalysis A: Chemical 233 (2005) 73-81. (Year: 2005).*

(Continued)

*Primary Examiner* — Anita Nassiri-Motlagh
(74) *Attorney, Agent, or Firm* — Volpe Koenig

(57) ABSTRACT

Methods, kits, cartridges, and compounds related to generating chlorine dioxide by exposing $ClO_2^-$ to at least one of an iron porphyrin catalyst or an iron porphyrazine catalyst are described.

22 Claims, 12 Drawing Sheets

FeTDMImP

FeTM-2,3-PyPz

Related U.S. Application Data

(60) Provisional application No. 62/200,973, filed on Aug. 4, 2015, provisional application No. 61/376,052, filed on Aug. 23, 2010, provisional application No. 61/504,460, filed on Jul. 5, 2011.

(56) References Cited

U.S. PATENT DOCUMENTS

| | | | |
|---|---|---|---|
| 3,923,645 | A | 12/1975 | Anderson, Jr. et al. |
| 5,306,440 | A | 4/1994 | Ripley et al. |
| 5,346,670 | A | 9/1994 | Renzoni et al. |
| 7,223,332 | B1 | 5/2007 | Tertel |
| 2006/0120928 | A1 | 6/2006 | Annacone |
| 2008/0292534 | A1 | 11/2008 | Richardson et al. |
| 2009/0008238 | A1 | 1/2009 | Williams |
| 2010/0093688 | A1 | 4/2010 | Groves |

OTHER PUBLICATIONS

Greenwood, Norman N.; Earnshaw, A. (1997), Chemistry of the Elements (2nd ed.), Oxford: Butterworth-Heinemann, pp. 844-849, ISBN 0080379419.
Brockway, L.O. (Mar. 1933). "The Three-Electron Bond in Chlorine Dioxide". Proc. Natl. Acad. Sci. U.S.A. 19 (3): 303-7. PMID 16577512.
Thomas Wilson Swaddle (1997). Inorganic chemistry: an industrial and environmental perspective. Academic Press. pp. 198-199. ISBN 0126785503.
Flesch, R.; Plenge, J.; Rühl, E. (2006). "Core-level excitation and fragmentation of chlorine dioxide". International Journal of Mass Spectrometry 249-250: 68-76. doi:10.1016/j.ijms.2005.12.046.
Derby, R. I.; Hutchinson, W. S. "Chlorine(IV) Oxide" Inorganic Syntheses, 1953, IV, 152-158.
Vogt, H.; Balej, J.; Bennett, J. E.; Wintzer, P.; Sheikh, S. A.; Gallone, P.; Vasudevan, S.; Pelin, K. (2010). "Chlorine Oxides and Chlorine Oxygen Acids". Ullmann's Encyclopedia of Industrial Chemistry. Wiley-VCH Verlag GmbH & Co. KGaA. doi:10.1002/14356007. a06_483.pub2.
M. J. Zdilla, A. Q. Lee, M. M. Abu-Omar, Angew. Chem. Int. Ed. 2008, 47, 7697.
M. J. Zdilla, A. Q. Lee, M. M. Abu-Omar, Inorg. Chem. 2009, 48, 2260.
C. Jakopitsch, H. Spalteholz, P. G. Furtmüller, J. Arnhold, C. Obinger, J. Inorg. Biochem. 2008, 102, 293.
Seymour Stanton Block (2001). Disinfection, sterilization, and preservation (5th ed.). Lippincott Williams & Wilkins, p. 215. ISBN 0683307401.
Sorlini, S.; Collivignarelli, C. (2005). "Trihalomethane formation during chemical oxidation with chlorine, chlorine dioxide and ozone of ten Italian natural waters". Desalination 176 (1-3): 103-111. doi:10.1016/j.desal.2004.10.022.
Li J.; Yu Z.; Gao M. (1996). "A pilot study on trihalomethane formation in water treated by chlorine dioxide (translated from Chinese)". Zhonghua Yu Fang Yi Xue Za Zhi (Chinese journal of preventive medicine) 30 (1): 10-13. PMID 8758861 (English Abstract provided).
C. J. Volk; R. Hofmann; C. Chauret; G. A. Gagnon; G. Ranger; R. C. Andrews (2002). "Implementation of chlorine dioxide disinfection: Effects of the treatment change on drinking water quality in a full-scale distribution system". J. Environ. Eng. Sci. 1: 323-330. doi:10.1139/SO2-026. http://pubs.nrc-cnrc.gc.ca/rp/rppdf/s02-026.pdf. Retrieved Nov. 27, 2009.
M. A. Pereira; L. H. Lin; J. M. Lippitt; S. L. Herren (1982). "Trihalomethanes as initiators and promoters of carcinogenesis". Environ Health Perspect 46: 151-156. PMID 7151756.
Andrews, L.; Key, A.; Martin, R.; Grodner, R.; Park, D. (2002). "Chlorine dioxide wash of shrimp and crawfish an alternative to aqueous chlorine". Food Microbiology 19 (4): 261-267. doi:10. 1006/fmic.2002.0493.
Zhe Zhang; Carole McCann; Janet E. Stout; Steve Piesczynski; Robert Hawks; Radisav Vidic; Victor L. Yu (2007). "Safety and Efficacy of Chlorine Dioxide for Legionella control in a Hospital Water System". Infection Control and Hospital Epidemiology 28 (8). http://www.legionella.org/ZhangICHE07.pdf. Retrieved Nov. 27, 2009.
Ogata N, Shibata T (Jan. 2008). "Protective effect of low-concentration chlorine dioxide gas against influenza A virus infection". J. Gen. Virol. 89 (Pt 1): 60-7. doi:10.1099/vir.0.83393-0. PMID 18089729. http://vir.sgmjournals.org/cgi/content/abstract/89/1/60?maxtoshow=&HITS=10&hits=10&RESULTFORMAT=&author1=ogata+n&andorexactfulltext=and&searchid=1&FIRSTINDEX=0&sortspec=relevance&resourcetype=HWCIT.
Zhang, Y. L.; Zheng, S. Y.; Zhi, Q. (2007). "Air Disinfection with Chlorine Dioxide in Saps". Journal of Environment and Health 24 (4): 245-246. http://www.csa.com/partners/viewrecord.php?requester=gs&collection=TRD&recid=07519213EN (English Abstract provided).
"Anthrax spore decontamination using chlorine dioxide". United States Environmental Protection Agency. 2007. http://www.epa.gov/opp00001/factsheets/chemicals/chlorinedioxidefactsheet.htm. Retrieved Nov. 27, 2009.
Sy, Kaye V.; McWatters, Kay H.; Beuchat, Larry R. (2005). "Efficacy of Gaseous Chlorine Dioxide as a Sanitizer for Killing Salmonella, Yeasts, and Molds on Blueberries, Strawberries, and Raspberries". Journal of Food Protection (International Association for Food Protection) 68 (6): 1165-1175. PMID 15954703. http://www.ingentaconnect.com/content/iafp/jfp/2005/00000068/00000006/art00007.
Frascella J.; Gilbert R. D.; Fernandez P.; Hendler J. (2000). "Efficacy of a chlorine dioxide-containing mouthrinse in oral malodor". Compend Contin Educ Dent 21 (3): 241-248. PMID 11199703.
Weitner, T.; Budimir, A.; Kos, I.; Batinic-Haberle, I.; Birus, M. J. Chem. Soc., Dalton Trans. 2010, 39, 11568-11576.
Budimir, A.; Smuc, T.; Weitner, T.; Batinic-Haberle, I.; Birus, M. J. Coord. Chem. 2010, 63, 2750-2765.
Batanic-Haberle, I.; Benov, L.; Spasojevic, I.; Fridovich, I. J. Biol. Chem. 1998, 273, 24521-24528. "The Ortho Effect Makes Manganese (III) Meso-Tetrakis-(N-Methylpyridinium-2-yl) Porphyrin a Powerful and Potentially Useful Superoxide Dismutase Mimic."
Spasojevic, I.; Batinic-Haberle, I.; Inorg. Chim. Acta 2001, 317, 230-242. "Manganese (III) Complexes with Porphyrins and Related Compounds as Catalytic Scavengers of Superoxide."
Amaravathi, M.; Murthy, K.S.K.; Rao, M.K.; Reddy, B.S. Tet. Lett. 2001, 42, 6745-6747. "Synthesis of meso-Tetrakis (imidazol-5-yl) porphyrins."
Milgrom, L.R.; Dempsey, P.J.F.; Yahioglu, G. Tet. Lett. 1996, 52, 9877-9890. "5,10,15,20-Tetrakis(N-protected-imidazol-2-yl) porphyrins."
Sanchez-Migallon, A.; de la Hoz, A.; Begtrup, M.; Fernandez-Castano, C.; Foces-Foces, C.; Elguero, J. Tet. Lett. 1996, 10811-10822. "Porphyrins with Four Azole Substituents in meso Positions. Part 2. X-ray Crystal Structure of meso-tetrkis {1-[2-(trimethylsilyl)ethoxymethyl]pyrazol-5-yl}-porphyrin at 200K."
Wöhrle, D.; Gitzel, J.; Okura, I.; Aono, S. Photoredox Properties of tetra-2,3-pyridinoporphyrazines (29H,31H-tetrapyrido[2,3-b: 2',3'-g: 2",3"-I: 2"',3"'-q]porphyrazine); J. Chem. Soc., Perkin Trans. 2 1985, 1171-8.
S. S. Marla, J. Lee, J. T. Groves, Proc. Nat. Acad. Sci. USA 1997, 94, 14243.
Stuzhin, P. A.; Vagin, S. I.; Hanack, M. Synthesis and Spectral Properties of Bisaxially Coordinated (Octaphenyltetraazaporphyrinato)ruthenium(II) Complexes; Inorg. Chem. 1998, 37, 2655-2662.
Fitzgerald, J. P.; Kaul, B. B.; Yee, G. T. Vanadium [dicyanoperfluorostilbene]2.yTHF: a molecule-based magnet with Tc ≈ 205 K; Chem. Commun. 2000, 49-50.
Anderson, M. E.; Barrett, A. G. M.; Hoffman, B. M. Super-Charged Porphyrazines: Synthesis and Physical Properties of Octacationic Tetraazaporphyrins; Inorg. Chem. 1999, 38, 6143-51.
Reese, C. B.; Zhang, P. Z. Phosphotriester Approach to the Synthesis of Oligonucleotides: A Reappraisal; J. Chem. Soc., Perkin Trans. 1 1993, 2291-301.

(56) References Cited

OTHER PUBLICATIONS

G. Peintler, I. Nagypal, I. R. Epstein, J. Phys. Chem. 1990, 94, 2954.
Alternative Disinfectants and Oxidants Guidance Manual (EPA 815-R-99-014), 1999.
I. Fabian, G. Gordon, Inorg. Chem. 1992, 31, 2144.
J. S. Nicoson, D. W. Margerum, Inorg. Chem. 2002, 41, 342.
D. Lahaye, J. T. Groves, J. Inorg. Biochem. 2007, 101, 1786.
A. Q. Lee, B. R. Streit, M. J. Zdilla, M. M. Abu-Omar, J. L. DuBois, Proc. Nat. Acad. Sci. USA 2008, 105, 15654.
R. G. Kieffer, G. Gordon, Inorg. Chem. 1968, 7, 239.
N. Jin, M. Ibrahim, T. G. Spiro, J. T. Groves, J. Am. Chem. Soc. 2007, 129, 12416.
R. H. Holm, J. P. Donahue, Polyhedron 1993, 12, 571.
H. A. Laitinen, K. W. Boyer, Anal. Chem. 1972, 44, 920.
N. Jin, J. T. Groves, J. Am. Chem. Soc. 1999, 121, 2923.
J. T. Groves, J. B. Lee, S. S. Marla, J. Am. Chem. Soc. 1997, 119, 6269.
Sampling and Analytical Methods: Chlorine and Chlorine Dioxide in Workplace Atmospheres (OSHA method 126SGX), United States Department of Labor, 2008.
J. T. Groves, S. S. Marla, J. Am. Chem. Soc. 1995, 117, 9578.
L. M. Slaughter, J. P. Collman, T. A. Eberspacher, J. I. Brauman, Inorg. Chem. 2004, 43, 5198.
S. Shahangian, L. P. Hager, J. Biol. Chem. 1981, 256, 6034.
N. Jin, J. L. Bourassa, S. C. Tizio, J. T. Groves, Angew. Chem. Int. Ed. 2000, 39, 3849.
Meunier al al., "Mechanism of Oxidation Reactions Catalyzed by Cytochrome P450 Enzymes," Chem. Rev. 2004, 104, 3947-3980.
Gustafsson et al., "Sodium Periodate, Sodium Chlorite, and Organic Hydroperoxides as Hydroxylating Agents in Steroid Hydroxylation Reactions Catalyzed by Adrenocortical Microsomal and Mitochondrial Cytochome P450," Archives of Biochemistry and Biophysics 174, 440-453 (1976).
Sun et al., "A dominate homolytic O—Cl bond cleavage with low-spin triple-state Fe(IV)=O formed is revealed in the mechanism of heme-dependent chlorite dismutase," Dalton Trans. 2014, 43, 973-981, The Royal Society of Chemistry 2014.

\* cited by examiner

FeTM-2,3-PyPz

FeTDMImP

Scheme 4

Reagents and conditions: i, 1:1 Et$_2$O-MeOH, I$_2$, NaOMe, reflux; ii, Mg(O-nBu), n-BuOH, reflux; iii, dilute aqueous HCl; iv, MeOTs, DMF, 3 days, 100 °C; MCl$_2$, 2.0 M NaCl, H$_2$O Scheme 5

Reagents and conditions: i, paraformaldehyde, 160 °C; ii, SOCl$_2$, reflux; iii, NaCN, DMSO

IRON PORPHYRAZINES AS EFFICIENT, CATALYTIC AND SCALABLE METHOD TO PRODUCE CHLORINE DIOXIDE

CROSS REFERENCE TO RELATED APPLICATIONS

This application is a continuation of U.S. patent application Ser. No. 15/228,629, which was filed Aug. 4, 2016 and claimed the benefit of U.S. Provisional Patent Application No. 62/200,973, which was filed Aug. 4, 2015. This application is also a continuation-in-part of U.S. application Ser. No. 13/818,575, which was filed May 3, 2013, issued as U.S. Pat. No. 9,527,734 on Dec. 27, 2016, and was a 35 USC § 371 national stage application of PCT/US2011/048396, which was filed Aug. 19, 2011, and claimed the benefit of U.S. Provisional Patent Application No. 61/376,052, filed Aug. 23, 2010, and U.S. Provisional Patent Application No. 61/504,460, filed Jul. 5, 2011, all of which are incorporated herein by reference as if fully set forth.

This invention was made with government support under Grant CHE-1148597 awarded by the National Science Foundation. The government has certain rights in the invention.

FIELD

The disclosure herein relates to the preparation of chlorine dioxide.

BACKGROUND

Chlorine dioxide may be used in a variety of settings, including the following. Chlorine dioxide is used primarily (>95%) for bleaching of wood pulp, but is also used for the bleaching of flour and for the disinfection of municipal drinking water. The Niagara Falls, N.Y. water treatment plant first used chlorine dioxide for drinking water treatment in 1944 for phenol destruction. Chlorine dioxide was introduced as a drinking water disinfectant on a large scale in 1956, when Brussels, Belgium changed from chlorine to chlorine dioxide. Its most common use in water treatment is as a pre-oxidant prior to chlorination of drinking water to destroy natural water impurities that produce trihalomethanes on exposure to free chlorine. Trihalomethanes are suspect carcinogenic disinfection byproducts associated with chlorination of naturally occurring organics in the raw water. Chlorine dioxide is also superior to chlorine when operating above pH 7, in the presence of ammonia and amines and/or for the control of biofilms in water distribution systems. Chlorine dioxide is used in many industrial water treatment applications as a biocide including cooling towers, water processing and food processing. Chlorine dioxide is less corrosive than chlorine and superior for the control of *legionella* bacteria.

Chlorine dioxide is more effective as a disinfectant than chlorine in most circumstances against water borne pathogenic microbes such as viruses, bacteria and protozoa—including cysts of *Giardia* and the oocysts of *Cryptosporidium*. The use of chlorine dioxide in water treatment leads to the formation of the by-product chlorite which is currently limited to maximum of 1 ppm in drinking water in the U.S.A. This EPA standard limits the use of chlorine dioxide in the USA to relatively high quality water or water which is to the treated with iron based coagulants (iron can reduce chlorite to chloride).

Chlorine dioxide can also be used for air disinfection, and was the principal agent used for decontamination of buildings in the United States after the 2001 anthrax attacks. After the disaster of Hurricane Katrina in New Orleans, La. and the surrounding Gulf Coast, chlorine dioxide was used to eradicate dangerous mold from houses inundated by water from massive flooding. Chlorine dioxide is used as an oxidant for phenol destruction in waste water streams, control of zebra and quagga mussels in water intakes and for odor control in the air scrubbers of animal byproduct (rendering plants). Stabilized chlorine dioxide can also be used in an oral rinse to treat oral disease and malodor.

The industrial preparation of chlorine dioxide is energy-intensive and fraught with health and safety issues. Furthermore, due to the instability of $ClO_2$ at high pressures, the gas is often generated where it is to be used. Large-scale production of $ClO_2$ may involve the use of such reagents as concentrated strong acids and/or externally-added oxidants (such as $Cl_2$, $H_2O_2$, or hypochlorite). Electrochemical methods can directly oxidize $ClO_2^-$ to $ClO_2$ by a 1-electron process but require considerable input of electrical energy and may not be applicable in rural or underdeveloped areas of the world. An iron-catalyzed decomposition of $ClO_2^-$ has been shown to afford $ClO_2$ (in part), but only under very acidic conditions. Since $ClO_2$ is often generated where it is to be used, these hazardous and/or costly methods must be implemented in facilities that are primarily engineered for other purposes.

SUMMARY

In an aspect, the invention relates to a method of generating chlorine dioxide, $ClO_2$, comprising exposing $ClO_2^-$ to at least one of an iron poyrphyrin catalyst or an iron porphyrazine catalyst. The chlorite may be in the form of salts of the chlorite ion. In an aspect, the invention relates to contacting the catalyst with sodium chlorite under vacuum or with a sparging gas such as air, nitrogen or carbon dioxide, to efficiently draw off the volatile $ClO_2$.

In an aspect, the invention relates to a kit for generating chlorine dioxide comprising at least one of an iron porphyrin catalyst or an iron porphyazine catalyst. The kit may also include a source of $ClO_2^-$ (chlorite ion). The kit may be used to generate chlorine dioxide. The kit may be used to treat a substance. The substance may be but is not limited to water. The kit may also include instructions to combine the at least one of an iron porphyrin catalyst or an iron porphyrazine catalyst with $ClO_2^-$. The kit may also include at least one of a manganese porphyrin catalyst or a manganese porphyrazine catalyst.

In an aspect, the invention relates to a cartridge. The cartridge may include a housing and at least one of a manganes porphyrin catalyst, an iron porphyrin catalyst, a manganese porphyrazine catalyst, or an iron porphyrazine catalyst in the housing. The cartridge may also include a source of $ClO_2^-$. The cartridge may be used to generate chlorine dioxide. The cartridge may be used to treat a substance. The substance may be but is not limited to water.

In an aspect, the invention relates to a kit for generating chlorine dioxide comprising a source of $ClO_2^-$. The kit may also include at least one of a manganese porphyrin catalyst, an iron porphyrin catalyst, a manganese porphyrazine catalyst, or an iron porphyrazine catalyst. The kit may be used to generate chlorine dioxide. The kit may be used to treat a substance. The substance may be but is not limited to water.

In an aspect, the invention relates to a cartridge comprising a housing and a source of $ClO_2^-$. The cartridge may also include at least one of a manganese porphyrin catalyst, an iron porphyrin catalyst, a manganese porphyrazine catalyst, or an iron porphyrazine catalyst. The cartridge may be used to generate chlorine dioxide. The cartridge may be used to treat a substance. The substance may be but is not limited to water.

In an aspect, the invention relates to a method of treating a substance. The method comprises generating chlorine dioxide by exposing $ClO_2^-$ to at least one of an iron porphyrin catalyst or an iron porphyrazine catalyst and exposing the substance to the chlorine dioxide.

In an aspect, the invention relates to a composition comprising an iron porphyrazine compound having a structure of formula VI:

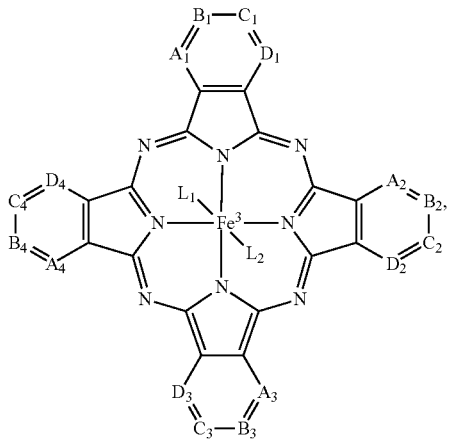

Formula VI wherein, a is the oxidation state II, III or IV of the Mn and each of $A_1$, $A_2$, $A_3$, $A_4$, $B_1$, $B_2$, $B_3$, $B_4$, $C_1$, $C_2$, $C_3$, $C_4$, $D_1$, $D_2$, $D_3$ and $D_4$ are independently selected from $N^+$—$R_n$, N, C—H, C—X, and C—$R_n$. When $N^+$—$R_n$ is selected, only one in each set of $A_1$, $B_1$, $C_1$, and $D_1$; $A_2$, $B_2$, $C_2$, and $D_2$; $A_3$, $B_3$, $C_3$, and $D_3$; or $A_4$, $B_4$, $C_4$, and $D_4$ is $N^+$—$R_n$. When N is selected, only one in each set of $A_1$, $B_1$, $C_1$, and $D_1$; $A_2$, $B_2$, $C_2$, and $D_2$; $A_3$, $B_3$, $C_3$, and $D_3$; or $A_4$, $B_4$, $C_4$, and $D_4$ is N. Each $R_n$ is independently selected from the group consisting of H; methyl; ethyl; propyl; isopropyl; n-butyl; sec-butyl; isobutyl; $CH_2$—$(CH_2)_{n1}$—$CH_3$ where n1=5-20; $CH_2$—$(CH_2)_{n2}$—$CH_2$—X where n2=0-20; $CH_2(CO)$—$(CH_2)_{n3}$—$CH_2$—X where n3=0-20; $CH_2$—Ar—X; $(CH_2)_n$—X; $(CH_2)_m$Ar—X; $(CH_2)_m$Ar—Y; $(CH_2)_n$—Y; $CH_2CONH$—Y; $CH_2COO$—Y; $CH_2CO$—Y; $CH_2CO(CH_2)_p$—Y; $(OCH_2CH_2)_m$—Y; $(OCH_2CH_2)_m$—X; $Y_2$—X; $CH_2CH_2OCH_2CH_2OCH_2CH_2OCH_3$; $CH_2CO_2CH_2CH_3$; $CH_2CH_2OCH_3$; $CH_2CH_2OCH_2CH_2OCH_3$; $(CH_2)_n$—Y; $(CH_2)_n$Ar—X; $(CH_2)_n$Ar—Y; and $Y_2C(Z_1)_3$. $Z_1$ is $CH_2OCH_2(CH_2)_n$X, $CH_2OCH_2(CH_2)_n$Y, or $(CH_2)_nC(O)Y_2C(Z_2)_3$. $Z_2$ is $CH_2OCH_2CH_2C(O)Y_2C(Z_3)_3$. $Z_3$ is $CH_2OCH_2CH_2X$ or $(CH_2)_nC(O)$—$Y_2$—$C(Z_4)_3$. $Z_4$ is $CH_2OCH_2CH_2C(O)Y_2C(Z_5)_3$. $Z_5$ is $CH_2OCH_2CH_2C(O)O(CH_2CH_2O)_mCH_2CH_2O^-$, $(CH_2)_nOCH_2C(CH_2OH)_3$, $(CH_2)_nOCH_2CH(CH_2OH)_2$, $(CH_2)_nOCH_2C(CH_2OH)_2(CH_3)$, $(CH_2)_nOCH_2C[CH_2OCH_2C(CH_2OH)_3]_3$, $(CH_2)_nOCH_2C[CH_2OCH_2C(CH_2O[CH_2CH_2O]_mCH_2CH_2OX)_3$, $CH_2CONH$—Y, $CH_2CO$—Y, or $CH_2CO(CH_2)_p$—Y. Ar is substituted or unsubstituted phenyl, substituted or unsubstituted biphenyl, or substituted or unsubstituted naphthyl and when Ar is the phenyl in —$CH_2$—Ar—X, $(CH_2)_m$Ar—X, or $(CH_2)_m$Ar—Y, the X or Y is attached ortho-meta- or para to the —$CH_2$— attached to pyridoporphyrazine. n is 1 to 10; m is 1 to 200; p is 1 or 2; X is COOH, $COO(alkyl_1)$, $CONH_2$, $CONH(alkyl_1)$, $CON(alkyl_1)_2$, $CO(CH_2)_palkyl_1$, $OPO_3H_2$, $PO_3H_2$, $SO_3H$, $NH_2$, $N(alkyl_1)_2$, or $N(alkyl_1)_3^+$. $alkyl_1$ is methyl, ethyl, propyl, butyl, pentyl, hexyl, heptyl, or octyl; Y is OH, (O—$CH_2CH_2)_m$—$W_1$ or $(CH_2CH_2)_m$—$W_2$. $W_1$ is OH or (O—$(CH_2CH_2)_m$OH). $W_2$ is O-alkyl; and $Y_2$ is —$(CH_2)_n$O—, —$(CH_2)_n$NH—, —$(CH_2)_n$S—; $CH_2CONH$—, $CH_2COO$—, or $CH_2CO(CH_2)_p$—. $L_1$ and $L_2$ are independently absent, halide, oxo, aquo, hydroxo, CN, $OPO_3H$, or alcohol.

BRIEF DESCRIPTION OF THE DRAWINGS

The following detailed description of the preferred embodiments of the present invention will be better understood when read in conjunction with the appended drawings. For the purpose of illustrating the invention, there are shown in the drawings embodiments which are presently preferred. It is understood, however, that the invention is not limited to the precise arrangements and instrumentalities shown. In the drawings.

DETAILED DESCRIPTION

Figure 1B:
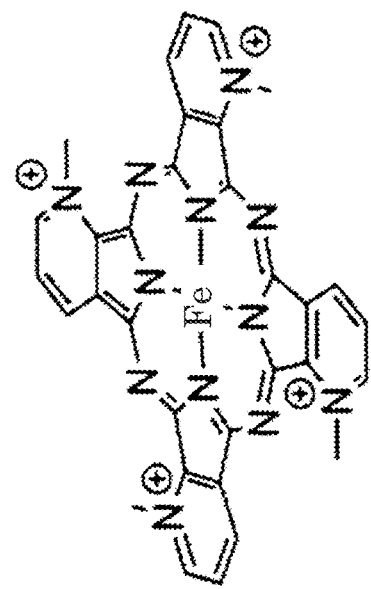
FIG. 1B illustrates the structure of FeTM-2,3-PyPz. Axial ligands may water and hydroxo or halide ion under exemplary conditions.

Certain terminology is used in the following description for convenience only and is not limiting. The words "a" and "one," as used in the claims and in the corresponding portions of the specification, are defined as including one or more of the referenced item unless specifically stated otherwise. This terminology includes the words above specifically mentioned, derivatives thereof, and words of similar import. The phrase "at least one" followed by a list of two or more items, such as "A, B, or C," means any individual one of A, B, or C as well as any combination thereof.

An embodiment includes a process of contacting a chlorite salt in a solvent such as water containing a catalytic amount of particular iron N-alkylpyrido-porphyrazine or pyrido-porphyrazine catalysts. Chlorine dioxide is produced efficiently in minutes at ambient temperature and pressure under mildly acidic conditions. In an embodiment, the catalyst can be immobilized on a readily available clay. This allows facile recovery of the catalyst and would allow the construction of a flow system for continuous production of chlorine dioxide without electricity or other power sources.

An embodiment provides a method of generating chlorine dioxide from chlorite ion by exposing chlorite ion to at least one of an iron porphyrin catalyst or iron porphyrazine catalyst. The catalyst may be water soluble. A mixture of iron porphyrin catalysts or iron porphyrazine catalysts may be present in a method herein. A mixture may be two or more species of iron porphyrin catalysts, two or more species of iron porphyrazine catalysts, or at least one species of iron porphyrin catalyst plus at least one species of iron porphyrazine catalyst. The species of iron porphyrin catalyst may be selected from any iron porphyrin compound herein. The species of iron porphyrazine compound may be selected from any iron porphyrazine compound herein. An embodiment provides a cartridge that may be implemented as a chlorine dioxide generator. An embodiment provides reagents for generating chlorine dioxide. An embodiment provides a new chemical process that allows the effective production of the disinfectant chlorine dioxide from common chlorite salts. An embodiment provides a method, apparatus and/or reagents to produce chlorine dioxide in rural areas that do not have modern facilities. An embodiment includes a process and new catalytic system that is able to produce gaseous chlorine dioxide on demand from easily transportable chlorite salts. A method herein includes contacting a chlorite salt in a solvent such as water containing a catalytic amount of an iron porphyrin or iron porphyrazine catalyst. Chlorine dioxide is produced efficiently in minutes at ambient temperature and pressure under mild, non-acidic or mildly acidic conditions (pH 2-8). The catalyst may be free in solution. The catalyst can be immobilized on a solid support, which may be readily available clay. This may allow facile recovery of the catalyst and the construction of a flow system for continuous production of chlorine dioxide without electricity or other power sources. Embodiments include treating a substance with the $ClO_2$ generated by any embodiment of generating $ClO_2$ herein. The substance may be but is not limited to a coolant, a liquid, water, air, a solid, or a surface. For example, coolant for use in or in a coolant tower may be exposed to $ClO_2$ generated by another embodiment herein.

Compared to manganese catalysts, iron catalysts may be much cheaper, easier to synthesize in large amounts and they may be 100 times more active than manganese counterparts. Preliminary cost analysis indicates that scaling up would be cost effective and may be cheaper than methods now in use.

Embodiments herein include embodiments of U.S. Patent Application Publication No. 2013/0209573 (EFFICIENT, CATALYTIC AND SCALABLE METHOD TO PRODUCE CHLORINE DIOXIDE, a publication of U.S. patent application Ser. No. 13/818,575, a 35 USC § 371 national stage application of PCT/US2011/048396 filed Aug. 19, 2011), which this application claims priority to and is incorporated herein by reference as if fully set forth, but modified by replacement of or addition to a manganese porphyrin catalyst and/or a manganese porphyrazine catalyst therein with at least one of an iron porphyrin or iron porphyrazine catalyst. The iron porphyrin or iron porphyrazine catalyst may be any herein or in U.S. Patent Application Publication No. 2013/0209573. The iron porphyrin or iron porphyrazine catalyst may be or be an iron analog of those in U.S. Pat. No. 8,334,377 (issued Dec. 18, 2012 from U.S. application Ser. No. 12/311,639, which was a 35 USC 371 national phase application of PCT/US2007/021453, filed Oct. 5, 2007), which is incorporated herein by reference as if fully set forth. The iron porphyrin or iron porphyrazine catalyst may be or be an iron analog of those in U.S. Pat. No. 6,448,239 (issued Sep. 10, 2002 from U.S. application Ser. No. 09/587,382, filed Jun. 1, 2000) or U.S. Pat. No. 6,969,707 (issued Nov. 29, 2005 from U.S. application Ser. No. 10/207,323, filed Jul. 29, 2002), which are incorporated herein by reference as if fully set forth. Iron may replace the metal in a catalyst in any of the foregoing documents to arrive at an iron catalyst herein.

In an embodiment, a unique feature of an iron porphyrin catalyzed or iron porphyrazine catalyzed method for the production of chlorine dioxide is that added oxidants such as hydrogen peroxide or chlorine are not necessary. Added reducing agents such as methanol or hydrogen peroxide or added acids such as sulfuric acid or hydrochloric acid are also unnecessary in an embodiment. This is due to the fact that the catalyst is able to utilize oxidation equivalents derived from the chlorite salt itself at a range of pH that is either neutral, mildly acidic, or mildly basic. The net result for the reaction is a significant simplification of the process since complicated metering or potentially hazardous mixtures of hydrogen peroxide and either chlorate or chlorite salts are unnecessary.

Figure 1A:
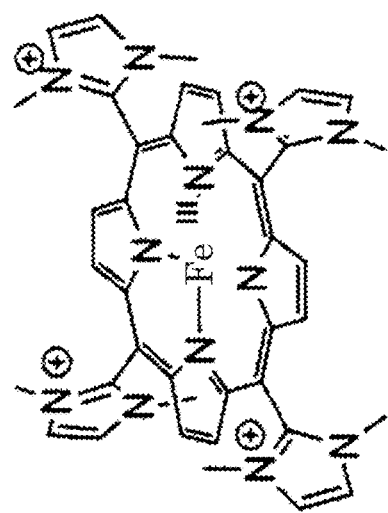
FIG. 1A illustrates the structure of FeTDMImP.

Advances in chemical catalysis have numerous intrinsic advantages among the various strategies for mitigating pollution and workforce hazards in chemical practice. Methods herein provide an efficient, catalytic process for the generation of $ClO_2$ from chlorite ion ($ClO_2^-$). A method herein may include an iron porphyrin catalyst. A method herein may include an iron porphyrazine catalyst. The catalyst may be the water-soluble iron porphyrin tetrakis-5,10,15,20-(N,N-dimethylimidazolium) porphyrinatoiron(III), FeTDMImP (FIG. 1A). The catalyst may be Fe TM-2,3-PyPz (FIG. 1B). The reaction may proceed rapidly and efficiently under mild, ambient conditions.

Embodiments herein offer a potentially greener alternative to the other commonly employed routes of $ClO_2$ preparation. The reactions available can be carried out in an aqueous system at near-neutral or mildly acidic pH under ambient pressure and temperature. In an embodiment, a method of generating $ClO_2$ and optionally of treating a substance with the generated $ClO_2$ includes FeTDMImP-catalyzed decomposition of $ClO_2^-$ (10 mM) at pH 6.8 with 0.1 mol %. Under these conditions, $ClO_2$ may be formed within seconds, and the reaction may be complete within minutes. In an embodiment, a method of generating $ClO_2$ and optionally of treating a substance with the generated $ClO_2$ includes the catalyst FeTM23PyPz (9 mM sodium chlorite, 10 uM FeTM23PyPz, pH 4.7 in 100 mM acetate buffer). Other reaction conditions may be provided in a method herein.

An iron porphyrin catalyst or an iron porphyrazine catalyst may be present in a method, kit or cartridge herein at any concentration from 0.05% to 1% by weight chlorite where %=[(weight catalyst)/(weight chlorite)]×100. An iron porphyrin catalyst or an iron porphyrazine catalyst may be present at any concentration in a sub-range within 0.05% to 1% by weight chlorite. The lower value in the sub-range may be any value from 0.05% to 0.99% in 0.01% increments. The higher value in the sub-range may be any value from 0.01% greater than the lower value to any value up to and including 1% in 0.01% increments. A sub-range may be 0.1% to 0.5% by weight chlorite. When a mixture of iron porphyrin catalysts or iron porphyrazine catalyst is present the "weight catalyst" may be calculated as the combined weight of the catalysts in the mixture. Catalyst concentrations outside of these ranges may be provided in a method, kit or cartridge herein.

An iron porphyrin catalyst or an iron porphyrazine catalyst may be present in a method, kit or cartridge herein at any concentration from 1 to 500 micromolar. The concentration may be any one integer value selected from the range 1 to 500 micromolar. An iron porphyrin catalyst or an iron porphyrazine catalyst may be present at concentration in a sub-range within 1 to 500 micromolar. The lower value in the sub-range may be any value from 1 micromolar to 499 micromolar in 1 micromolar increments. The higher value in the sub-range may be any value from 1 micromolar greater than the lower value to any value up to and including 500 micromolar in 1 micromolar increments. A sub-range may be 5-50 micromolar. When a mixture of manganese porphyrin catalysts or manganese porphyrazine catalyst is present, the concentration may be calculated based on the total amount of catalyst present. Catalyst concentrations outside of these ranges may be provided in a method, kit or cartridge herein.

As described below, an iron porphyrin catalyst or an iron porphyrazine catalyst may be provided on a solid support. An iron porphyrin catalyst or an iron porphyrazine catalyst may be provided in a method, cartridge or kit herein at a concentration of 0.1% to 5% catalyst by weight solid support where %=[(weight catalyst)/(weight of the solid support)]×100. An iron porphyrin catalyst or an iron porphyrazine catalyst may be present at any concentration in a sub-range within 0.1% to 5% by weight solid support. The lower value in the sub-range may be any value from 0.1% to 4.9% in 0.1% increments. The higher value in the sub-range may be any value from 0.1% greater than the lower value to any value up to and including 5% in 0.1% increments. A sub-range may be 0.1% to 1% by weight solid support. When a mixture of iron porphyrin catalysts or iron porphyrazine catalyst is present the "weight catalyst" may be calculated as the combined weight of the catalysts in the mixture. Catalyst concentrations outside of these ranges may be provided in a method, kit or cartridge herein.

The chlorite concentration in a method, kit or cartridge herein may be at any concentration from 0.5 millimolar to 1 molar. The chlorite concentration may be any value in a sub-range from 0.5 millimolar to 1 molar. The lower value of the sub-range may be any value from 0.5 to 999.5 millimolar in 0.5 millimolar increments. The higher value in the sub-range may be any value from 1 millimolar greater than the lower value to 1 molar in 0.5 millimolar increments. A sub-range may be 1-500 millimolar. Chlorite concentrations outside of these ranges may be provided in a method, kit or cartridge herein.

A method herein may include reaction conditions at a pH of 1-14, or any value therein. The pH may be 2 to 8. The pH may be 4.5 to 7.2. The pH may be at a value in a range selected from any two integer values selected from 1, 2, 3, 4, 5, 6, 7, 8, 9, 10, 11, 12, 13, and 14. A kit or cartridge herein may include reagents or conditions such that a reaction utilizing the kit or cartridge has any of the above pH values. A method herein may be conducted at any temperature allowing the reaction to proceed. The temperature may be from the freezing point to the boiling point of the mixture. The temperature may be from 0° C. to 100° C. The temperature may be any integer value from 0° C. to 100° C. The temperature may be any value in a sub-range between any two integer values from 0° C. to 100° C.

Additives may be provided in a method, kit or cartridge herein. Additives that may be provided include but are not limited to acetate or phosphate or bicarbonate or citrate buffer, and sodium chloride to maintain ionic strength. Other additives to buffer or provide ionic strength may also be provided. The acetate or phosphate buffer may be at any concentration from 10 millimolar to 500 millimolar, or at any value in a sub-range between any two integer values from 10 millimolar to 500 millimolar. The sodium chloride may be at any concentration from 10 millimolar to 600 millimolar, or at any value in a sub-range between any two integer values from 10 millimolar to 600 millimolar. Additive concentrations may be provided outside of these ranges.

An iron porphyrin or iron porphyrazine catalyzed method for the production of chlorine dioxide described here may also produce bromine if sodium or potassium bromide, or some similar bromide salt, is present as an additive. Bromide ion can intercept and react with both reactive chlorine species such as hypochlorite or chlorine dioxide and reactive manganese-oxo complexes derived from the catalyst to produce bromine. Bromine is similar in effectiveness to chlorine as a disinfectant and may have advantages in the presence of chlorine dioxide or if all of the chlorine dioxide is subsequently converted to bromine. Methods herein include providing bromide ion in addition to chlorite ion and at least one of an iron porphyrin catalyst or manganese porphyrazine catalyst. A kit or cartridge herein may also be adapted to include bromide and be used to produce bromine. The bromide concentration in a method, kit or cartridge herein may be at any concentration from 0.5 millimolar to 2 molar. The bromide concentration may be any value in a sub-range from 0.5 millimolar to 2 molar. The lower value of the sub-range may be any value from 0.5 to 1999.5 millimolar in 0.5 millimolar increments. The higher value in the sub-range may be any value from 1 millimolar greater than the lower value to 2 molar in 1 millimolar increments. A sub-range may be 1 to 500 millimolar, or 1 to 1000 millimolar. Bromide concentrations outside of these ranges may be provided in a method, kit, or cartridge herein.

A composition may be provided having any one or more catalyst herein and any one or more of the constituents above. The concentration of catalyst and the any one or more constituent above may be but are not limited to those listed above.

In addition, the use of an iron porphyrin or iron porphyrazine as a catalyst may avoid the necessity of auxiliary oxidizers or acids, since the reaction may be self-initiating. A method herein may include removing $ClO_2$ gas produced from a reaction herein. The $ClO_2$ may be removed from a reaction vessel, e.g., by using a simple apparatus. For example, gaseous $ClO_2$ may be removed from the reaction mixture by sparging with nitrogen, helium, carbon dioxide or air. In the case of carbon dioxide, reaction with water to produce bicarbonate and protons has a benefit of maintaining a mildly acidic pH. The sparging tube and optionally a frit may be placed at the bottom of the reaction mixture and the $ClO_2$ may be trapped in cold water. The removed $ClO_2$ may be used to oxidize a substrate. The yield may be almost 60%. An efficiently-engineered generator could take full advantage of the oxidizing power of the $ClO_2$. A heterogeneous version of this process would adapt well to flow or cartridge systems for water purification and would facilitate removal and recycling of the catalyst. Embodiments provide such systems.

Porphyrin catalysts are discussed in U.S. application Ser. No. 12/311,639, which was a 35 USC 371 national phase application of PCT/US2007/021453 filed Oct. 5, 2007 and is incorporated herein by reference as if fully set forth. Porphyrin catalysts are also discussed in U.S. Pat. Nos. 6,448,239 and 6,969,707, which are incorporated herein by reference as if fully set forth. The embodiments described herein extend the knowledge of porphyrin catalysts and methods of use thereof. One or more of the porphyrin catalysts in U.S. patent application Ser. No. 12/311,639 or U.S. Pat. Nos. 6,448,239 and 6,969,707 may be utilized in an embodiment herein. Iron may replace the metal in a catalyst in any of the foregoing documents to arrive at an iron catalyst herein.

An iron porphyrin catalyst for any embodiment herein may have a structure of formula I:

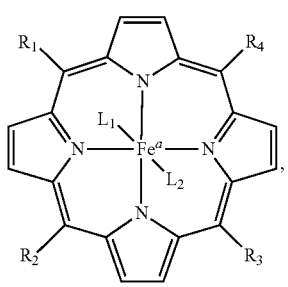

Formula I $R_1$, $R_2$, $R_3$ and $R_4$ may be independently selected from the group consisting of TM2PyP, TM4PyP, TDMImP, and TDMBImp, which have a structure of formulas II, III, IV and V, respectively:

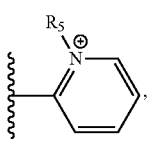

Formula II

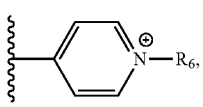

Formula III

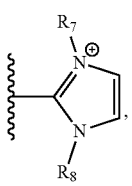

Formula IV

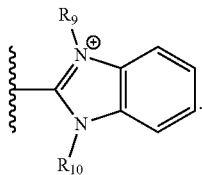

Formula V

Examples of $R_5$, $R_6$, $R_7$, $R_8$, $R_9$, and $R_{10}$ are provided below. $R_1$, $R_2$, $R_3$, and $R_4$ may be independently selected from any substituent such that the resulting porphyrin has catalytic activity for the production of chlorine dioxide from chlorite. $R_5$, $R_6$, $R_7$, $R_8$, $R_9$, and $R_{10}$ may be independently selected from any substituent such that the resulting porphyrin has catalytic activity for the production of chlorine dioxide from chlorite. Acronyms: TM2PyP, tetra-(N-methyl)-2-pyridyl porphyrin; TM4PyP, tetra(N-methyl)-4-pyridyl porphyrin; TDMImP, tetra-(N,N-dimethyl)-imidazolium porphyrin; TDMBImP, tetra(N,N-dimethyl)-benzimidazolium porphyrin; The superscripted "a" represents oxidation state of the Fe. The oxidation state may be any possible oxidation state. The oxidation state may be II, III or IV in non-limiting examples; axial ligands are represented by $L_1$ and $L_2$. Both Ls may be absent, or the complexes may be either 5-coordinate with one L ligand or 6-coordinate with two L ligands. The complexes may have charge balancing counter anions. A non-limiting example of a charge balancing counter anion is chloride ion. Further non-limiting examples of charge balancing counter anions are provided below.

A manganes porphyrazine catalyst for any embodiment herein may have a structure of formula VI:

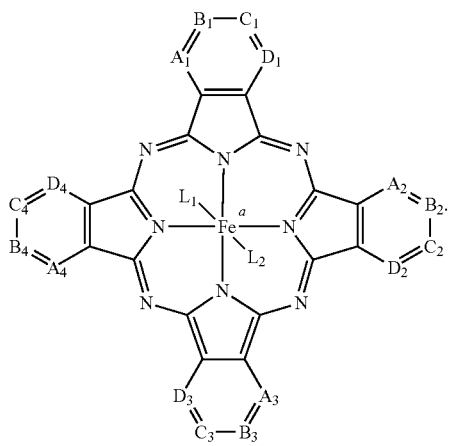

Formula VI

One or zero of $A_1$, $B_1$, $C_1$, and $D_1$ may be $N^+$—$R_n$ where the $N^+$ occupies the position of $A_1$, $B_1$, $C_1$, or $D_1$. One or zero of $A_2$, $B_2$, $C_2$, and $D_1$ may be $N^+$—$R_n$ where the $N^+$ occupies the position of $A_2$, $B_2$, $C_2$, or $D_2$. One or zero of $A_3$, $B_3$, $C_3$, and $D_3$ may be $N^+$—$R_n$ where the $N^+$ occupies the position of $A_3$, $B_3$, $C_3$, or $D_3$. One or zero of $A_4$, $B_4$, $C_4$, and $D_4$ may be $N^+$—$R_n$ where the $N^+$ occupies the position of $A_4$, $B_4$, $C_4$, or $D_4$. One or zero of $A_1$, $B_1$, $C_1$, and $D_1$ may be N. One or zero of $A_2$, $B_2$, $C_2$, and $D_2$ may be N. One or zero of $A_3$, $B_3$, $C_3$, and $D_3$ may be N. One or zero of $A_4$, $B_4$, $C_4$, and $D_4$ may be N. Each of the remaining $A_i$-$D_i$ may be independently selected from C—H, C—X, and C—$R_n$ where i is 1, 2, 3, or 4 and the C occupies the position of $A_i$, $B_i$, $C_i$ or $D_i$. X is as defined below with respect to $R_5$, $R_6$, $R_7$, $R_8$, $R_9$, and $R_{10}$, or $R_{11}$, $R_{12}$, $R_{13}$, and $R_{14}$. $R_n$ may be any one of R11-R14 as described below. Each $R_n$ may be independently selected from any substituents such that the resulting porphyrazine has catalytic activity for the production of chlorine dioxide from chlorite. The superscripted "a" represents the oxidation state of the Mn. The oxidation state may be any possible oxidation state. The oxidation state may be II, III, or IV in non-limiting examples. Axial ligands are represented by $L_1$ and $L_2$. Both $L_1$ and $L_2$ may be absent, or the complexes may be either 5-coordinate with one L ligand or 6-coordinate with two L ligands. The complexes may have charge balancing counter anions. A non-limiting example of a charge balancing counter anion is chloride ion. Further non-limiting examples of charge balancing counter anions are provided below.

An example where D1, D2, D3 and D4 are $N^+$—$R_{11}$, $N^+$—$R_{12}$, $N^+$—$R_{13}$, and $N^+$—$R_{14}$, respectively, is shown in formula VII:

Formula VII

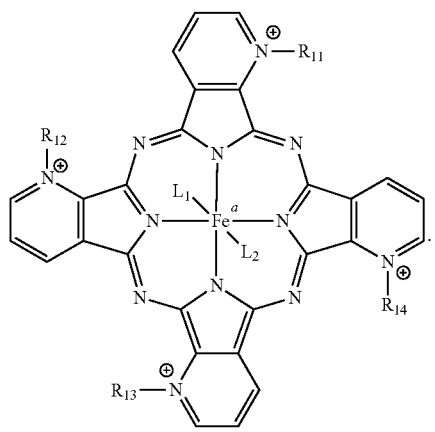

A regioisomer or positional substituted compound based on formula VI may be provided as a porphyrazine catalyst herein. A mixture of regioisomers or positional substituted compounds may be provided as a porphyrazine catalyst herein. Non-limiting examples of regioisomers, mixtures thereof or mixtures of positional substituted compounds that may be provided as a phorphyrazine catalyst are shown below in formulas VIII through XIV.

Formula VIII

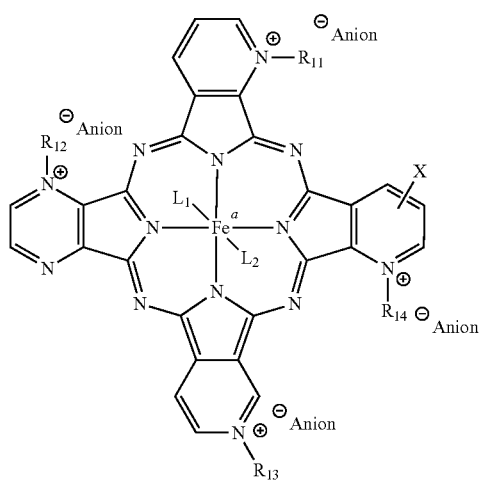

Due to the method of synthesis, mixed isomers can be prepared by using a mixture of dicyanoolefins as starting materials and a mixture of alkylating agents $R_{11}$-LG, $R_{12}$-LG, $R_{13}$-LG, and $R_{14}$-LG with LG being a typical leaving group. Examples of leaving groups include but are not limited to iodide, triflate, bromide and tosylate. Formulas IX and X show two of four possible regioisomers.

Formula IX

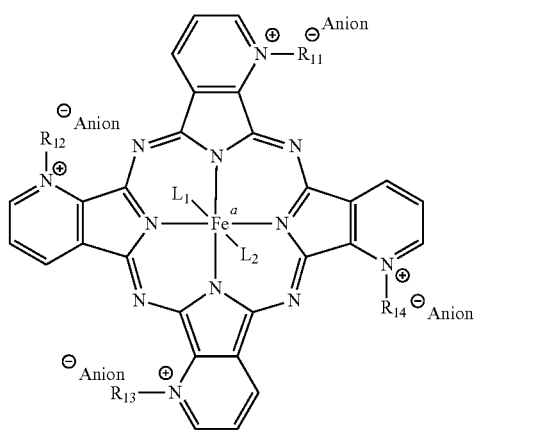

Formula X

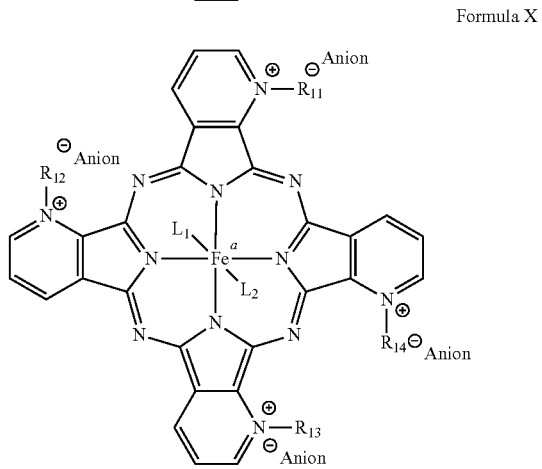

Formulas XI and XII show two of four possible additional regioisomers.

Formula XI

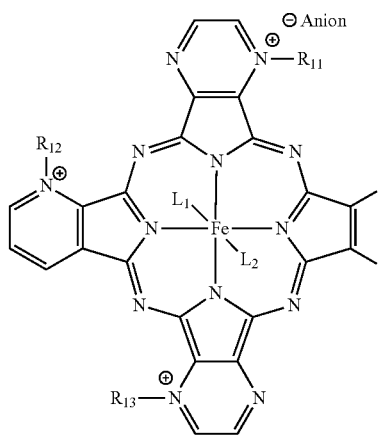

Formula XII

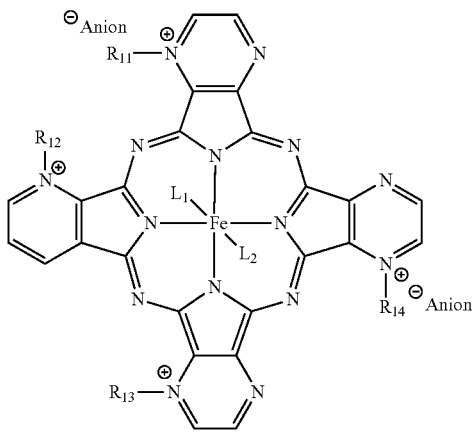

Formulas XIII and XIV show two of four possible additional regioisomers.

Formula XIII

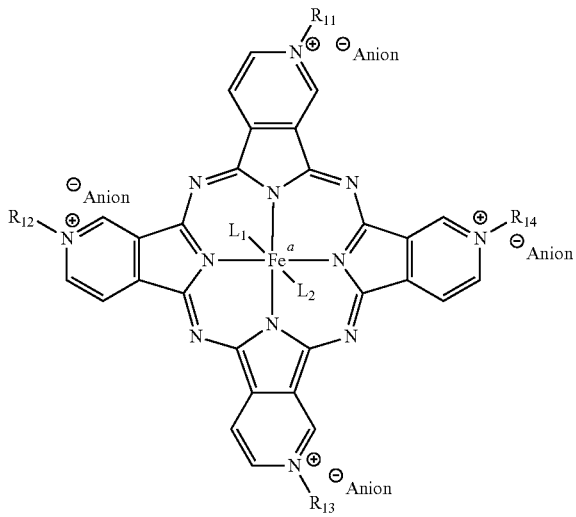

Formula XIV

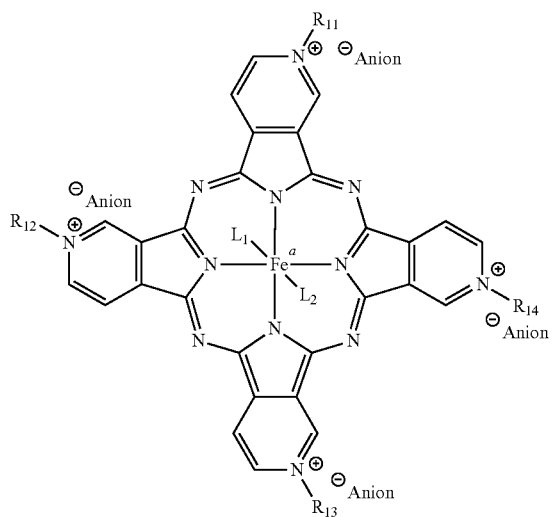

Any possible regioisomer or combinations thereof of any of the above phorphyrazine compounds may be provided as a porphyrazine catalyst in embodiments herein.

Any one or more of $R_5$, $R_6$, $R_7$, $R_8$, $R_9$, and $R_{10}$, or $R_{11}$, $R_{12}$, $R_{13}$, and $R_{14}$ may be independently selected from H; methyl; ethyl; propyl; isopropyl; n-butyl; sec-butyl; isobutyl; $CH_2$—$(CH_2)_{n1}$—$CH_3$ where n1=5-20; $CH_2$—$(CH_2)_{n2}$—$CH_2$—X where n2=0-20; —$CH_2(CO)$—$(CH_2)_{n3}$—$CH_2$—X where n3=0-20; or —$CH_2$—Ar—X where Ar may be phenyl, biphenyl or naphthyl. For the phenyl case, X may be attached ortho-meta- or para to the —$CH_2$— attached to the pyridoporphyrazine or the pyridoporphyrin. X is described below.

Any one or more of $R_5$, $R_6$, $R_7$, $R_8$, $R_9$, and $R_{10}$, or $R_{11}$, $R_{12}$, $R_{13}$, and $R_{14}$ may be independently selected from H; $(CH_2)_n$—X where n is 1 to 10 and X is COOH, COO(alkyl$_1$), CONH$_2$, CONH(alkyl$_1$), CON(alkyl$_1$)$_2$, CO($CH_2$)$_p$alkyl$_1$, OPO$_3$H$_2$, PO$_3$H$_2$, SO$_3$H, NH$_2$, N(alkyl$_1$)$_2$, or N(alkyl$_1$)$_3$·, where alkyl$_1$ is methyl, ethyl, propyl, butyl, pentyl, hexyl, heptyl, or octyl. Any one or more of $R_5$, $R_6$, $R_7$, $R_8$, $R_9$, and $R_{10}$, or $R_{11}$, $R_{12}$, $R_{13}$, and $R_{14}$ may be independently selected from $CH_2CH_2OCH_3$; $CH_2CH_2OCH_2CH_2OCH_3$; $(CH_2)_n$Ar—X, where X is as defined above; $(CH_2)_n$Ar—Y, where Y is as defined below; or $Y_2C(Z_1)_3$, where $Y_2$ is described below. $Z_1$ may be $CH_2OCH_2(CH_2)_nX$, $CH_2OCH_2(CH_2)_nY$, or $(CH_2)_nC(O)Y_2C(Z_2)_3$. $Z_2$ may be $CH_2OCH_2CH_2C(O)Y_2C(Z_4)_3$ and $Z_4$ may be $CH_2OCH_2CH_2X$, or $(CH_2)_nC(O)$—$Y_2$—$C(Z_5)_3$—$Z_5$ may be $CH_2OCH_2CH_2C(O)Y_2C(Z_6)_3$ and $Z_6$ may be $CH_2OCH_2CH_2C(O)O(CH_2CH_2O)_mCH_2CH_2O$, $(CH_2)_nOCH_2C(CH_2OH)_3$, $(CH_2)_nOCH_2CH(CH_2OH)_2$, $(CH)_nOCH_2C(CH_2OH)_2(CH_3)$, $(CH_2)_nOCH_2C[CH_2OCH_2C(CH_2OH)_3]_3$, $(CH_2)_nOCH_2C[CH_2OCH_2C(CH_2O[CH_2CH_2O]_mCH_2CH_2OX)_3$, $CH_2CONH$—Y, $CH_2CO$—Y, or $CH_2CO(CH_2)_p$—Y. p may be 1 or 2. Y may be OH or (O—$CH_2CH_2)_m$—$W_1$ or $(CH_2CH_2)_m$—$W_2$, where $W_1$ is OH, or (O—$(CH_2CH_2)_m$OH) and $W_2$ is $OR_{16}$, and $R_{16}$ is alkyl. m is 1 to 200. $Y_2$ may be —$(CH_2)_nO$—, —$(CH_2)_nNH$—, —$(CH)_nS$—; $CH_2CONH$—, $CH_2COO$—, or $CH_2CO(CH_2)_p$—, where p is 1 or 2, and n is 1 to 10.

Any one or more of $R_5$, $R_6$, $R_7$, $R_8$, $R_9$, and $R_{10}$, or $R_{11}$, $R_{12}$, $R_{13}$, and $R_{14}$ may be independently selected from H, $(CH_2)_m$Ar—X or $(CH_2)_m$Ar—Y, where Ar is substituted or unsubstituted phenyl or substituted or unsubstituted naphthyl, m is 1 to 200, and X and Y are as defined above.

Any one or more of $R_5$, $R_6$, $R_7$, $R_8$, $R_9$, and $R_{10}$, or $R_{11}$, $R_{12}$, $R_{13}$, and $R_{14}$ may be independently selected from $(CH_2)_n$—Y, where n is 1 to 10 and Y is as defined above.

Any one or more of $R_5$, $R_6$, $R_7$, $R_8$, $R_9$, and $R_{10}$, or $R_{11}$, $R_{12}$, $R_{13}$, and $R_{14}$ may be independently selected from $CH_2CONH$—Y, $CH_2COO$—Y, $CH_2CO$—Y, or $CH_2CO(CH_2)_P$—Y, where p is 1 or 2 and Y is as defined above.

Any one or more of $R_5$, $R_6$, $R_7$, $R_8$, $R_9$, and $R_{10}$, or $R_{11}$, $R_{12}$, $R_{13}$, and $R_{14}$ may be independently selected from $(OCH_2CH_2)_m$—Y, where m is 1 to 200, Y is as defined above.

Any one or more of $R_5$, $R_6$, $R_7$, $R_8$, $R_9$, and $R_{10}$, or $R_{11}$, $R_{12}$, $R_{13}$, and $R_{14}$ may be independently selected from $(OCH_2CH_2)_m$—X, where m is 1 to 200, and X is as defined above.

Any one or more of $R_5$, $R_6$, $R_7$, $R_8$, $R_9$, and $R_{10}$, or $R_{11}$, $R_{12}$, $R_{13}$, and $R_{14}$ may be independently selected from $Y_2$—X, where X and $Y_2$ are as defined above.

Any one or more of $R_5$, $R_6$, $R_7$, $R_8$, $R_9$, and $R_{10}$, or $R_{11}$, $R_{12}$, $R_{13}$, and $R_{14}$ may be independently selected from —$CH_2CH_2OCH_2CH_2OCH_2CH_2OCH_3$ or —$CH_2CO_2CH_2CH_3$.

In an embodiment, one of $R_5$, $R_6$, $R_7$, $R_8$, $R_9$, or $R_{10}$ is selected from one of the examples below other than H, and the remaining ones of $R_5$, $R_6$, $R_7$, $R_8$, $R_9$, or $R_{10}$ are H. In an embodiment, one of $R_{11}$, $R_{12}$, $R_{13}$ or $R_{14}$ is selected from one of the examples below other than H, and the remaining ones of $R_{11}$, $R_{12}$, $R_{13}$ or $R_{10}$ are H.

In some embodiments, a porphyrin or porphyrazine catalyst is provided in association with suitable ligands ($L_1$ and $L_2$) and/or charge neutralizing anions. $L_1$ and $L_2$ can be the same or different, and one or more may be absent. The structures above showing $L_1$ and $L_2$ thus include the possibility that $L_1$ and $L_2$ can be the same or different, and one or more may be absent. Ligands and charge neutralizing anions can be derived from any monodentate or polydentate coordinating ligand or ligand system or the corresponding anion thereof. Ligands and charge neutralizing anions may be independently selected from the group consisting of halide, oxo, aquo, hydroxo, alcohol, phenol, dioxygen, peroxo, hydroperoxo, alkylperoxo, arylperoxo, ammonia, alkylamino, arylamino, heterocycloalkyl amino, heterocyloaryl, amino, amine oxides, hydrazine, alkyl hydrazine, aryl hydrazine, nitric oxide, cyanide, cyanate, thiocyanate, isocyanate, isothiocyanate, alkyl nitrite, aryl nitrite, alkyl isonitrile, aryl isozutrile, nitrate, nitrite, azido, alkyl sulfonic acid, aryl sulfonic acid, alkyl sulfoxide, aryl sulfoxide, alkyl aryl sulfoxide, alkyl sulfenic acid, aryl sulfenic acid, alkyl sulfuric acid, aryl sulfinic acid, alkyl thiol carboxylic acid, aryl thiol carboxylic acid, alkyl thiol thiocarboxylic acid, aryl thiol thiocarboxylic acid, alkyl carboxylic acid, aryl carboxylic acid, urea, alkyl urea, aryl urea, alkyl aryl urea, thiourea, alkyl thiourea, aryl thiourea, alkyl aryl thiourea, sulfate, sulfite, bisulfate, bisulfite, thiosulfate, thiosulfite, hydrosulfite, alkyl phosphine, aryl phosphine, alkyl phosphine oxide, aryl phosphine oxide, alkyl aryl phosphine oxide, alkyl phosphine sulfide, aryl phosphine sulfide, alkyl aryl phosphine sulfide, alkyl phosphonic acid, aryl phosphonic acid, alkyl phosphinic acid, aryl phosphinic acid, alkyl phosphinous acid, aryl phosphinous acid, phosphate, thiophosphate, phosphite, pyrophosphite, triphosphate, hydrogen phosphate, dihydrogen phosphate, alkyl guanidino, aryl guanidino, alkyl aryl guanidino, alkyl carbamate, aryl carbamate, alkyl aryl carbamate, alkyl thiocarbamate, aryl thiocarbamate, alkyl aryl thiocarbamate, alkyl ditbiocarbamate, aryl dithiocarbamate, alkyl aryl dithiocarbamate, bicarbonate, carbonate* perchlorate, chlorate, chlorite, hypochlorite, perbromate, bromate, bromite, hypobromite, tetrahalomanganate, tetrafluoroborate, hexafluorophosphate, hexafluoroanitmonate, hypophosphite, iodate, periodate, metaborate, tetraaryl borate, tetra alkyl borate, tartrate, salicylate, succinate, citrate, ascorbate, saccharinate, amino acid, hydroxamic acid, thiotosylate, and anions of ion exchange resins, or systems. When the charge neutralizing complex has a net positive charge, then a negatively charged counter ion may be provided. When the charge neutralizing complex has net negative charge, a counter ion selected from alkaline and alkaline earth cations, organic cations, alkyl cations or alkylaryl ammonium cations may be provided. Ligands $L_1$ and $L_2$ may be independently selected from halide, oxo, aquo, hydroxo and alcohol. Anionic counterfoils may be halide ions. Halide ions include fluoro, chloro, bromo or iodo ions. Ligands and counterions may be the same or different. For example, a metallic complex may have one or two chloro axial ligands and 1, 2, 3, or 4 chloride ions as charge neutralizing anions.

Non-limiting examples of "alkyl" include a straight-chain or branched-chain alkyl radical containing from 1 to 22 carbon atoms, or from 1 to 18 carbon atoms, or from 1 to 12 carbon atoms. Further non-limiting examples of "alkyl" include include methyl, ethyl, n-propyl, isopropyl, n-butyl, isobutyl, sec-butyl, tert-butyl, pentyl, iso-amyl, hexyl, octyl, nonyl, decyl, dodecyl, tetradecyl, hexadecyl, octadecyl and eicosyl. Lower alkyl refers to a straight-chain or branched-chain alkyl radical containing from 1 to 6 carbon atoms.

Non-limiting examples of "aryl" include a phenyl or naphthyl radical. The phenyl or napthyl radical may carry one or more substituents selected from alkyl, cycloalkyl, cycloalkenyl, aryl, heterocycle, alkoxyaryl, alkaryl, alkoxy, halogen, hydroxy, amine, cyano, nitro, alkylthio, phenoxy, ether, trifluoromethyl, phenyl, p-tolyl, 4-methoxy-phenyl, 4-(tert-butoxy)phenyl, 4-fluorophenyl, 4-chiorophenyl, 4-hydroxyphenyl, and 1-naphthyl, 2-naphthyl, or similar substituents.

Non-limiting examples of "aralkyl" include an alkyl or cycloalkyl radical in which one hydrogen atom is replaced by an aryl radical. One example is benzyl, 2-phenylethyl.

"Heterocyclic" means ring structures containing at least one other kind of atom, in addition to carbon, in the ring. The most common of the other kinds of atoms include nitrogen, oxygen and sulfur. Examples of heterocycles include, but are not limited to, pyrrolidinyl, piperidyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, triazolyl and tetrazolyl groups.

Non-limiting examples of "cycloalkyl" include a cycloalkyl radical containing from 3 to 10, or from 3 to 8, or from 3 to 6 carbon atoms. Further non-limiting examples of such cycloalkyl radicals include, but are not limited to, cyclopropyl, cyclobutyl, cyclopentyl, cyclohexyl, cycloheptyl, cyclooctyl, and perhydronaphthyl.

The term "cycloalkenyl" means a cycloalkyl radical having one or more double bonds. Examples include, but are not limited to, cyclopentenyl, cyclohexenyl, cyclooctenyl, cyclopentadienyl, and cyclooctadienyl.

Embodiments also include any isomer of the any of the above porphyrin or porphyrazine catalysts or a method, kit or cartridge involving the same. Also included are tautomers of the compounds or a method, kit or cartridge involving the tautomers. Tautomers may include compounds wherein one or more of the various R groups are simple variations of the substituents as defined therein, or substituents which are a higher alkyl group than that indicated. In another example, anions having a charge other than 1 can be used instead of anions having a charge of 1. Examples of anions having a charge other than 1 include carbonate, phosphate, and hydrogen phosphate. Using anions having a charge other than 1 will result in a slight modification of the general formula for the compounds set forth above, but the skilled artisan will recognize the slight modification.

Embodiments herein provide an efficient, catalytic process for the generation of $ClO_2$ from chlorite ion ($ClO_2^-$). In an embodiment, the method includes contacting a chlorine salt in a solvent containing a catalytic amount of a particular iron porphyrin or iron porphyrazine catalysts. The iron porphyrazine catalyst may be a N-akylpyridinium porphyrazine catalyst. The solvent may be water. Chlorine dioxide may be produced efficiently in minutes at ambient temperature and pressure under mild, non-acidic conditions. The catalyst may be immobilized on a readily available clay. This allows facile recovery of the catalyst and would allow the construction of a flow system for continuous production of chlorine dioxide without electricity or other power sources.

Referring to FIGS. 1A-1B, MnTDMImP was previously found to be the most effective porhyrin catalyst. The rationale for the high activity is the strong electron withdrawing effect of the pendant imidazolium substituent since it modulates both the manganese redox potential and the pKa of water and hydroxide bond to the metal center. Recent data has shown that the readily available manganese porphyrazine catalyst Mn(II)TM-2,3-PyPz (either as separated regiosomers or a mixture thereof and the corresponding 3,4-isomer) are even more potent catalysts than MnTDMImp, with forty-fold higher activity. See Table 1 below. Related pthalocyanines, as well as Mn(III) and Mn(IV) oxidation states may be provided in embodiments herein. More recent data shows that catalysts with iron instead of manganese are surprisingly more active.

TABLE 1

MnTM-2,3-PyPz is 40-fold faster than MnTDMImP

| Compound | pH | $k_{RDS}$ ($M^{-1}$ $s^{-1}$) |
| --- | --- | --- |
| MnTDMImP | 4.7 | $1.36 \times 10^2$ |
| MnTDMImP | 6.8 | $5.62 \times 10^1$ |
| MnTM-2,3-PyPz | 4.5 | $5.29 \times 10^1$ |

In any method, kit, cartridge or composition herein, the following may be provided. A chlorite source may be provided in any suitable form. A chlorite source may be any chlorite salt. Non-limiting examples of chlorite salts that may be provided as a chlorite source are sodium chlorite, potassium chlorite, calcium chlorite and magnesium chlorite. A catalyst herein may be provided on a solid support. The solid support may be a clay. The solid support may be montmorillonite. The solid support may be but is not limited to silica, alumina, glass beads, functionalized polystyrene or organic polymers. The $ClO_2^-$ may be adsorbed on a substance, which may be but is not limited to clay, silica, alumina or organic polymers.

A method herein includes generating chlorine dioxide by exposing $ClO_2^-$ to at least one of an iron porphyrin catalyst or an iron porphyrazine catalyst. The iron porphyrin catalyst may be any compound that catalyzes the reaction of $ClO_2^-$ to $ClO_2$. The iron porphyrin catalyst may but is not limited to any of the iron porphyrin compounds described herein. The iron poyphyrazine catalyst may be any compound that catalyzes the reaction of $ClO_2^-$ to $ClO_2$. The iron porphyrazine catalyst may but is not limited to any of the iron porphyrazine compounds described herein. The method may include providing a chlorite source. The chorite source may be a chlorite salt. The chlorite source may be but is not limited to sodium chlorite, potassium chlorite, calcium chlorite or magnesium chlorite. The chlorite salt may be mixed with a solid filler. The chlorite source may be adsorbed on a substance. The substance may be but is not limited to clay, silica, alumina or organic polymers.

The at least one of the iron porphyrin catalyst or an iron porphyrazine catalyst may be adsorbed on a solid support. The solid support may be but is not limited to one or more of clay, silica, alumina, glass beads, functionalized polystyrene or organic polymers.

A method herein includes treating a substance with the $ClO_2$ generated by any other method herein, or by any reaction or use of any kit or cartridge herein. The substance may be but is not limited to water, air, a solid, a surface, cooling liquid, cooling liquid in a cooling tower, surfaces where biofilms may develop or have developed, food processing equipment, food products, and oral hygiene products.

An embodiment includes a cartridge system for producing chlorine dioxide from chlorite salts. The cartridge may be utilized in any manner apparent herein. The cartridge may be utilized as a portable chlorine dioxide generator, or a cartridge system for water purification with catalytic, in situ production of chlorine dioxide from chlorite salts. A cartridge type generator of chlorine dioxide using a fixed bed flow type reactor is described. Sodium chlorite, or other typical chlorite salts can be used either pure, mixed with a solid filler or adsorbed on a substance. The substance may be but is not limited to clay, silica, alumina, or organic polymers. An iron porphyrin and/or iron porphyrazine catalyst may also be adsorbed on a solid support. The solid support may be but is not limited to clay, silica, alumina, glass beads, functionalized polystyrene or organic polymers.

Figure 3A:
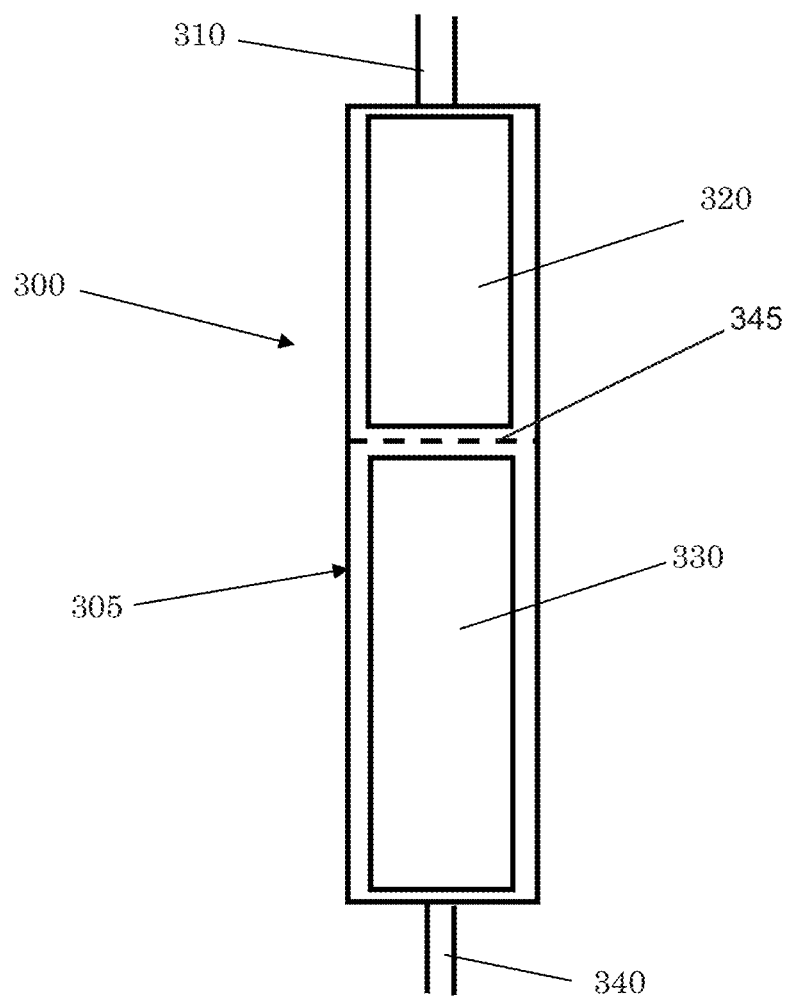
FIGS. 3A-B illustrate cartridges that may be employed as portable chlorine dioxide generators.

Referring to FIG. 3A, a cartridge 300 may include a housing 305, and a first compartment 320 including a chlorite salt. The chlorite salt may be but is not limited to sodium chlorite. The cartridge 300 may have a second compartment 330 having an iron porphyrin catalyst and/or an iron porphyrazine catalyst. Any iron porphyrin or iron porphyrazine catalyst may be provided in a cartridge, including any one or more of those listed herein. A fluid may be provided through an input 310 into the cartridge 300 and into the first compartment 320. The fluid may be water, or a solution made with water as the solvent. The chlorite salt may be dissolved in the fluid and then flow into the second compartment 330. The reaction to produce chlorine dioxide may occur in the cartridge 300. Fluid and/or chlorine dioxide may be provided through output 340. The cartridge may include additional constituents that could support the reaction to produce chlorine dioxide. For example, the cartridge could include buffer constituents.

As shown in FIG. 3A, the chlorite and catalyst may be in separate sections (as shown). Alternatively, the chlorite salt and catalyst could be mixed in a single section, or in a cartridge having no separate compartments. An interface, e.g., interface 345, between catalyst and chlorite salt may be included in a cartridge. The interface may be solid. The interface may be a complete barrier, or may have holes allowing retention of solid material. An interface could be made of a material that will allow mixing of the chlorite salt and catalyst upon a mechanical disruption. The mechanical disruption could be breaking of the interface. The mechanical disruption may be dissolution or other structural failure of the interface in the liquid. Holes in the interface may be provided in a configuration and/or size that does not allow passage of the chlorite salt or catalyst, but will allow passage of the fluid and solutes therein. The catalyst and chlorite compartments may be one unit, or two separate pieces that can be combined when in use. In the latter case, reuse of a catalyst bed may be more convenient. Alternatively, the cartridge may contain only the manganese porphyrin and/or manganese porphyrazine catalyst and the chlorite may be added to the fluid that is then allowed to flow over the catalyst bed.

The design of a cartridge may allow the production of either concentrated chlorine dioxide solutions to be later diluted into water that is to be treated or dilute (ppb-ppm) chlorine dioxide solutions that may be suitable for drinking or other such uses of water that has been decontaminated in this manner. An ion exchange cartridge may be inserted after the catalytic manganese flow reactor to reduce any effluent $ClO_X$ salts. The cartridge system may also be fitted with a sparging tube or frit to remove pure $ClO_2$ from the reaction stream. The desired concentration of $ClO_2$, concentrated or dilute, can be obtained by varying the catalyst loading, chlorite salt concentration, and flow rate of the chlorite solution over the catalyst bed.

Figure 3B:
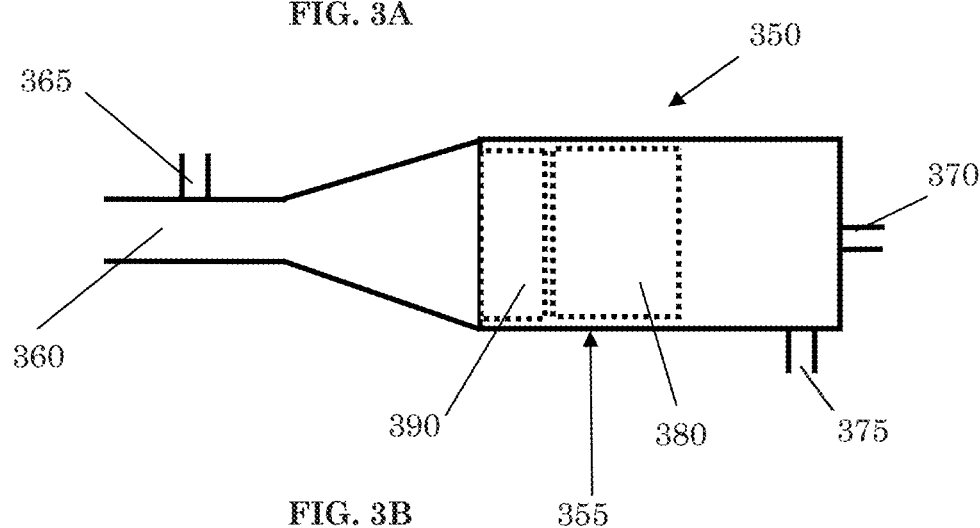

Referring to FIG. 3B, a cartridge 350 is illustrated. The cartridge 350 includes a housing 355, an input 360, an optional additional reagent input 365, an optional gas vent 370, and an output 375. Fluid may be delivered into the cartridge 350 through the input 360. The cartridge 350 may include an iron porphyrin and/or iron porphyrazine catalyst within housing 355. Optionally, the cartridge 350 includes a compartment 380 including an iron porphyrin and/or iron porphyrazine catalyst. A chlorite solution may be provided as the fluid. Alternatively, a chlorite salt may be provided within the cartridge 350. For example, the chlorite salt may be provided in optional compartment 390. A catalyst in cartridge 350 may be provided absorbed on a solid support. A chlorite source in cartridge 350 may be provided absorbed on a substance and/or mixed with a filler.

An embodiment includes a cartridge having any configuration that allows containment of a catalyst and/or a chlorite salt, and then passage of a fluid through the cartridge. An embodiment includes a cartridge like that of U.S. Pat. No. 6,740,223, which is incorporated herein by reference as if fully set forth, but where the electrode elements are replaced by a catalyst and/or chlorite salt herein.

A cartridge may be made of any suitable material. The suitable material may include but is not limited to glass, wood, metal, plastic, polycarbonate, and polyallomer. Any method herein may be conducted by implemented any cartridge herein. In an embodiment, fluid is pumped through a cartridge including a chlorite source and including an iron porphyrin and/or iron porphyrazine catalyst. The fluid may be water. In an embodiment, a chlorite source is provided to a fluid, and the fluid plus chlorite source is pumped through a cartridge including an iron porphyrin and/or iron porphyrazine catalyst.

An embodiment includes a kit for producing chlorine dioxide. Embodiments include a kit for sanitizing a substance. A kit may include any catalyst herein. A kit may include a chlorite source herein. A kit may include instructions to contact the chlorite source with the catalyst. Any cartridge herein may be provided in a kit. The instructions may include details of the reaction conditions as provided herein, and/or instructions for using any cartridge herein. The kit may include instructions to conduct any one or more method herein.

An embodiment includes a compound selected from $Fe^{III}TDMImP$, the ferric form, $Fe^{III}TM$-2,3-PyPz or the ferrous form, FeIITM-2,3-PyPz, any isomeric form of $Fe^{III}TM$-2,3-PyPz or FeIITM-2,3-PyPz, any iron porphyrin catalyst herein, any isomeric form of any iron porphyrin catalyst herein, any iron porphyrazine catalyst herein, or any isomeric form of any iron porphyrazine catalyst herein, and compositions comprising the same.

In an embodiment herein, less than 1 mol % of catalyst is needed for a method herein. In an embodiment, methods herein have more activity at pH less than 8. In an embodiment, no oxidants are present in a method herein. In an embodiment, $CO_2$ may be added in a method herein to maintain optimal pH. Catalyst may be recycled in a method herein. Air stripping during turnover may be utilized in a method herein to isolate $ClO_2$. A packed bed stripper, or sieve tray stripper may be implemented in a method herein to accomplish air stripping. $ClO_2$ may be recycled in a method herein. $ClO_2$ generated may be implemented for disinfection, or similar reactions, which may result in production of $ClO_2^-$: $ClO_2 + 1\ e^- \rightarrow ClO_2^-$. For example, the reaction of chlorine dioxide with trichlorophenol in water would produce dichloroquinoline, chlorite, acid, and chloride. The chlorite so produced could be subject to another round of catalysis to produce further chlorine dioxide. In an embodiment, a method herein may be utilized to generate chlorine dioxide and the method may further comprising exposing the chlorine dioxide generated or the catalyst/chlorite system and chlorine dioxide generated to pharmaceutical contaminated water.

In an embodiment, one or more iron catalysts herein can be used to generate chlorine dioxide for the treatment of water that has become contaminated with organic dyes commonly used in the manufacture of cloth and clothing. Globally, it is estimated that 120 tons of dye materials are released into environmental waters daily. Removal of such dyes has become an expensive challenge for the textile industry; biological treatment is too slow, and there is no efficient chemical treatment. Any method herein may be adapted to treat water contaminated with organic dye. The method may include exposing the water contaminated with the dye to chlorine dioxide generated by any method herein. The method may include generating the chlorine dioxide by any method herein. The method may include generating chlorine dioxide by any method described herein and exposing the water contaminated with the dye to the chlorine dioxide. The high activity and low cost of the catalysts could have an impact here. A method of generating chlorine dioxide for treating water contaminated with dye may employ a cartridge. The cartridge may comprise a housing, which may comprise at least one of an iron porphyrin catalyst or an iron porphyrazine catalyst. The cartridge may also comprise a source of $ClO_2^-$. The cartridge may be used to generate chlorine dioxide. The method employing the cartridge may include passing the water contaminated with dye through the cartridge. The method employing the cartridge may include allowing or directing the chlorine dioxide produced from the cartridge to pass through the water contaminated with dye. A method may include generating chlorine dioxide with any kit herein. The kit may comprise at least one of an iron porphyrin catalyst or an iron porphyrazine catalyst. The kit may also include a source of $ClO_2^-$. The kit may be used to generate chlorine dioxide. The method may include exposing the water to chlorine dioxide generated with the chlorite ion and iron catalyst from the cartridge. The step exposing the water may be done with chlorine dioxide generated by any method or device herein.

In an embodiment, one or more iron catalyst herein can be used to generate chlorine dioxide for the extraction of liquid fuels and commodity chemicals from biomass. Here the challenge is to separate the plant cellulose from lignin. The iron catalysts herein could find use in this application due to the fast reaction and mild conditions used. The method may comprise exposing plant material to chlorine dioxide generated by any method herein. The method may comprise generating the chlorine dioxide by any method herein. The method may comprise generating chlorine dioxide with any cartridge herein. The cartridge may comprise a housing and at least one of an iron porphyrin catalyst or an iron porphyrazine catalyst. The cartridge may also comprise a source of $ClO_2^-$. The method of generating chlorine dioxide may implement any kit herein. The kit may comprise at least one of an iron porphyrin catalyst or an iron porphyrazine catalyst. The kit may also comprise a source of $ClO_2$. The may include exposing the plant material to chlorine dioxide generated with the kit. Chlorine dioxide generated by any method or device herein can be used to treat extract liquid fuels and commodity chemicals from biomass.

Additional embodiments include those formed by reading any dependent claim in the claim listing below as being dependent on any one or more preceding claim up to and including its base independent claim.

Further additional embodiments include those formed by supplementing any single embodiment herein or replacing an element in any single embodiment herein with one or more element from any one or more other embodiment herein.

EXAMPLES

The following non-limiting examples are provided to illustrate particular embodiments. The embodiments throughout may be supplemented with one or more detail from any one or more example below. Still further embodiments include a method utilizing any iron porphyrin or iron porphyrazine herein under any one experimental condition described in the following examples, or utilizing any iron porphyrin or iron porphyrazine herein under any one experimental condition that can be inferred based on those described in the following examples, and/or one or more element from an embodiment may be substituted with one or more detail from one or more example below.

Certain examples below include manganese, rather than iron, catalysts. A switch from manganese to iron in each of these certain examples, and drawings illustrating the same, form prophetic examples herein.

Example 1

Aliquots of $ClO_2^-$ and $Mn^{III}TDMImP$ stock solutions were added to 10 mL 100 mM buffer in a test tube with side arm and immediately sealed using a rubber stopper outfitted with a fritted sparging tube. The reaction mixture was sparged with He during the course of the reaction through another fritted bubbler into a second test tube containing 20-40 mL of aqueous 200 mM KI. The reaction was allowed to run for 20 minutes, at which point the trapping solution was transferred to an Erlenmeyer flask and titrated with 0.05 M sodium thiosulfate to a colorless endpoint (using a starch indicator). To the colorless solution, approximately 5 mL of concentrated $H_2SO_4$ was added to liberate more $I_2$. This solution was titrated again. The number of moles of $ClO_2$ transferred during the sparging was determined by dividing the number of moles of thiosulfate used in the second titration by 4. By subtracting the number of moles of $ClO_2$ calculated from the number of moles of thiosulfate used in the first titration and diving the total number by 2, the number of moles of $Cl_2$ transferred was determined.

Example 2—Heterogeneous Catalysis on Clay Support

Mn(III)TDMImP was supported on montmorillonite KSF by adding 1 mL of 2.5 mM MnTDMImP to a stirring, aqueous suspension of montmorillonite (~200 mg/mL). Immediately the clay adsorbed the cationic porphyrin, and the supernatant had no color when the porphyrin-clay suspension was allowed to settle. Using the clay-bound MnTDMImP, catalyst-free solutions of $ClO_2$ could be prepared by stirring unbuffered solutions of $NaClO_2$ with aliquots of the MnTDMImP/clay slurry in an open reaction vial, followed by filtration through Celite/glass wool in a Pasteur pipet to remove the catalyst. Using 2 mg of the monified clay, a 5.5 mM solution of $NaClO_2$ produced 1 mM $ClO_2$ solution in 15 minutes (by UV-Vis analysis). With larger amounts of the MnTDMImP/clay (10-100 mg), the reaction was complete in less than 10 minutes, producing a catalyst-free 2.1 mM $ClO_2$ solution from a 9.5 mM solution of $NaClO_2$.

Example 3—Methyl Orange Test

In order to indirectly test for the generation of hypochlorite ($ClO^-$) during turnover, methyl orange (MO, 4-dimethylaminoazobenzene-4'-sulfonic acid sodium salt) was added to the reaction of chlorite ($ClO_2^-$) and MnTDMImP at pH 4.7. MO reacts with chlorinating oxidants such as $ClO^-$, producing dichlorodimethylaniline (DDA). DDA can be extracted from the aqueous medium with heptane and observed by GC-MS (m/z=188).

Figure 4:
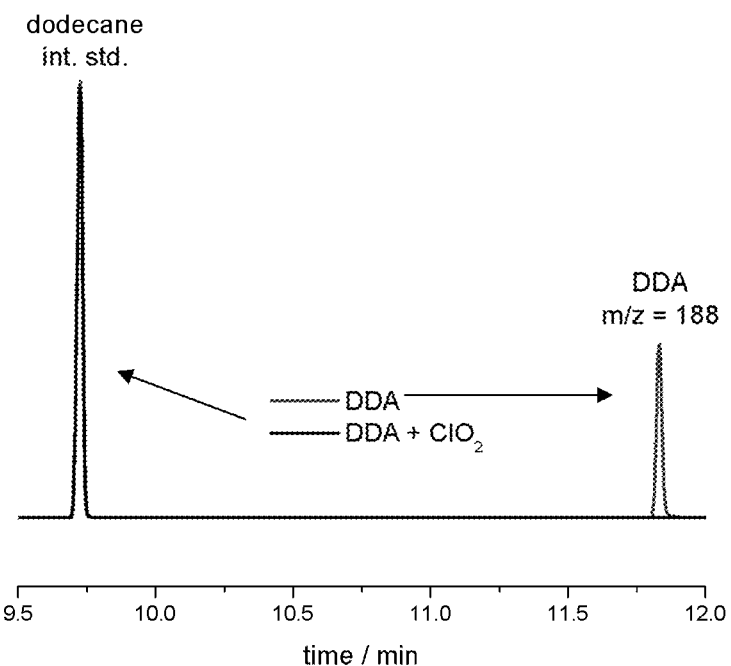
FIG. 4 illustrates a GC-MS chromatogram of authentic DDA and the extract of a reaction of DDA reacted with $ClO_2$.

As controls, the reactions of MO with chlorite $ClO_2^-$, $ClO^-$, and chlorine dioxide ($ClO_2$) were tested. $ClO_2^-$ did not react at all with methyl orange at pH 4.7, whereas the other two oxidants quickly bleached the methyl orange chromophore (464 nm). $ClO^-$ produced dichlorodimethylaniline (DDA), detectable by GC-MS. No DDA was ever observed in reactions of MO with $ClO_2$. Referring to FIG. 4, however, it was observed that $ClO_2$ quickly oxidized away authentic DDA to unknown products. The absence of DDA observable in reactions of MO and $ClO_2$ does not prove that DDA is not transiently produced.

Figure 5:
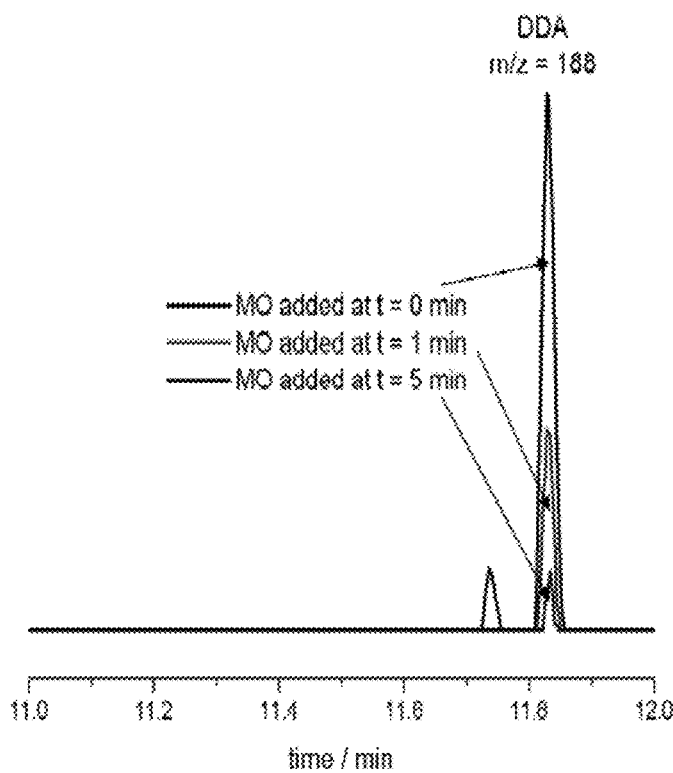
FIG. 5 illustrates a GC-MS chromatogram of DDA generated when Methyl Orange (MO) was present during the turnover reaction of MnTDMImP and $ClO_2^-$.

Referring to FIG. 5, when MO was present in a solution of MnTDMImP prior to the addition of $ClO_2^-$, a very small amount DDA (ca. 2 μmol) could be observed by GC-MS in heptane extracts of the reaction medium (1 mM $ClO_2^-$, 1 mol % catalyst, 100 μmol MO). When MO was added to the catalytic reaction after 1 and 5 minutes of reaction, less DDA was observed. Because DDA is consumed by $ClO_2$ which is being generated during turnover, heptane extraction of the reaction mixture was done 1 minute after MO was added. Further, when MO was added to completed reactions of MnTDMImP/$ClO_2^-$ (reaction time=10-30 min), no DDA was observed. This qualitative experiment therefore asserts that a species capable of chlorinating MO is produced during turnover. Given the above controls and our proposed mechanism, we assert that this chlorinating species is $ClO^-$.

Example 4—Quantifying $ClO_2$ by Iodometry

At neutral pH, both $ClO_2$ and $Cl_2$ will react with iodide ($I^-$) to produce iodine ($I_2$) (Reactions 1 and 2).

  (1)

  (2)

In addition, in the presence of $H_2SO_4$, the $KClO_2$ produced in Reaction 1 above will further oxidize 2 $I^-$ to $I_2$.

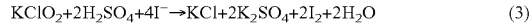  (3)

By sparging the reaction vessel of $ClO_2^-$ and MnTDMImP with helium into a concentrated $I^-$ solution, $I_2$ was produced (Reactions 1 and 2), which was titrated to a colorless endpoint with sodium thiosulfate, after which the solution is acidified with $H_2SO_4$ (Reaction 3) and re-titrated to a second colorless endpoint. From these two titrations, the effective amounts of both $ClO_2$ and $Cl_2$ produced and isolated from the catalytic decomposition of $NaClO_2$ can be determined.

Example 5—Synthesis

Synthesis and Characterization of Cationic Manganese and Iron Porphyrazines. Tetrapyridinoporphyrazine (PyPz).

Figure 7:
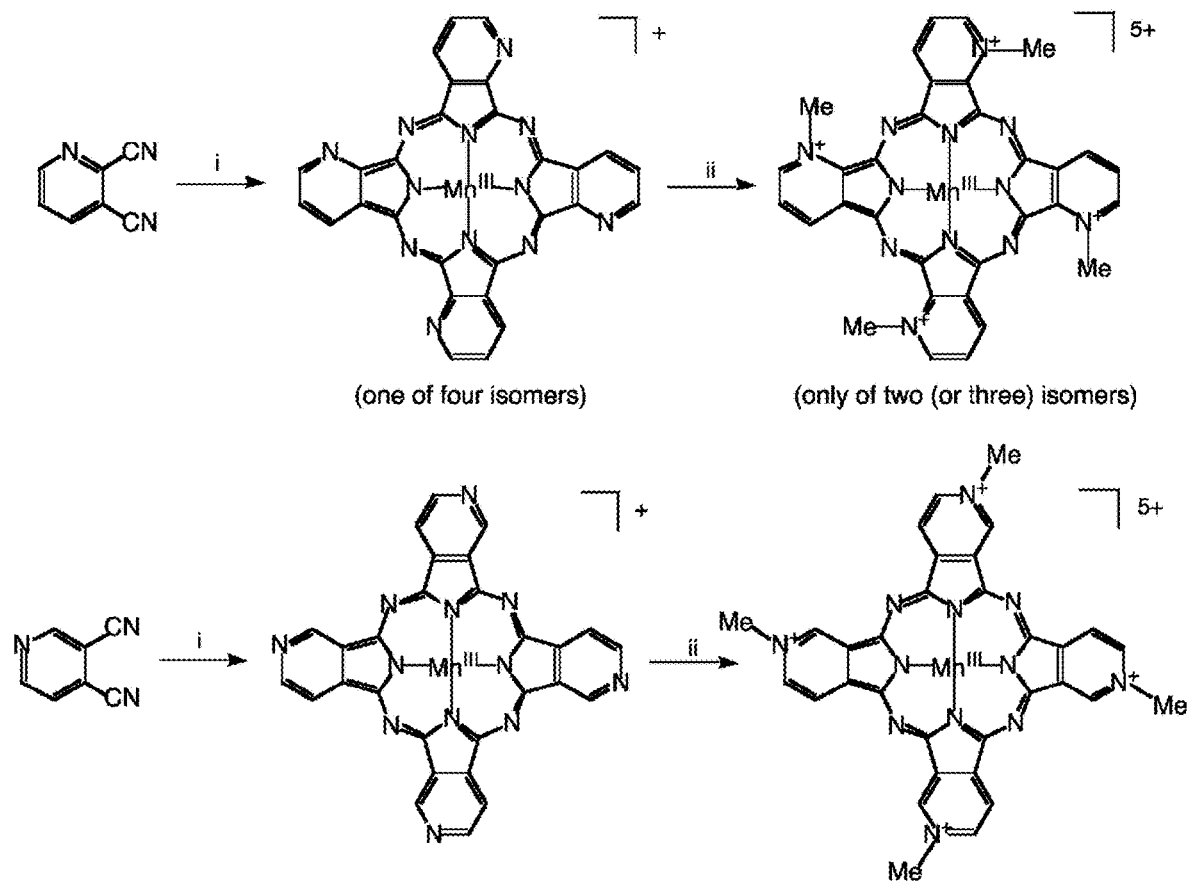
FIG. 7 illustrates the synthesis of two highly active catalysts, MnTM-2,3-PyPz and MnTM-3,4-PyPz. These can be any of the various regioisomers or a mixture thereof.

Water soluble cationic manganese tetrapyridinoporphyrazines were prepared using a modification of Wöhrle's method. Anhydrous manganese acetate was allowed to react with either 2,3- or 3,4-dicyanopyridine in a salt bath at 200° C. The green colored crude manganese tetrapyridinoporphyrazines (MnPyPpz) were precipitated with hexanes and then extracted with DMF to afford blue pure Mnpypz. Both Mn(2,3-pypz) and Mn(3,4-pypz) have four isomers each. Methylation was performed using dimethylsulphate in DMF yielding the cationic manganese tetrapyridinoporphyrazines as the methylsulfate salt (FIG. 7). The iron complexes have also been synthesized.

Aetato(2,3-Pyridinoporphyrazinato)manganese(III) (Compound 1)

2,3-Dicyanopyridine (0.50 g, 3.9 mmol) and manganese acetate (0.17 g, 0.98 mmol) were dissolved in 1-chloronaphthalene (50 mL) and heated for 12 h at 200° C. Acetone (250 mL) was added to the cooled reaction mixture. The dark green product was filtered, washed with acetone and dried. Yield: 0.55 g (90%). Alternate method, 2,3-dicyanopyridine (0.50 g, 3.9 mmol) and manganese acetate (0.17 g, 0.98 mmol) were placed in a 4-mL vial and heated at 200° C. for 4 hours. The deep blue product was washed with acetone and dried. Yield: 0.59 g (95%).

Acetato(N,N',N'',N'''-tetramethyltetra-2,3 pyridinoporphyrazinato)manganese(III) methylsulfate (Compound 2)

Compound 1 (0.25 g, 0.40 mmol) was suspended in dry NMP (or DMF) (50 mL) and dimethyl sulfate (3.8 mL, 40 mmol) was added. The mixture was heated at 120° C. with stirring under argon for 12 h. Acetone (250 mL) was added to the cooled reaction mixture. The dark purple product was filtered, washed with acetone and dried. Yield: 0.385 g (85%).

Chloro(2,3-pyridinoporphyrazinato)iron(III) (Compound 3)

2,3-Dicyanopyridine (0.50 g, 3.9 mmol) and iron(II) chloride hydrate (0.20 g, 1.0 mmol) were placed in a 4-mL vial and heated at 200° C. for 4 hours. The deep green product was washed with acetone and dried. Yield: 0.58 g (95%).

Chloro(N,N',N'',N'''-tetramethyltetra-2,3 pyridinoporphyrazinato)iron(III) methylsulfate (Compound 4)

Compound 3 (0.25 g, 0.41 mmol) was suspended in dry DMF (or NMP) (50 mL) and dimethyl sulfate (3.8 mL, 40 mmol) was added. The mixture was heated at 120° C. with stirring under argon for 12 hours. Acetone (250 mL) was added to the cooled reaction mixture. The dark purple product was filtered, washed with acetone and dried. Yield: 0.400 g (88%).

$PF_6$ Salts of Compounds 2 and 4.

The $PF_6$ salts of compound 2 and 4 were synthesized by anion exchange. Compound 2 (or 4) (0.20 mmol) was dissolved in $H_2O$ (10 mL) and added to a solution of $NH_4PF_6$ (0.75 g, 4.7 mmol) in $H_2O$ (10 mL). The precipitate was filtered, washed with $H_2O$ and dried. The yield was quantitative for both manganese and iron.

3,4 Isomers of Compounds 2 and 4.

The 3,4 isomers of compounds 2 and 4 were synthesized by using 3,4-dicyanopyridine instead of 2,3-dicyanopyridine. The overall yield of the manganese isomer was lower at 55%. Moreover, this complex was very sensitive and decomposed quickly even at low pH. The overall yield of the iron 3,4-isomer was similar to the iron 2,3-isomer at 82%.

The compounds were tested as oxidation catalysts and promoters.

Oxidation of Bromide.

Oxone (200 μM) was added to Mn(TM-2,3-PyPc) (20 μM), NaBr (10 mM) in acetate buffer (pH=4.9) in a cuvette. The UV-vis spectrum showed the presence of Br3-. Phenol Red (50 μM) was added to the cuvette. The UV-vis spectrum indicated bromination of the phenol red to bromophenol blue. When $H_2O_2$ (2 mM) was used as the oxidant, bromophenol blue was also produced as indicated by the UV-vis spectroscopy.

Oxidation of Chloride.

Oxone (200 μM) was added to Mn(TM-2,3-PyPc) (20 μM), NaCl (200 mM) in acetate buffer (pH=4.9) in a testtube. The tube was shaken for 15 s and then methyl orange (200 μM) was added to the testtube and the tube was shaken for 1 min. Hexane was added to extract the organic soluble molecules and GC-MS indicated the presence of mono- and dichloroaniline.

Epoxidation of CBZ.

Oxone (300 nmol) was added to Mn(TM-2,3-PyPc) (50 nmol), CBZ (200 mmol) in acetate buffer (pH=4.9) in a testtube. By HPLC analysis, CBZ oxide was produced.

Octakis[(bismethyl)imidazoliumyl]tetraazaporphyrin $[H_2(Me_2-Im)_8TAP]^{8+}$

Figure 8:
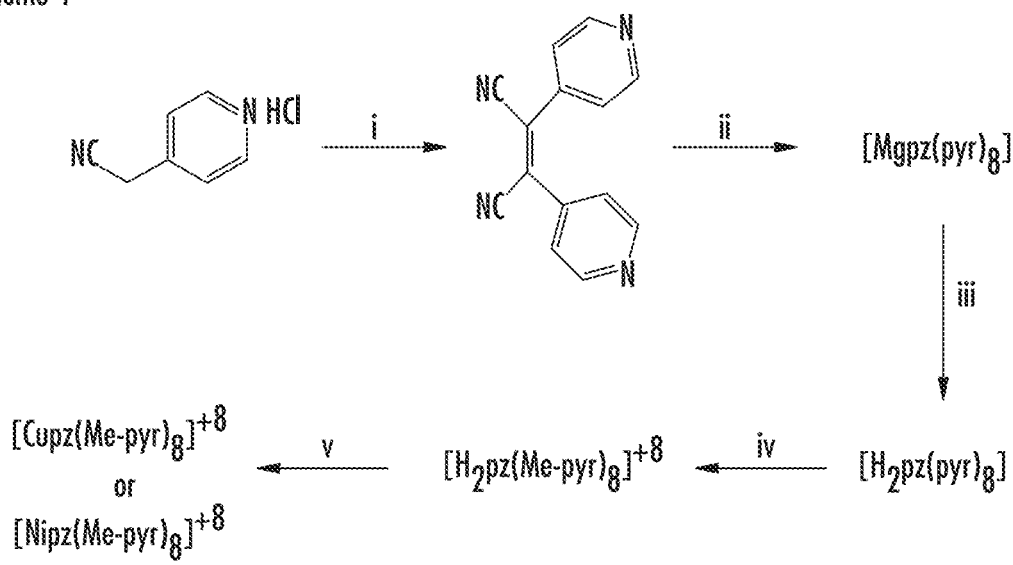
FIG. 8 illustrates the synthesis of Barrett and Hoffman's octacationic pyridium substituted tetraazapophyrin.
Figure 9:
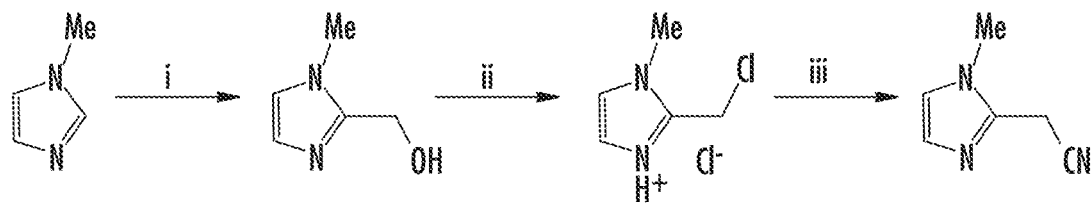
FIG. 9 illustrates the synthesis of (1-methyl-1H-imidazol-2-yl)acetonitrile.
Figure 10:
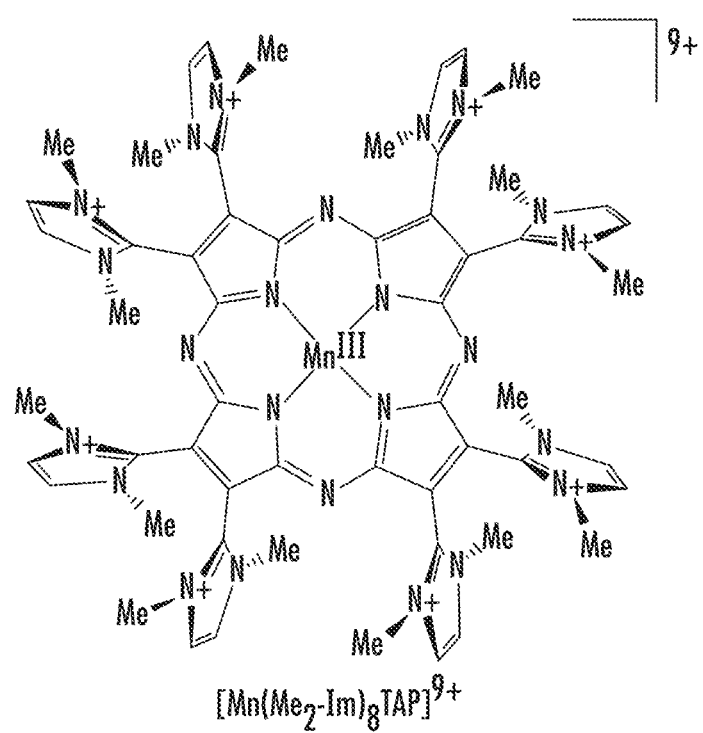
FIG. 10 illustrates the manganese octakis [(bismethyl) imidazoliumyl]tetraazaprophyrin.

The synthesis of octakis[(bismethyl)imidazoliumyl]tetraazaporphyrin will be performed in a similar fashion to the synthesis of Barrett and Hoffman's octacationic pyridium substituted tetraazaporphyrin (FIG. 8). Barrett and Hoffman first synthesized 2,3-bis(4-pyridyl-2,3-dicyanomaleonitrile from oxidative dimerization of 4-pyridylacetonitrile hydrochloride. Since no commercial sources of (1-methyl-1H-imidazol-2-yl)acetonitrile are available, this compound was prepared by a procedure by Reese (FIG. 9). 1-Methylimidazole was allowed to react with excess paraformaldehyde at 160° C. to yield (1-methylimidazol-2-yl)methanol. The methanol complex was then allowed to react with thionyl chloride at reflux to give 2-(chloromethyl)-1-methylimidazole hydrochloride. Sodium cyanide was then allowed to react with this chloro complex to yield 1-methylimidazol-2-yl-acetonitrile. With 1-methylimidazol-2-yl-acetonitrile synthesized, following Barrett and Hoffman's procedure, the manganese octakis[(bismethyl)imidazoliumyl]tetraazaprophyrin should be able to be synthesized (FIG. 10).

Example 6—Proposed Mechanism I

Figure 2A:
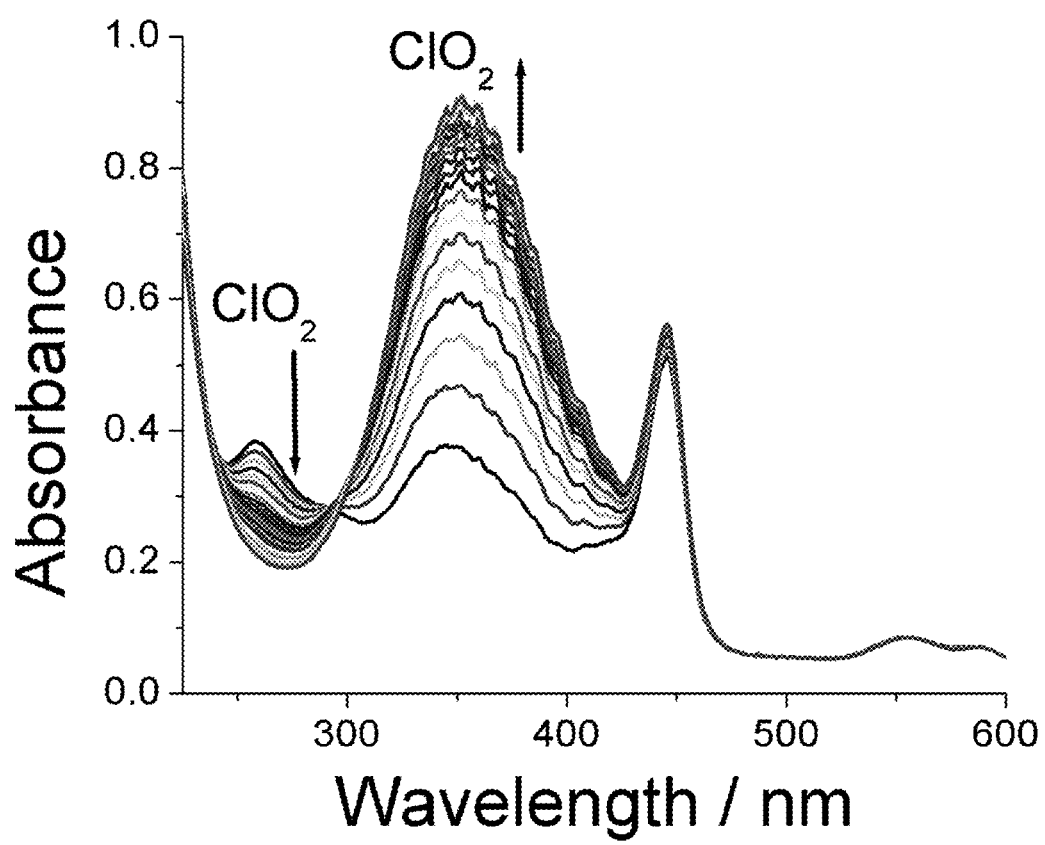
FIG. 2A illustrates Absorbance v. wavelength.
Figure 2B:
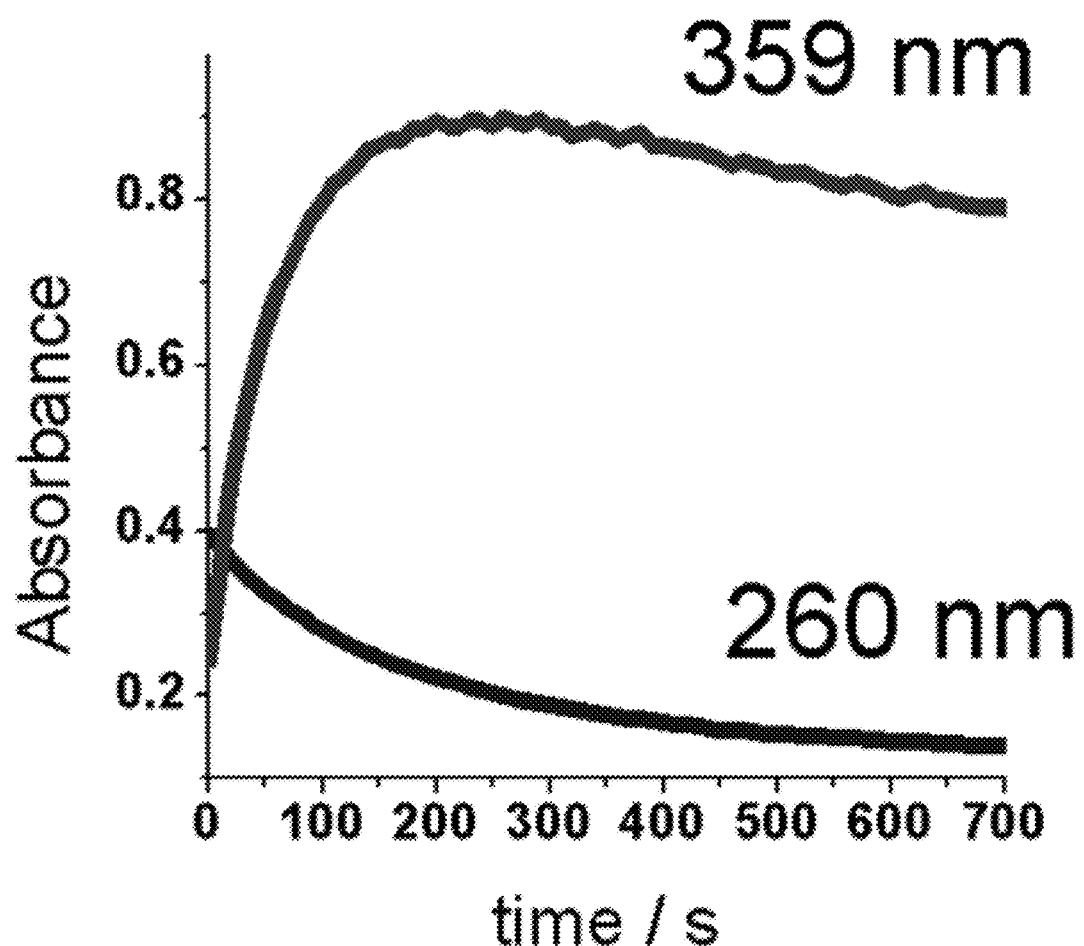
FIG. 2B illustrates a time resolved UV-vis spectra of $ClO_2$ generation.

Referring to FIGS. 2A-2B, a time resolved UV-vis spectra of $ClO_2$ (359 nm) generation when 10 μM MnTDMImP (445 nm) is mixed with 1.9 mM $NaClO_2$ (260 nm) at pH 4.7 (100 mM acetate buffer) and T=25° C. The reaction time shown is 240 s, scanning every 10 s. As shown, upon mixing freshly prepared sodium chlorite solutions with MnTDMImP, a large and immediate increase in the UV absorbance at 359 nm signals the formation of $ClO_2$. The appearance of $ClO_2$ occurred within seconds, concurrent with a complete decrease in the $ClO_2^-$ absorbance at 260 nm. The acid-catalyzed disproportionation of $ClO_2^-$ is sluggish above pH 3-4 and was insignificant on the time-scales studied here. During the initial burst of reaction, ~50 equiv of $ClO_2$ were quickly generated from 190 equiv of $ClO_2^-$. $O_2$-evolution, as monitored using a Clark electrode, was insignificant (<2%) The only porphyrin species observed in solution during turnover was the starting $Mn^{III}$ catalyst, as evidenced by the unshifted and undiminished Soret band at 445 nm. Significantly, the process also proceeded efficiently when the catalyst was adsorbed on montmorillonite clay.

The manganese porphyrin-catalyzed appearance of $ClO_2$ was observed from pH 4.7-6.8 over the temperature range 5-35° C. When $ClO_2^-$ was mixed rapidly with MnTDMImP (0.5 mol %) the observed concentration of $ClO_2$ produced reached a plateau within two minutes (FIG. 2B). Initial turnover frequencies at 25° C. for 2 mM $ClO_2^-$ and 10 μM catalyst were 1.00, 1.03, and 0.47 $s^{-1}$ at pH 4.7, 5.7, and 6.8, respectively, but these bulk values could be underestimates. The maximum amount of $ClO_2$ achieved was not temperature dependent.

The hypochlorite ion produced in the initial step would also be expected to oxidize $Mn^{III}$TDMImP as shown in Scheme 1. This stoichiometry predicts that five equiv of $ClO_2^-$ would be dismutated to 4 equiv of $ClO_2$ and 1 equiv of $Cl^-$ in this process. The observed unchanged oxidation state of the catalyst during turnover requires that any change in the $Mn^{III}$ porphyrin oxidation state be slow relative to $Mn^{III}$-regenerating reactions. As $ClO^-$ is a fast oxidant of $Mn^{III}$, the oxidation of $Mn^{III}$ by $ClO_2^-$ may be the rate-determining step of the overall catalytic cycle. At neutral pH, the calculated reduction potentials for the oxoMn$^V$/Mn$^{III}$ couple are lowest for TDMImP. Therefore, the imidazolium porphyrin should be oxidized most readily by $ClO_2^-$, which is consistent with oxo-transfer from $ClO_2^-$ being the RDS. At higher pH (where no $ClO_2$ generation was observed), $ClO_2^-$ should be strong enough to oxidize $Mn^{III}$ fully to $Mn^V$ based on the predicted energetics of both species. At pH 8.0 the reaction of $ClO_2^-$ and $Mn^{III}$TDMImP produced the O=$Mn^{IV}$ porphyrin, characterized by its broadened and slightly blue-shifted Soret. Presumably, $ClO_2^-$ oxidizes $Mn^{III}$ to oxoMn$^V$, which is quickly reduced by another $ClO_2^-$ to oxoMn$^{IV}$. The catalytic cycle in Scheme 1 would then stall at the $Mn^{IV}$ oxidation state because the O=$Mn^{IV}$ compound cannot efficiently oxidize $ClO_2^-$ and return to the resting $Mn^{III}$ state at this pH.

$ClO_2$ gas generated from the catalytic decomposition of $ClO_2^-$ was removed via efficient sparging of a reaction vessel charged with pH 6.8 phosphate buffer, $ClO_2^-$, and the catalyst. This effluent was bubbled through chilled, distilled water, which took on the characteristic color of dilute aqueous $ClO_2$ and could be confirmed by UV-Vis spectroscopy. The $ClO_2$ collected in this way was trapped and titrated with added iodide. Iodide is readily oxidized to $I_2$ by $ClO_2$, which could then be quantified by titrimetry. Using this procedure, 46.6 μmoles of $ClO_2$ were recovered from a 25° C. reaction of 98.4 μmoles of $NaClO_2$ with 10 μM MnTDMImP (reaction volume 10 mL) at pH 6.8 (60% yield, ~500 turnovers). A small amount of iodide oxidation attributable to $Cl_2$ (3.7 μmol) was also observed.

The various reactions of $ClO_2^-$ with metalloporphyrins reported to date are highly diverse in terms of intermediates and products. Accordingly, it is instructive to compare the reactivity of manganese porphyrin or phorphyrazine catalyst systems with that of other systems, both enzymatic and synthetic. Most notably, a water-soluble synthetic iron porphyrin that generates $O_2$ from $ClO_2^-$ has been reported as a biomimic of the heme protein Cld. However, two other iron porphyrins were shown to dismutate $ClO_2^-$ directly to chlorate ($ClO_3^-$) and chloride ($Cl^-$) with no observation of $O_2$. Collman and Brauman, who used $ClO_2^-$ with a synthetic manganese porphyrin catalyst in oxidations of cyclohexane, also observed $O_2$ evolution in non-aqueous media. The heme-thiolate enzyme chloroperoxidase transiently generates $ClO_2$ from $ClO_2^-$, ultimately producing a mixture of $ClO_3^-$, $Cl^-$, and $O_2$ via undetermined mechanisms. By contrast, a recent mechanistic study of $ClO_2^-$ decomposition by horseradish peroxidase (HRP) has shown that $ClO_2^-$ acts as both oxidant and reducing agent in a peroxidase cycle that generates $ClO_2$, but not $ClO_3^-$. The present embodiments represents the only known generation of $ClO_2$ from a synthetic porphyrin system.

The proposed mechanism for $ClO_2^-$ generation by manganese porphyrin or phorphyrazine is intriguing for its pronounced differences with a proposed mechanism for Cld and the iron porphyrin Cld-mimics. In Cld, the Cld-mimic Fe porphyrin, and MnTDMImP, $ClO_2^-$ acts as a 2-electron oxo-transfer agent, producing either an oxoiron$^{IV}$ porphyrin cation-radical or dioxoMn$^V$ as well as an equivalent of $ClO^-$. In the case of Cld and the iron mimic, the newly formed $ClO^-$ presumably reacts with Compound I to form an oxygen-oxygen bond, leading to the release of $O_2$. However, $ClO^-$ produced from the oxidation of $Mn^{III}$TDMImP by $ClO_2^-$ appears not to react with the newly-formed dioxoMn$^V$ species, but instead diffuses away to oxidize a second $Mn^{III}$ site.

It appears that dioxoMn$^V$ prefers an outer-sphere electron transfer from $ClO_2^-$ over the O—O bond-forming inner sphere reaction with $ClO^-$. This behavior might be influenced by electrostatics. As low as pH 5, the core of the catalyst exists as an anionic, trans-dioxo species $[O=Mn^V=O]^-$. The work required to bring together two anions in an inner-sphere process could be far greater than that necessary for an outer sphere process (where $ClO_2^-$ need only come qualitatively near the oxo species). Charge has been shown to be a powerful mediator of porphyrin reactivity, as in the example of olefin epoxidation by trans-dioxoMn$^V$ porphyrins.

Example 7—Proposed Mechanism II

Figure 6A:
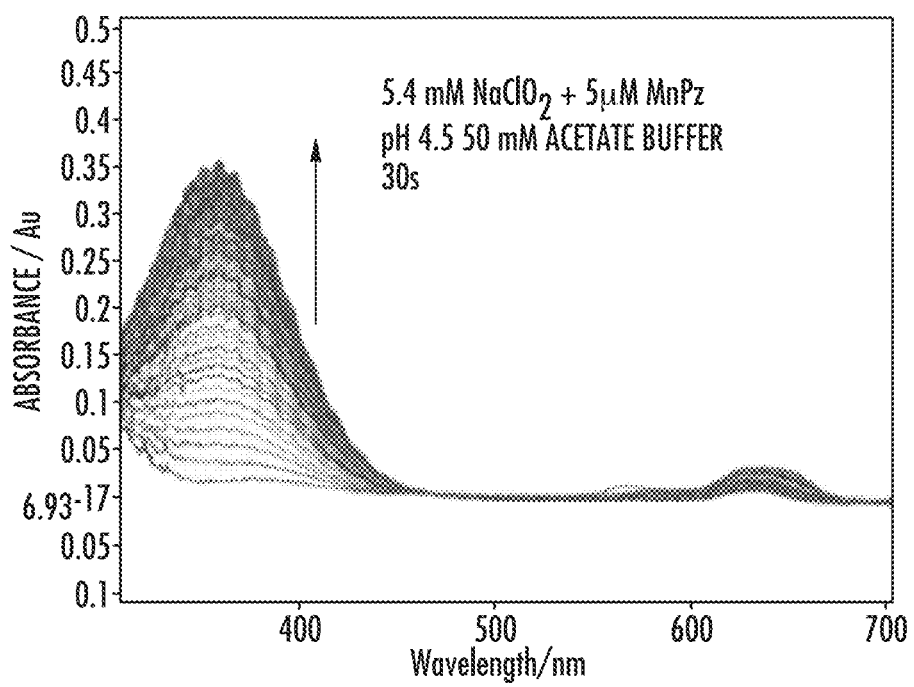
FIGS. 6A-C illustrate (A and B) Spectroscopic changes showing rapid and efficient production of chlorine dioxide upon addition of the Mn catalyst to a sodium chlorite solution. (C) Kinetic traces showing the very fast reaction rate for Mn(II)TM-2,3-PyPz.
Figure 6B:
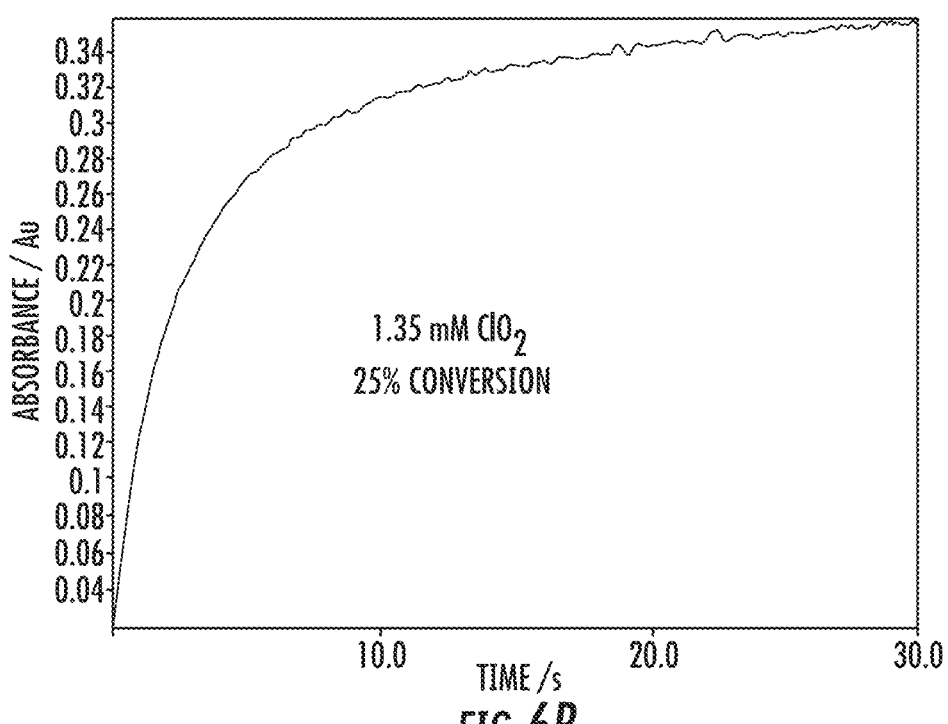
Figure 6C:
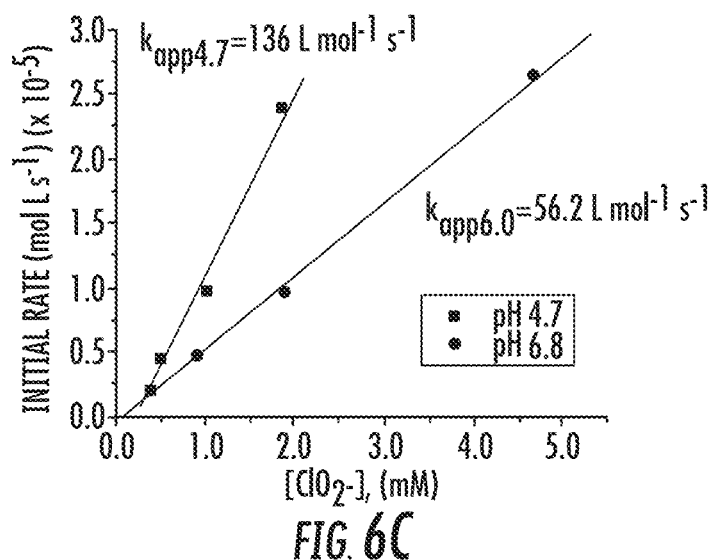

Referring to FIGS. 6A-6C, the MnTM-2,3-PyPz catalyst was characterized. The UV-Vis spectra of MnTM2,3PyPz shows the characteristic porphyrazine Soret at 390 and Q-bands of intensity equal to the Soret. Normally these Q-bands are reported in the range 600-700 nm, but here we see 566 nm. The 800 nm absorbance is not found in Pz freebases, but similar absorbances have been reported for metallated Pz. Reactions of $ClO_2^-$ with Mn(III)TM-2,3-PyPz were studied using UV-vis spectroscopy and rapid mixing kinetic techniques. Solutions of Mn(III)TDMImP and $ClO_2^-$ were prepared in buffered solutions and mixed 1:1. Final concentrations for reactions were obtained by dividing the initial concentrations by two. Thirty minutes elapsed between temperature setting and experiment to allow the cell holder and mixing accessory to equilibrate to the set temperature. Aliquots of $ClO_2^-$ and Mn(II)TM-2,3-PyPz stock solutions were added to 10 mL 100 mM buffer in a test tube with side arm and immediately sealed using a rubber stopper outfitted with a fitted sparging tube. The reaction mixture was sparged with He during the course of the reaction through another fritted bubbler into a second test tube containing 20-40 mL of aqueous 200 mM KI for determination of total chlorine dioxide produced.

Alternatively, Mn(II)TH-2,3-PyPz was supported on montmorillonite KSF by adding 1 mL of 2.5 mM Mn(II)TH-2,3-PyPz to a stirring, aqueous suspension of montmorillonite (~200 mg/mL). Immediately the clay adsorbed the cationic porphyrin, and the supernatant had no color when the porphyrin-clay suspension was allowed to settle.

Using the clay-bound Mn(II)TH-2,3-PyPz, catalyst-free solutions of $ClO_2$ could be prepared by stirring unbuffered solutions of $NaClO_2$ with aliquots of the Mn(II)TH-2,3-PyPz/clay slurry in an open reaction vial, followed by filtration through Celite/glass wool in a Pasteur pipet to remove the catalyst. Using 2 mg of the monified clay, a 5.5 mM solution of $NaClO_2$ produced 1 mM $ClO_2$ solution in 15 minutes (by UV-Vis analysis). With larger amounts of the Mn(II)TH-2,3-PyPz/clay (10-100 mg), the reaction was complete in less than 10 minutes, producing a catalyst-free 2.1 mM $ClO_2$ solution from a 9.5 mM solution of $NaClO_2$.

Figure 11A:
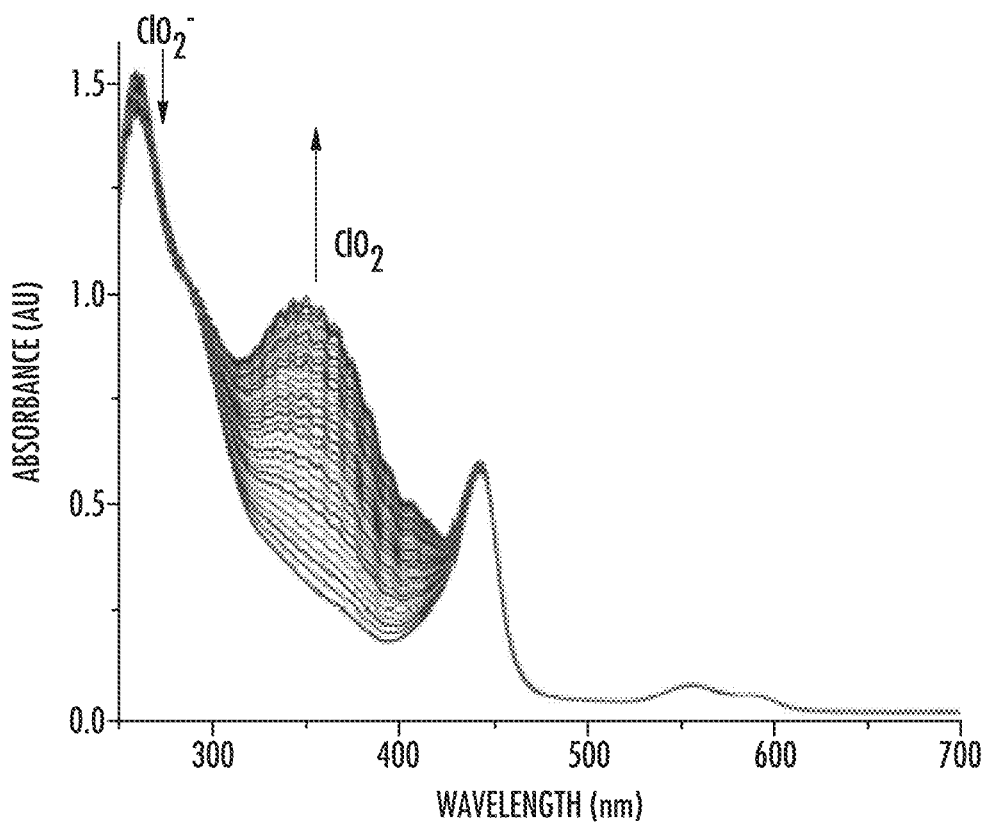
FIGS. 11A-B illustrate (A) Rapid appearance of $ClO_2$ (359 nm) from the MnTDMImP-catalyzed decomposition of $ClO_2^-$ (10 mM) at pH 6.8 with 0.1 mol % catalyst (445 nm) showing first 30 s of reaction, 1 scan/s; and (B) Similar reaction with MnTM23PyPz (9 mM sodium chlorite, 10 uM MnTM23PyPz, pH 4.7 100 mM acetate buffer, showing the first 30 s of reaction, 1 scan/s).
Figure 11B:
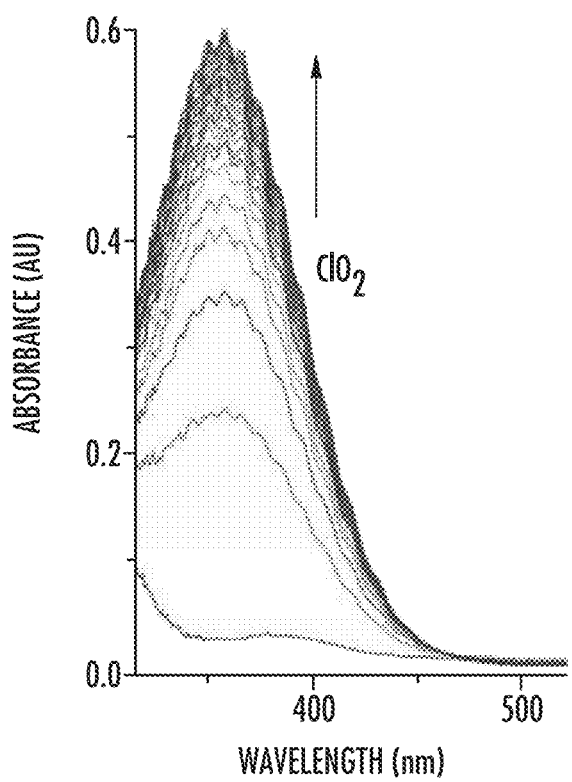

Referring to FIGS. 11A and 11B, FIG. 11A illustrates the rapid appearance of $ClO_2$ (359 nm) from the MnTDMImP-catalyzed decomposition of $ClO_2^-$ (10 mM) at pH 6.8 with 0.1 mol % catalyst (445 nm) showing first 30 s of reaction, 1 scan/s. FIG. 11B illustrates a similar reaction with MnTM23PyPz (9 mM sodium chlorite, 10 uM MnTM23PyPz, pH 4.7 100 mM acetate buffer, showing the first 30 s of reaction, 1 scan/s).

The electron-deficient manganese(III) tetra-(N,N-dimethyl)imidazolium porphyrin (MnTDMImP), tetra-(N,N-dimethyl)benzimidazolium (MnTDMBImP) porphyrin and manganese(III) tetramethyl-2,3-pyridinium porphyrazine (MnTM23PyPz) were found to be the most efficient catalysts for the conversion of chlorite to chlorine dioxide at neutral pH and with mild conditions. The more typical manganese tetra-4-N-methylpyridiumporphyrin (Mn-4-TMPyP) was useful in the process, but less effective than Mn-4-TMPyP. Rates for the best catalysts were in the range of 0.24-32 TO/s with MnTM23PyPz showing the fastest turnover. The kinetics of reactions of the various $ClO_x$ species (e.g., chlorite ion, hypochlorous acid and chlorine dioxide) with authentic oxomanganese(IV) and dioxomanganese(V) MnTDMImP intermediates were studied with stopped-flow spectroscopic methods, thus allowing independent confirmation of the individual steps in this catalysis. The proposed mechanism indicates a dual role for chlorite ion as both an oxidant and the substrate precursor to $ClO_2$. Rate-limiting oxidation of the manganese(III) catalyst by chlorite ion via oxygen atom transfer is proposed to afford a trans-dioxomanganese(V) intermediate. Both trans-dioxomanganese(V)TDMImP and oxoaqua-manganese(IV)TDMImP oxidize chlorite ion by 1-electron, generating the product chlorine dioxide with bimolecular rate constants of $6.30 \times 10^3$ $M^{-1}$ $s^{-1}$ and $3.13 \times 10^3$ $M^{-1}$ $s^{-1}$, respectively, at pH 6.8. Chlorine dioxide was able to oxidize manganese(II) TDMImP to oxomanganese(IV) at a similar rate, establishing a redox steady-state equilibrium under turnover conditions. Another important oxygen transfer reaction controlling this process is the rapid, reversible oxygen atom transfer between dioxoMn(V)TDMImP and chloride ion. The measured equilibrium constant for this reaction ($K_{eq}$=2.2 at pH 5.1) afforded a value for the oxoMn(V)/Mn(III) redox couple under catalytic conditions (E'=1.35 V vs NHE). In subsequent processes, chlorine dioxide reacts with both oxomanganese(V) and oxomanganese(IV) TDMImP to afford chlorate ion. Kinetic simulations of the proposed mechanism using experimentally measured rate constants were in agreement with observed chlorine dioxide growth and decay curves, measured chlorate yields, and the oxoMn(IV)/Mn(III) redox potential (1.03 V vs NHE). This acid-free catalysis could form the basis for a new process to make $ClO_2$.

Catalytic Generation of $ClO_2$ from $ClO_2^-$

The cationic, water-soluble manganese porphyrins (shown below) and a similar porphyrazine complex (also shown below) catalyzed the rapid production of chlorine dioxide from chlorite ion under mild conditions. The evolved $ClO_2$ could be monitored from the appearance of the characteristic chromophore at 359 nm (FIGS. 11A-11B). During turnover, the visible spectra of the $Mn^{III}$ catalysts remained largely unchanged, demonstrating the resistance of the catalyst to bleaching as well as providing mechanistic insight. The initial turnover rates for each of the studied catalysts are reported in 2. below. Extremely high activity (32 TO/s) was observed for the manganese(III) porphyrazine, MnTM23PyPz.

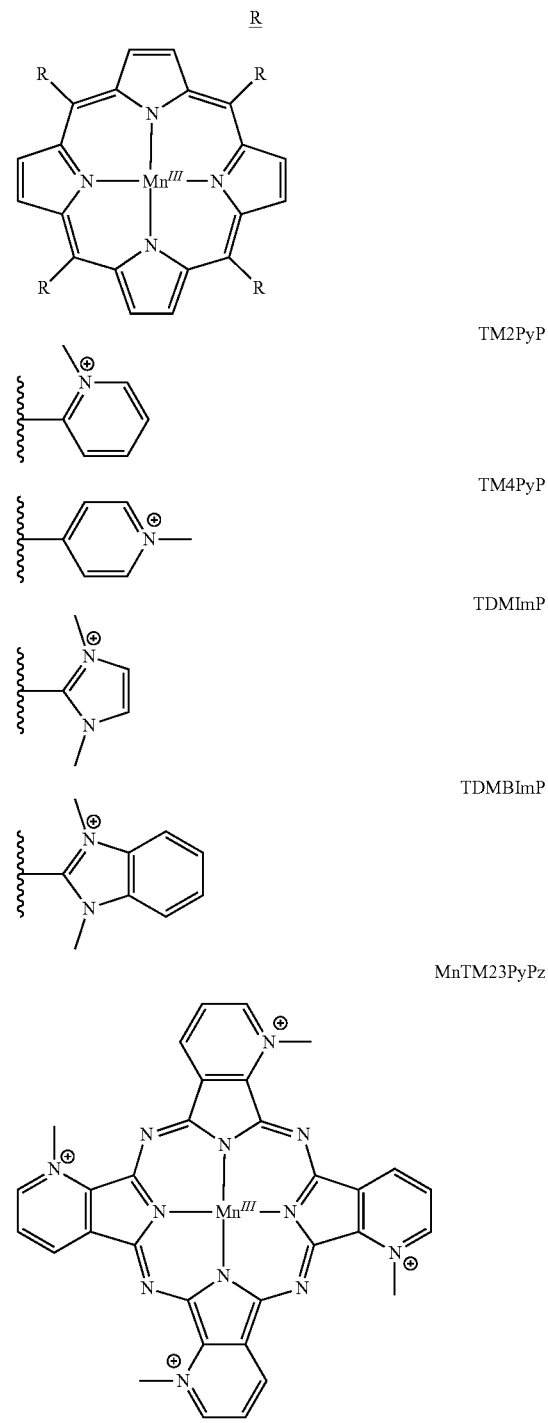

Acronyms

TM2PyP, tetra-(N-methyl)-2-pyridyl porphyrin; TM4PyP, tetra(N-methyl)-4-pyridyl porphyrin; TDMImP, tetra-(N,N-dimethyl)-imidazolium porphyrin; TDMBImP, tetra(N,N-dimethyl)-benzimidazolium porphyrin Manganese porphyrins and porphyrazine studied as catalysts.

TABLE 2

| Catalyst | initial turnover frequency ($s^{-1}$) | mol % cat. |
|---|---|---|
| MnTM4PyP* | 0.01 | 0.25 |
| MnTM2PyP* | 0.24 | 0.25 |
| MnTDMImP* | 0.40 | 0.25 |
| MnTDMBImP* | 0.48 | 0.50 |
| MnTM23PyPz** | 32.0 | 0.27 |

*pH 6.8 50 mM phosphate buffer, T = 25° C., 2.0 mM $NaClO_2$
**pH 4.5 50 mM acetate buffer, T = 25° C., 1.8 mM $NaClO_2$ The appearance of $ClO_2$ using MnTDMImP was studied in 100 mM acetate buffer (pH 4.7 and 5.7) and 100 mM phosphate buffer (pH 6.8). Initial turnover frequencies observed under these conditions at 25° C. for 2 mM $ClO_2^-$ and 10 µM $Mn^{III}$TDMImP were 1.00, 1.03, and 0.42 at pH 4.7, 5.7, and 6.8, respectively. However, the turnover frequency was influenced more by buffer composition than by pH. Increasing buffer concentration and ionic strength (with added sodium perchlorate) was found to inhibit the MnTDMImP-catalyzed reaction by a factor of 5 in the range 5 mM-100 mM while at a constant buffer concentration, the turnover frequency did not change from pH 5.9 to 7.01.

When $ClO_2^-$ was rapidly mixed with $Mn^{III}$TDMImP at 25° C., the spectroscopically-observed concentration of $ClO_2$ produced rose quickly and reached a plateau within 3 mins. The product $ClO_2$ absorbance subsequently decayed in a slower process over the course of about 15 mins. The maximum $ClO_2$ concentration was not affected by temperature (2.0 mM $ClO_2$, 10 µM $Mn^{III}$TDMImP, 100 mM pH 6.8 phosphate buffer), although the reaction rate increased markedly from 5 to 35° C.

Reduction of oxo$Mn^V$ and oxo$Mn^{IV}$TDMImP by $ClO_2^-$

The reactions of both oxo$Mn^V$TDMImP and oxo$Mn^{IV}$TDMImP with $ClO_2^-$ were studied by double-mixing, stopped-flow spectroscopy. In the first push, authentic oxo$Mn^V$ or oxo$Mn^{IV}$ was generated by mixing $Mn^{III}$TDMImP with 1 equiv of oxone or tBuOOH, respectively, in 10 mM pH 8.0 phosphate buffer. In the second push, oxo$Mn^V$ or oxo$Mn^V$ was mixed with an excess of $ClO_2^-$ in 100 mM pH 4.7 acetate or pH 6.8 phosphate buffer. This "pH jump" experiment permitted observation of the reaction between each of the high-valent manganese species with $ClO_2^-$ at lower pH values.

The decay of oxo$Mn^V$ (as measured by the characteristic Soret absorbance at 425 nm) was pH-dependant and followed pseudo-first order kinetics when mixed with an excess of $ClO_2^-$. This decay was fit to a modeled exponential decay curve in order to obtain the observed pseudo-first order rate constant ($k_{obs}$), which was plotted as a function of [$ClO_2^-$]. The apparent second-order rate constants ($k_{app}$) calculated from the slope of $k_{obs}$ vs. [$ClO_2^-$] are $6.8 \times 10^5$ and $6.3 \times 10^3$ $M^{-1}$ $s^{-1}$ at pH 4.7 and 6.8, respectively.

At pH 4.7, the 1-electron reduction of oxo$Mn^V$ by $ClO_2^-$ was fast and allowed the direct observation of a reduced oxo$Mn^{IV}$TDMImP catalyst with a single isosbestic point between a Soret bands at 437 nm (5 µM oxo$Mn^V$TDMImP and 125 µM $ClO_2^-$ in 100 mM pH 4.7 acetate buffer over 0.3 s). By contrast, at pH 6.8 the reaction of oxo$Mn^V$ with $ClO_2^-$ afforded $Mn^{III}$ (10 µM oxo$Mn^V$TDMImP and 1.0 mM $ClO_2^-$ in 100 mM pH 6.8 phosphate buffer over 3 s). The presence of two time-separated isosbestic points (436 nm and 432 nm) during this reaction demonstrated the intermediacy of oxo$Mn^{IV}$ in the reaction between oxo$Mn^V$ and $ClO_2^-$. Under these conditions, the apparent second-order rate constant $k_{app}$ was determined by first obtaining a pseudo-first order rate constant ($k_{obs}$) during the first phase of the reaction (where only the 436 nm isosbestic was observed).

The reaction between oxo$Mn^{IV}$ and an excess of $ClO_2^-$ was similarly found to result in a pseudo-first order decay of oxo$Mn^{IV}$ to $Mn^{III}$ (as measured by the characteristic Soret absorbance of oxo$Mn^{IV}$ at 422 nm) at pH 4.7 and 6.8 (10 µM oxoMnIVTDMImP and 1.0 M $ClO_2^-$ in 100 mM pH 4.7 acetate buffer over 3 s and 10 µM oxoMnIVTDMImP and 1.0 M $ClO_2^-$ in 100 mM pH 6.8 phosphate buffer over 1.5 s). A single isosbestic point was observed at 433 nm between the Soret bands of oxo$Mn^{IV}$ and $Mn^{III}$. The apparent second-order rate constants measured for the reduction of oxo$Mn^{IV}$ by $ClO_2^-$ are $6.0 \times 10^3$ and $3.1 \times 10^3$ $M^{-1}$ $s^{-1}$ at pH 4.7 and 6.8, respectively.

Measurement of $k_{app}$ for Oxo-Transfer Between HOCl and $Mn^{III}$

The reaction between hypochlorous acid (HOCl) and $Mn^{III}$TDMImP was studied by single-mixing stopped-flow spectrometry. At pH 6.8, the reaction resulted in complete formation of oxo$Mn^V$ in <100 ms ($Mn^{III}$TDMImP with HOCl at pH 6.8, 5.1, or 4.7; buffer conditions—pH 6.8, 100 mM phosphate buffer; pH 4.7 and 5.1, 100 mM acetate buffer; reaction conditions—(a) 10 µM MnIII, 5 equiv HOCl; (b) 5 µM $Mn^{III}$, 20 equiv HOCl; (c) 5 µM $Mn^{III}$, 50 equiv HOCl). An apparent second-order rate constant for the reaction was determined by measuring $k_{obs}$ of oxo$Mn^V$ appearance (425 nm) as a function of [HOCl]. The calculated rate constant ($k_4$) at pH 6.8 was $1.7 \times 10^6$ $M^{-1}$ $s^{-1}$. An initial-rate analysis of oxo$Mn^V$ formation gave a slower rate constant of $1.47 \times 10^5$ $M^{-1}$ $s^{-1}$.

At pH 4.7, complete formation of oxo$Mn^V$ could not be elicited with even a 50-fold excess of HOCl. Nevertheless, the apparent second-order rate constant ($k_4 = 6.6 \times 10^4$ $M^{-1}$ $s^{-1}$) under these conditions was calculated from a plot of $k_{obs}$ for the decrease in $Mn^{III}$ absorbance (444 nm) versus [HOCl]. A similar analysis using the method of initial rates provided a lower calculated $k_4 = 4.22 \times 10^3$ $M^{-1}$ $s^{-1}$. After a quick reaction time (<0.1 s at pH 4.7), the concentrations of $Mn^{III}$ and oxo$Mn^V$ reached an apparent steady-state equilibrium. This steady-state observation can be better demonstrated at slightly less-acidic conditions of pH 5.1.

Reaction of $ClO_2$ with $Mn^{III}$TDMImP

In order to account for the observed decay of $ClO_2$ (FIG. 3), the reaction of $ClO_2$ with $Mn^{III}$TDMImP was investigated. The $ClO_2$ absorbance at 360 nm quickly disappeared in the presence of $Mn^{III}$ TDMImP at pH 6.8, but not pH 4.7 (Initial [$ClO_2$] was 0.53 mM at pH 4.7 and 0.59 mM at pH 6.8). In both cases, the only porphyrin oxidation state observed in solution was $Mn^{III}$.

Electron Transfer Between oxo$Mn^{IV}$, oxo$Mn^V$ and $ClO_2$

Stopped-flow techniques were again used to observe how high-valent species oxo$Mn^V$TDMImP and oxo$Mn^{IV}$TDMImP react with $ClO_2$. Both oxo$Mn^V$ and oxo$Mn^{IV}$ reacted with $ClO_2$ via 1-electron transfers. Although oxo$Mn^{IV}$ did not build up in the reaction of oxo$Mn^V$ with $ClO_2$, the observation of two, time-separated isosbestic points indicates the intermediacy of oxo$Mn^{IV}$ in the reaction. The product of 1-electron oxidation of $ClO_2$ is formally a chlorine(V) species, presumably chlorate ($ClO_3^-$). The apparent second-order rate constants ($k_{app}$) for the reduction of oxoMn$^V$ by $ClO_2$ were $1.6 \times 10^4$ M$^{-1}$ s$^{-1}$ and $2.2 \times 10^4$ M$^{-1}$ s$^{-1}$ at pH 6.8 and 4.7, respectively. Calculated $k_{app}$ for the reduction of oxoMn$^{IV}$ by $ClO_2$ are $1.2 \times 10^4$ M$^{-1}$ s$^{-1}$ and $7.9 \times 10^3$ M$^{-1}$ s$^{-1}$ at pH 6.8 and 4.7, respectively.

$ClO_3^-$ Determination by HPLC

The observation that $ClO_2$ itself acted as a 1-electron reductant of oxoMn$^{IV}$TDMImP and oxoMn$^V$TDMImP suggests that some chlorine(V) species, presumably $ClO_3^-$, was produced. An indirect UV-detection HPLC method was therefore employed to confirm and quantify the presence of $ClO_3^-$ in reaction mixtures of either $ClO_2^-$ or $ClO_2$ with Mn$^{III}$TDMImP (Table 3). Buffer, catalyst, $ClO_2^-$, and $ClO_2$ stock solutions were free of $ClO_3^-$ prior to reaction. A measured amount of either $ClO_2^-$ or $ClO_2$ was added to solutions of MnTDMImP and stirred for ca. 1 h before being analyzed. Because the excess buffer anions co-eluted with chloride anion, the quantification of chloride produced by the catalytic decomposition of $ClO_2^-$ could not be accomplished.

TABLE 3

| Added substrate | $[ClO_3^-]_{obsd}$ (mM) | $[ClO_3^-]_{pred}$ (mM) |
| --- | --- | --- |
| 1 mM $ClO_2$ | 0.7 | 0.8 |
| 1 mM $ClO_2^-$ | 0.6 | 0.7 |
| 2 mM $ClO_2^-$ | 1.7 | 1.4 |

Table 3 shows the measured concentrations of $ClO_3^-$ produced ($[ClO_3^-]_{obsd}$) from the reaction of 10 μM Mn$^{III}$TDMImP with a given amount of substrate ($ClO_2$ or $ClO_2^-$) at pH 6.8. Also shown are the $ClO_3^-$ concentrations predicted ($[ClO_3^-]_{pred}$) by a kinetic model of the proposed mechanism (vida infra) given the same substrate/catalyst starting conditions.

Scheme 1, below, was proposed for the reaction mechanism.

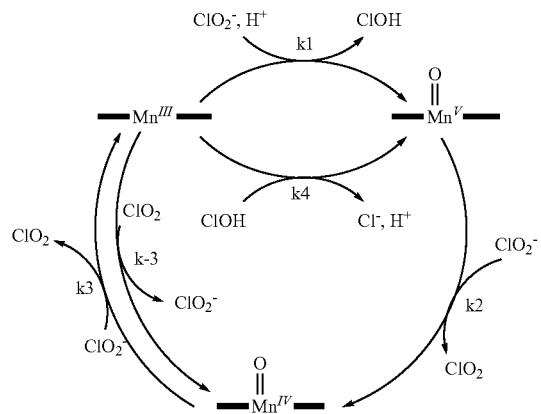

Scheme 1. Proposed mechanism for $ClO_2$ evolution from $ClO_2^-$.

The key initiating step in this catalytic cycle was suggested to be oxygen atom transfer from chlorite to the Mn$^{III}$ catalyst to form trans-dioxoMn$^V$TDMImP. The thermodynamic driving force for oxo-transfer from chlorite ion is only slightly less than that of hypobromite ion ($BrO^-$) ($\Delta\Delta G° = +16.7$ kJ mol$^{-1}$). Hypobromite is a very facile oxo-transfer agent in its reaction with Mn$^{III}$ porphyrins, with a rate constant for oxo-transfer from HOBr to Mn$^{III}$TD-MImP $\sim 10^5$ M$^{-1}$ s$^{-1}$ at neutral pH. For the reaction with chlorite ion, the fact that the Mn$^{III}$ oxidation state of the catalyst persisted during turnover requires that any change in the porphyrin oxidation state from Mn$^{III}$ be slow relative to Mn$^{III}$-forming reactions. Therefore, it was concluded that the oxidation of Mn$^{III}$ by $ClO_2^-$ must be the rate-determining step of the overall cycle. Accordingly, a slower 2-electron oxidation of Mn$^{III}$ by $ClO_2^-$, generating HOClO and trans-dioxoMn$^V$ is consistent with these observations. Interestingly, the pH-independence of the turnover rate implies that the oxygen transfer step to afford the Mn$^V$ species is pH-independent and occurs at about the same rate as the analogous heterolysis of HOO-Mn$^{III}$TDMImP, which also affords Mn$^V$.

The evolved $ClO_2$ can be efficiently removed from the reaction vessel via simple sparging or air stripping during turnover. Further, the catalysts are active on a solid support, suggesting their use in a flow system, a cartridge or a trickle-bed reactor. Methods for greatly enhancing the rate of $ClO_2$-generation and the reduction of impurities such as chlorine may be achieved by ligand tuning, or by using externally-added oxidants to overcome the relatively slow, chlorite-initiated oxo-transfer step.

Experimental

Reagents

Sodium chloride, sodium chlorate, t-butyl hydroperoxide (70% aqueous solution), and Oxone were purchased from Aldrich and used as received. Sodium chlorite was obtained from Aldrich as >80% technical grade and recrystallized twice from ethanol/water (>95% final). All oxidant stock solutions were prepared fresh daily and standardized by iodometeric titration before use. Dilute (0.5-10.0 mM) chlorite solutions were standardized spectrophotometrically ($\varepsilon_{260}$ nm=154 cm$^{-1}$ M$^{-1}$). Buffers were prepared fresh each day using either acetic acid/sodium acetate (pH=4.7, 5.7) or potassium phosphate (monobasic)/potassium phosphate (dibasic) (pH=6.8, 8.0) and pH-adjusting no more than 0.1 units using perchloric acid or sodium hydroxide. $ClO_2$ was prepared from $ClO_2$ using a previously reported procedure. Briefly, a 2.5% w/w solution of $NaClO_2$ was acidified with sulfuric acid under an argon flow in the dark. The evolved gas was carried by the argon flow through a gas scrubbing tower containing a 2.5% w/w solution of $NaClO_2$ and bubbled through deionized water in a chilled amber bottle. Aliquots of the resulting solution were frozen at −30° C. for prolonged storage. The concentration of $ClO_2$ was checked immediately prior to use ($\varepsilon_{359\ nm}$=1230 cm$^{-1}$ M$^{-1}$). Leftover $ClO_2$ from all experiments was neutralized with sodium iodide before being disposed of in general waste. Mn$^{III}$TDMImP was synthesized as the chloride salt using reported procedures. MnTM2PyP and MnTM4PyP were purchased from Mid Century and purified by double precipitation. MnTM23PyPz was prepared following the method of Wöhrle. Briefly, manganese diacetate (170 mg) and pyridine-2,3-dicarbonitrile (500 mg) were heated in an unsealed reaction tube to 200° C. with mechanical stirring for 4 hours. The deep blue solid product (a mixture of isomers) was washed with acetone, isolated by filtration, suspended in 50 mL DMF, and tetra-methylated using excess dimethyl sulfate at 120° C. for 12 hours. Product was precipitated with acetone and purified by double precipitation.

Instrumentation

UV-Vis spectroscopic measurements were taken using a Hewlett-Packard 8453 diode array spectrophotometer equipped with a temperature-controlled cell housing, VWR 1140 thermostat bath and a Hi-Tech SFA Rapid Kinetics Accessory. Stopped-flow experiments for fast reactions were carried out using a Hi-Tech SF-61 double-mixing instrument with a 1 cm path length equipped with an ISOTEMP 1016 S thermostat bath. Ion chromatography was accomplished with an HPLC system consisting of a Waters 600 controller, Hamilton PRP X-100 column, and Waters 996 photodiode array detector.

Stopped-Flow Experiments

Reactions of $ClO_2^-$ with $Mn^{III}$ porphyrins were studied using traditional UV-vis and rapid mixing techniques. Solutions of catalyst and $ClO_2^-$ were prepared in buffered solutions and mixed 1:1. All rate calculations were based on final concentrations resulting from this dilution. The oxidations of $ClO_2^-$ and $ClO_2$ by oxoMn$^V$TDMImP and oxoMn$^{IV}$TDMImP were studied in double mixing mode using diode array detection. Solutions of Mn$^{III}$TDMImP and oxidant (oxone, tBuOOH) were prepared in weak pH=8.0 phosphate buffer (10 mM) and mixed 1:1 in a first push. After a short aging time to ensure complete conversion to the high-valent species (2-150 s, fine tuned for each experiment), the porphyrin solution was mixed 1:1 with the substrate ($ClO_2^-$ or $ClO_2$) prepared in a higher strength buffer (100 mM) at the pH to be studied (4.7 or 6.8). All concentrations used in subsequent rate calculations accounted for the 4-fold and two-fold dilutions inherent to the double-mixing technique. Each reaction was run in duplicate or triplicate at T=25° C. Averaging of the runs and analysis of the data was accomplished using the KinetAsyst 3 software package. Kinetic simulations of the overall mechanism were performed with the Berkeley-Madonna software package.

Ion Chromatography Experiments

Aliquots of $ClO_2^-$ or $ClO_2$ solutions were added to buffered solutions of Mn$^{III}$TDMImP under mechanical stirring at ambient temperatures. $ClO_3^-$ was quantified using an indirect ion chromatography method. In brief, an aqueous solution of 4-aminosalicylic acid (4 mM) was pH adjusted to pH=6.0 and employed as the mobile phase. Reaction samples were injected directly without any modification. The eluent was monitored at 320 nm, and a decrease in absorbance was observed as anions were eluted. Concentration of analyte was calculated directly from total area of the peak using a concentration curve prepared daily using prepared standards.

Example 8—Exemplary Iron Catalysts

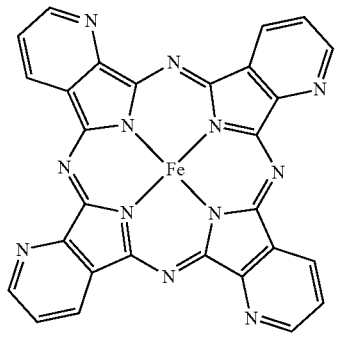

Fe-2,3-PyPz

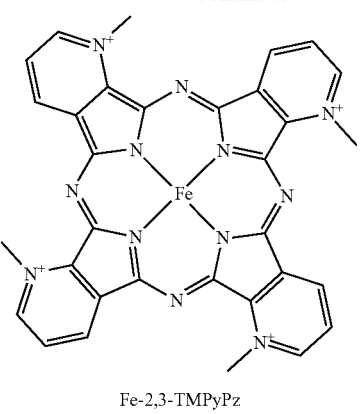

Fe-2,3-TMPyPz

The catalyst Fe-2,3-PyPz was prepared by the method of Hanack (Chem. Ber. 121, 1225-1230 (1988). Alkylation of this compound to prepare the Fe-2,3-TMPyPz catalyst was performed in analogy to the method of Wöhrle (J. Chem. Soc. Perkin Trans. II, 1985, 1171.

Improved Synthesis of Manganese and Iron Porphyrazine Catalysts

Synthesis of Mn23PyPz

The original synthesis of tetrapyridinoporphyrazines like Mn23PyPz required the expensive pyridine-2,3-dicarbonitrile as a precursor. (Scheme 2) This procedure involved adding 4 mmol of pyridine-2,3-dicarbonitrile and 1 mmol of manganese acetate to a microwave vial with a stir bar, heating the mixture to 200° C. in a silicone oil bath, and stirring the now liquid and dark green mixture for 4 hours. The mixture was then cooled to room temperature and then crushed and washed with excess acetone. See U.S. Patent Application Publication No. 2013/0209573, which is the publication of U.S. application Ser. No. 13/818,575, filed Aug. 19, 2011, and is incorporated herein by reference as if fully set forth. When equimolar amounts of $MnCl_2$ were used in place of manganese acetate, Mn23PyPz was obtained in 89% yield by this method.

Scheme 2: Synthesis of manganese (II) tetra-2,3-pyridinoporphyrazine (Mn23PyPz)

MnCl$_2$

+

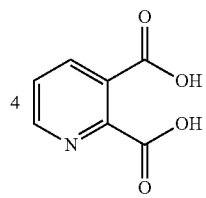

2,3-pyridinedicarboxylic acid

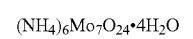

$(NH_4)_6Mo_7O_{24} \cdot 4H_2O$

+

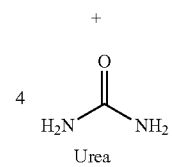

Urea

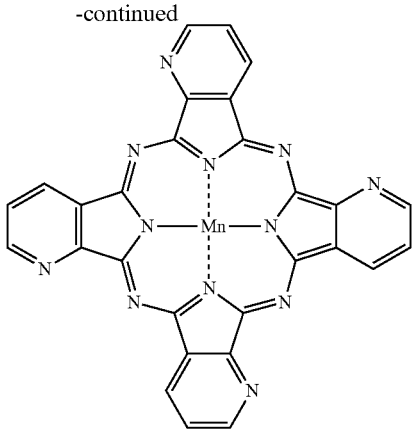

Manganese (II) tetra-2,3-pyridinoporphyrazine

A second method of synthesizing Mn23PyPz was also derived from the aforementioned synthesis of CuPc described by Sharma et al. (Scheme 3) (Sharma, R. K.; Sharma, C.; Sidhwani, I. T. Solventless and One-Pot Synthesis of Cu(II) Phthalocyanine Complex: A Green Chemistry Experiment. *Journal of Chemical Education* 2011, 88, 86-87). In this method, phthalic anhydride is substituted with equimolar amounts of either 2,3-pyridinedicarboxylic anhydride or 2,3-pyridinecarboxylic acid. Mn23PyPz was obtained in 82% yield when using 2,3-pyridinedicarboxylic anhydride and 50-90% when using 2,3-pyridinedicarboxylic acid (Scheme 3).

Scheme 3: Synthesis of manganese (II) phthalocyanine (MnPc)

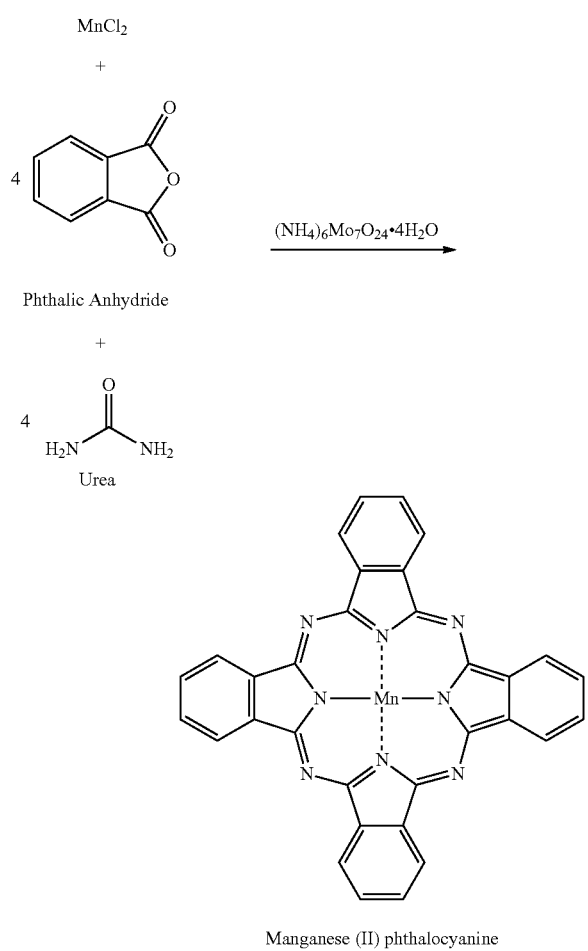

Manganese (II) phthalocyanine

Synthesis of Mn23PzPz

Mn23PzPz was synthesized using a procedure similar to the method employed to produce MnPc and Mn23PyPz. However, instead of using reagents phthalic anhydride or 2,3-pyridinedicarboxylic anhydride, equimolar amounts of 2,3-pyrazinedi-carboxylic anhydride were used instead (Scheme 4). Mn23PzPz was obtained in 72% yield by this method.

Scheme 4: Synthesis of manganese (II) tetra-2,3-pyrazinoporphyrazine (Mn23PzPz)

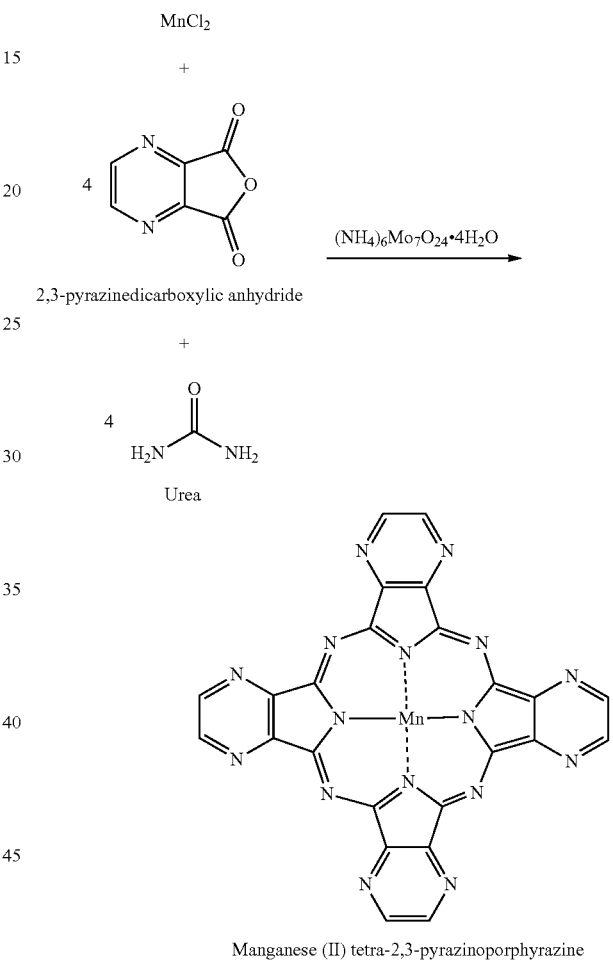

Manganese (II) tetra-2,3-pyrazinoporphyrazine

Methylation of Mn23PzPz was attempted by the same procedure used to methylate Mn23PyPz to form MnTM23PyPz, with this procedure described in the upcoming section detailing the synthesis method of FeTM23PyPz; however, no desired products were isolated. Dialkylations using 1,3-dibromopropane and 1,4-dibromobutane in an adapted alkylation procedure also failed to produce the desired products.

Synthesis of Fe23PyPz

Fe23PyPz was synthesized using the two previously described methods employed to synthesize Mn23PyPz, with $MnCl_2$ substituted for $FeCl_2$. When employing the synthesis method using pyridine-2,3-dicarbonitrile, Fe23PyPz was obtained in 91% yield. When using the method with 2,3-pyridinedicarboxylic anhydride, Fe23PyPz was obtained in 70-90% yield (Scheme 5).

Scheme 5: Synthesis of iron (II) tetra-2,3-pyridinoporphyrazine (Fe23PzPz)

FeCl₂

+

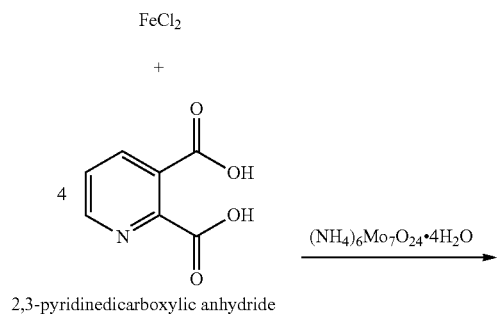

2,3-pyridinedicarboxylic anhydride (NH₄)₆Mo₇O₂₄·4H₂O →

+

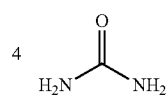

Urea

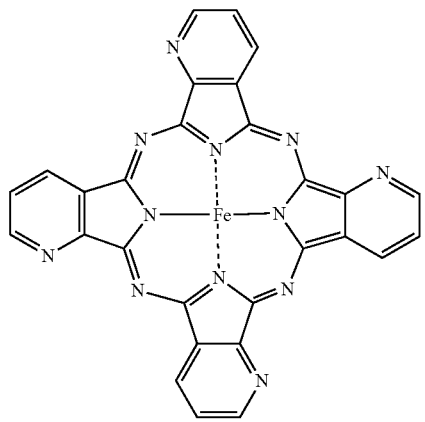

Iron (II) tetra-2,3-pyridinoporphyrazine

Synthesis of Fe23PzPz

Fe23PzPz was synthesized using the previously described method employed to synthesize Mn23PzPz, with MnCl₂ substituted for FeCl₂. This method produced Fe23PzPz in 70-90% yield (Scheme 6).

Scheme 6: Synthesis of iron (II) tetra-2,3-pyrazinoporphyrazine (Fe23PzPz)

FeCl₂

+

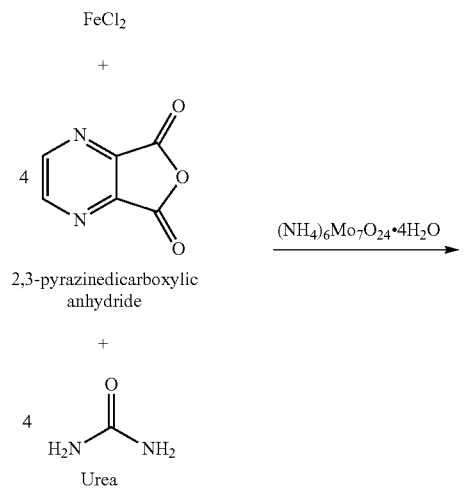

2,3-pyrazinedicarboxylic anhydride (NH₄)₆Mo₇O₂₄·4H₂O →

+

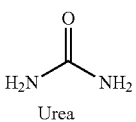

Urea

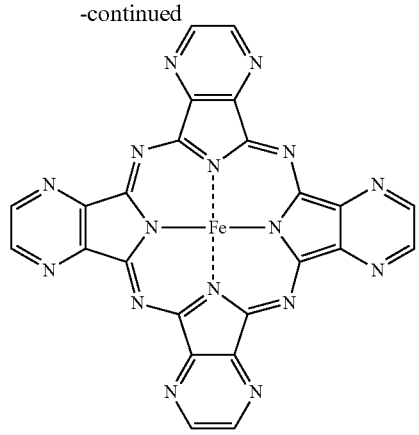

Iron (II) tetra-2,3-pyrazinoporphyrazine

Synthesis of Fe34PyPz

Fe34PyPz was synthesized using one of the previously described methods employed to synthesize Fe23PyPz, with 2,3-pyridinedicarboxylic anhydride replaced with 3,4-pyridinedicarboxylic acid (Scheme 7). Fe34PyPz was obtained in 60-85% yield with this method.

Scheme 7: Synthesis of iron (II) tetra-3,4-pyridinoporphyrazine (Fe34PyPz)

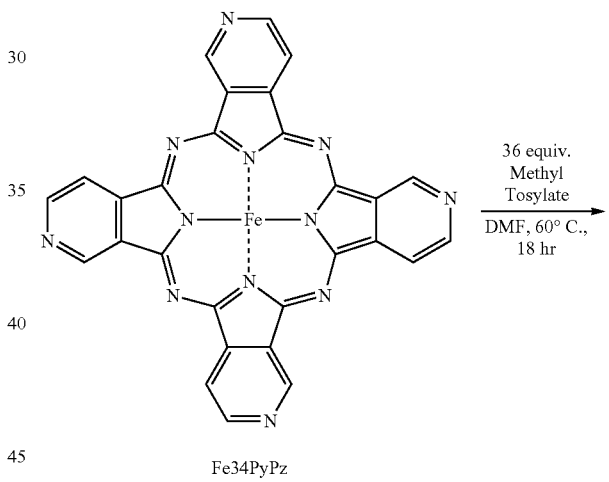

36 equiv. Methyl Tosylate
────────────→
DMF, 60° C., 18 hr

Fe34PyPz

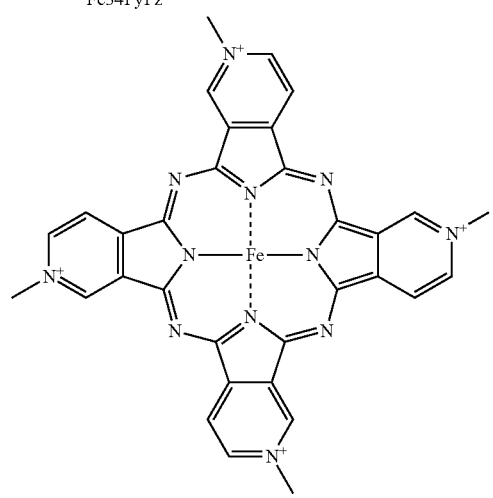

FeTM34PyPz

Synthesis of FeTM23PyPz

Fe23PyPz was methylated to form FeTM23PyPz (Scheme 2.2g) by the same procedure used to methylate Mn23PyPz to form MnTM23PyPz. For Mn23PyPz, on a small scale, 0.15 mmol of the Mn23PyPz were combined with excess methyl-p-toluenesulfonate (5.4 mmol) in 1.35 mL of dimethylformamide in a microwave vial with a stir bar. This mixture was heated to 60° C. in a silicone oil bath and stirred for 18 hours. At the end of this time, the mixture was cooled to room temperature and the liquid was added to 125 mL of chloroform in order to crash out the now methylated MnTM23PyPz. The product was filtered off and washed with acetone before being pulled through the filter with methanol as the first step of a double precipitation purification process. The methanol solution was then reduced in volume to approximately 5 mL by using a rotary evaporator before excess ammonium hexafluorophosphate was added to crash out MnTM23PyPz as the hexafluorophosphate salt. The product was then filtered off and washed with a 1:1 mixture of isopropanol and diethyl ether before being pulled through the filter with acetone. This solution was similarly reduced in volume to approximately 5 mL by using a rotary evaporator before excess tetrabutylammonium chloride was added to crash out MnTM23PyPz as the chloride salt. This final product was then filtered off and washed with additional acetone. This procedure could also be scaled up as necessary to produce more of the methylated product.

In order to produce FeTM23PyPz, this procedure was repeated with two modifications. First, Mn23PyPz was replaced with equimolar amounts of Fe23PyPz. Second, the acetone solvent used during the last step of the double precipitation process was replaced with acetonitrile since it was previously observed that the hexafluorophosphate salt of porphyrazines was more soluble in acetonitrile, thus allowing for greater yields to be achieved (Scheme 8).

Scheme 8: Synthesis of iron (II) tetra-N-2,3-pyridinoporphyrazine (FeTM23PyPz)

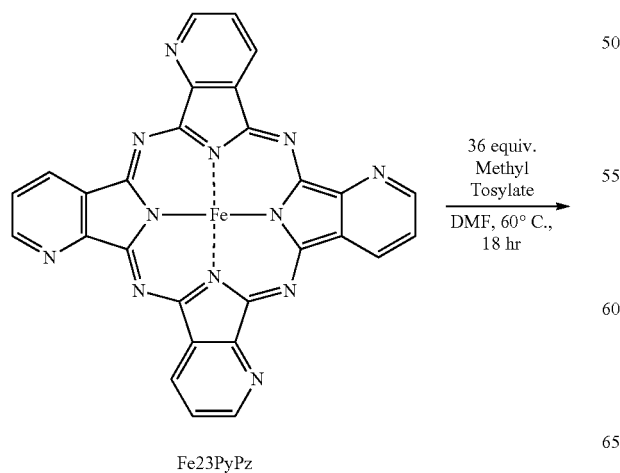

Fe23PyPz

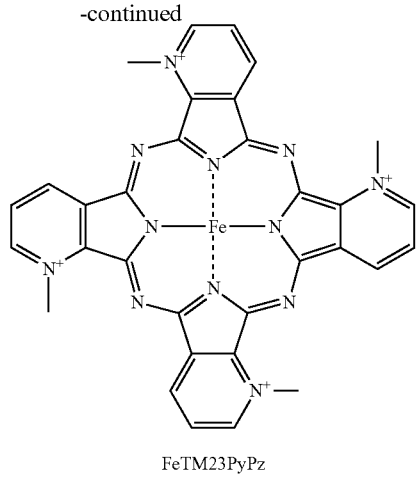

FeTM23PyPz

Synthesis of FeTM34PyPz

FeTM34PyPz was synthesized using the previously described methylation procedure employed to synthesize FeTM23PyPz from Fe23PyPz with the only change being the replacement of Fe23PyPz with Fe34PyPz (Scheme 9).

Scheme 9: Synthesis of iron (II) tetra-N-3,4-pyridinoporphyrazine (FeTM34PyPz)

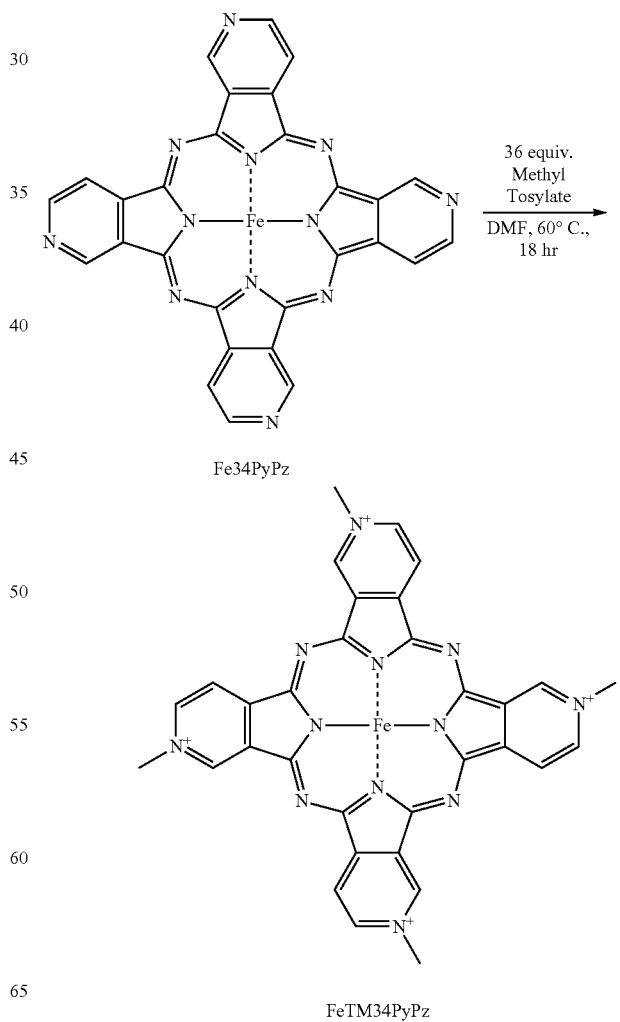

Fe34PyPz

FeTM34PyPz

Example 9

Improved Catalytic Performance of Fe23PyPz and Fe23TMPyPz, which had the structure:

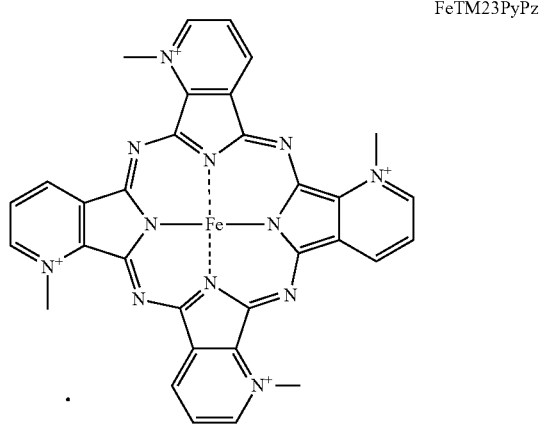

FeTM23PyPz

Figure 12:
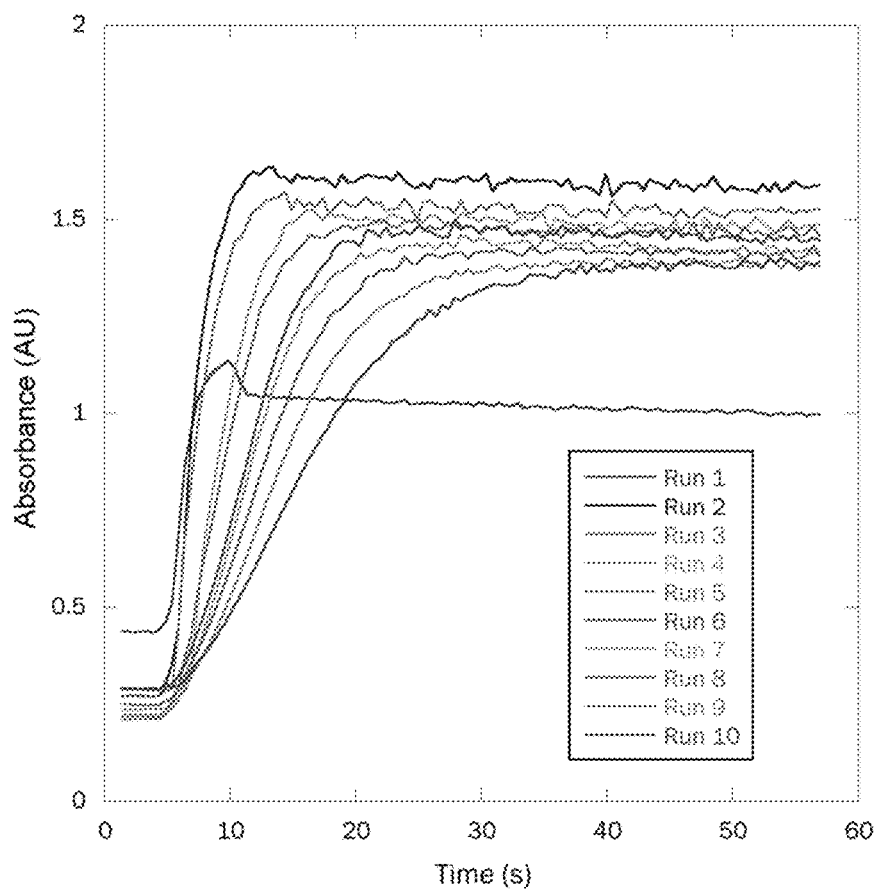
FIG. 12 illustrates measurement of the the rate of chlorine dioxide production was measured when catalyzed by FeTM23PyPz.

Referring to FIG. 12, the rate of chlorine dioxide production was measured. Absorbance at 359 nm ($ClO_2$) was measured during repeated reactions of 5 mM $ClO_2^-$ with 12.5 µM catalyst (FeTM23PyPz) in 100 mM acetate buffer (pH 2.8). Catalyst was reused ten times. Run 1 plateaus at approximately 1 AU. Runs 2 through 10 appear in descending order with Run 2 plateauing at approximately 1.7 AU and Run 10 at about 1.3 AU. The measured rate equals 12.0 $s^{-1}$.

After finding the highly reactive manganese porphyrazine, MnTM23PyPz, the water-soluble iron porphyrazine was investigated as a sustainable catalyst of rapid conversion of $ClO_2^-$ to $ClO_2$. Unlike its manganese counterpart, when multiple aliquots of $ClO_2^-$ are added to a reaction mixture of FeTM23PyPz, catalytic generation of $ClO_2$ decreases only slightly.

Initial catalyst concentrations for FeTM23PyPz as low as 0.125 µM are capable of fully consuming a 5 mM solution of $ClO_2^-$. In doing so, FeTM23PyPz is capable of on average 15,000 turnovers. The evolved $ClO_2$ is isolated in good yield when monitored by UV-Vis spectroscopy, with higher values expected when sparging the reaction vessel with helium gas or using vacuum during turnover. Fe23PyPz gave similar yields.

Example 10—Selectivity for $ClO_2$ Production from Sodium Chlorite Catalyzed by FeTM23PyPz*

Figure 13:
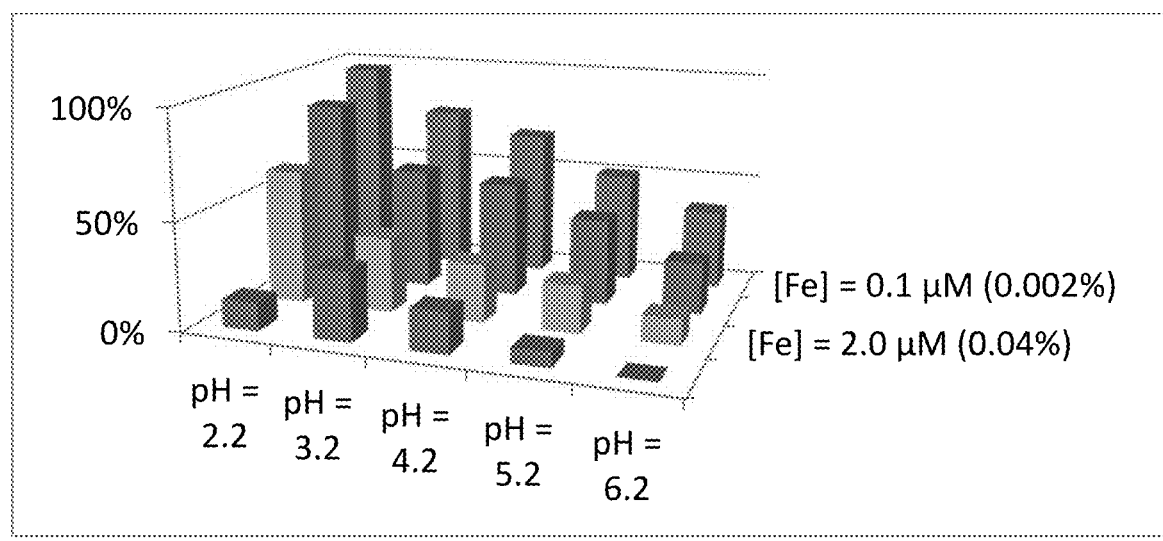
FIG. 13 reports results for analysis of selective $ClO_2$ production with different catalyst concentrations and pH.

Table 2 and FIG. 13 report results for analysis of selective $ClO_2$ production with different catalyst concentrations and pH.

TABLE 2

| Selectivity for $ClO_2$ production | pH = 2.2 | pH = 3.2 | pH = 4.2 | pH = 5.2 | pH = 6.2 | pH = 7.2 |
|---|---|---|---|---|---|---|
| [Fe] = 0.1 µM (0.002%) | 97% | 77% | 68% | 51% | 37% | 4% |
| [Fe] = 0.5 µM (0.01%) | 85% | 56% | 53% | 40% | 24% | 18% |
| [Fe] = 2.0 µM (0.04%) | 62% | 35% | 27% | 22% | 12% | 34% |
| [Fe] = 10 µM (0.20%) | 13% | 32% | 19% | 7% | 0% | 0% |

*There was negligible $ClO_2$ produced under these conditions in the absence of catalyst.

REFERENCES

1. ◯ Greenwood, Norman N.; Earnshaw, A. (1997), *Chemistry of the Elements* (2nd ed.), Oxford: Butterworth-Heinemann, pp. 844-849, ISBN 0080379419
2. ◯ Brockway LO (March 1933). "The Three-Electron Bond in Chlorine Dioxide". *Proc. Natl. Acad. Sci. U.S.A.* 19 (3): 303-7. PMID 16577512.
3. ◯ Pauling, Linus (1988). *General chemistry*. Mineola, N.Y.: Dover Publications, Inc. ISBN 0-486-65622-5.
4. ◯ Flesch, R.; Plenge, J.; Rühl, E. (2006). "Core-level excitation and fragmentation of chlorine dioxide". *International Journal of Mass Spectrometry* 249-250: 68-76. doi:10.1016/j.ijms.2005.12.046. edit
5. ◯ Derby, R. I.; Hutchinson, W. S. "Chlorine(IV) Oxide" Inorganic Syntheses, 1953, IV, 152-158.
6. ^ [a] [b] [c] Vogt, H.; Balej, J.; Bennett, J. E.; Wintzer, P.; Sheikh, S. A.; Gallone, P.; Vasudevan, S.; Pelin, K. (2010). "Chlorine Oxides and Chlorine Oxygen Acids". *Ullmann's Encyclopedia of Industrial Chemistry*. Wiley-VCH Verlag GmbH & Co. KGaA. doi:10.1002/14356007.a06_483.pub2. edit
7. ◯ White, George W.; Geo Clifford White (1999). *The handbook of chlorination and alternative disinfectants* (4th ed.). New York: John Wiley. ISBN 0-471-29207-9.
8. ◯ Thomas Wilson Swaddle (1997). *Inorganic chemistry: an industrial and environmental perspective*. Academic Press. pp. 198-199. ISBN 0 1.26785503.
9. ^ [a] [b] [c] [d] [e] [f] *EPA Guidance Manual*, chapter 4 *Chlorine dioxide*, US Environmental Protection Agency, http://www.epa.gov/OGWDW/mdbp/pdf/alter/chap_4.pdf, retrieved 2009-11-27
10. ^ [a] [b] [c] [d] Seymour Stanton Block (2001). *Disinfection, sterilization, and preservation* (5th ed.). Lippincott Williams & Wilkins. p. 215. ISBN 0683307401.
11. ◯ Sorlini, S.; Collivignarelli, C. (2005). "Trihalomethane formation during chemical oxidation with chlorine, chlorine dioxide and ozone of ten Italian natural waters". *Desalination* 176 (1-3): 103-111. doi: 10.1016/j.desal.2004.10.022. edit
12. ◯ Li J.; Yu Z.; Gao M. (1996). "A pilot study on trihalomethane formation in water treated by chlorine dioxide (translated from Chinese)". *Zhonghua Yu Fang Yi Xue Za Zhi* (*Chinese journal of preventive medicine*) 30 (1): 10-13. PMID 8758861.
13. ^ [a] [b] [c] C. J. Volk; R. Hofmann; C. Chauret; G. A. Gagnon; G. Ranger; R. C. Andrews (2002). "Implementation of chlorine dioxide disinfection: Effects of the treatment change on drinking water quality in a full-scale distribution system". *J. Environ. Eng. Sci.* 1: 323-330. doi: 10.11.39/SO2-026. http://pubs.nrc-cnrc.gc.ca/rp/rppdf/s02-026.pdf. Retrieved 2009 Nov. 27.
14. ◯ M. A. Pereira; L. H. Lin; J. M. Lippitt; S. L. Herren (1982). "Trihalomethanes as initiators and promoters of carcinogenesis". *Environ Health Perspect* 46: 151-156. PMID 7151756.
15. ◯ Andrews, L.; Key, A.; Martin, R.; Grodner, R.; Park, D. (2002). "Chlorine dioxide wash of shrimp and crawfish an alternative to aqueous chlorine". *Food Microbiology* 19 (4): 261-267. doi:10.1006/fmic.2002.0493. edit
16. ○ Zhe Zhang; Carole McCann; Janet E. Stout; Steve Piesczynski; Robert Hawks; Radisav Vidic; Victor L. Yu (2007). "*Safety and Efficacy of Chlorine Dioxide for Legionella control in a Hospital Water System*". *Infection Control and Hospital Epidemiology* 28 (8). http://www.legionella.org/ZhangICHE07.pdf. Retrieved 2009 Nov. 27.
17. ○ Ogata N, Shibata T (January 2008). "Protective effect of low-concentration chlorine dioxide gas against influenza. A virus infection". *J. Gen. Virol.* 89 (Pt 1): 60-7. doi:10.1.099/vir.0.83393-0. PMID 18089729. http://vir.sgmjournals.org/cgi/content/abstract/89/1/60?maxto show=&HITS=1.0&hits=1.0&RESULTFORMAT= &author1=ogata.+n&andorexactfulltext=and&searchid= 1&FIRSTINDEX=0&sortspec=relevance&resource- type=HWCIT.
18. ○ Zhang, Y. L.; Zheng, S. Y.; Zhi, Q. (2007). "*Air Disinfection with Chlorine Dioxide in Saps*". *Journal of Environment and Health* 24 (4): 245-246. http://www.csa.com/partners/viewrecord.php?requester=gs& collection=TRD& recid=0751921.3EN.
19. ○ "Anthrax spore decontamination using chlorine dioxide". United States Environmental Protection Agency. 2007. http://www.epa.gov/opp00001./factsheets/chemi- cals/chlorinedioxidefactsheet.htm. Retrieved 2009-11-27.
20. ○ Sy, Kaye V.; McWatters, Kay H.; Beuchat, Larry R. (2005). "*Efficacy of Gaseous Chlorine Dioxide as a Sanitizer for Killing Salmonella, Yeasts, and Molds on Blueberries, Strawberries, and Raspberries*". *Journal of Food Protection* (International Association for Food Protection) 68 (6): 1165-1175. PMID 15954703. http://www.ingentaconnect.com/content/iafp/jfp/2005/00000068/00000006/art00007.
21. ○ Frascella J.; Gilbert R. D.; Fernandez P.; Hendler J. (2000). "Efficacy of a chlorine dioxide-containing mouthrinse in oral malodor". *Compend Contin Educ Dent* 21 (3): 241-248. PMID 11199703.
22. Weitner, T.; Budimir, A.; Kos, I.; Batinic-Haberle, I.; Birus, M. *J. Chem. Soc., Dalton Trans.* 2010, 39, 11568-11576.
23. Budimir, A.; Smuc, T.; Weitner, T.; Batinic-Haberle, I.; Birus, M. *J. Coord. Chem.* 2010, 63, 2750-2765.
24. Batanic-Haberle, I.; Benov, L.; Spasojevic, I.; Fridovich, I. *J. Biol. Chem.* 1998, 273, 24521-24528. "The Ortho Effect Makes Manganese (III) Meso-Tetrakis-(N-Methylpyridinium-2-yl) Porphyrin a Powerful and Potentially Useful Superoxide Dismutase Mimic."
25. Spasojevicm, I.; Batinic-Haberle, I.; *Inorg. Chim. Acta* 2001, 317, 230-242. "Manganese (III) Complexes with Porphyrins and Related Compounds as Catalytic Scavengers of Superoxide."
26. Amaravathi, M.; Murthy, K. S. K.; Rao, M. K.; Reddy, B. S. *Tet. Lett.* 2001, 42, 6745-6747. "Synthesis of meso-Tetrakis(imidazol-5-yl) porphyrins."
27. Milgrom, L. R.; Dempsey, P. J. F.; Yahioglu, G. *Tet. Lett.* 1996, 52, 9877-9890. "5,10,15,20-Tetrakis(N-protected- imidazol-2-yl) porphyrins."
28. Sanchez-Migallon, A.; de la Hoz, A.; Begtrup, M.; Fernandez-Castano, C.; Foces-Foces, C.; Elguero, *J. Tet. Lett.* 1996, 10811-10822. "Porphyrins with Four Azole Substituents in meso Positions. Part 2. X-ray Crystal Structure of meso-tetrkis {1-[2-(trimethylsilyl)ethoxym- ethyl]pyrazol-5-yl}-porphyrin at 200K."
29. Wöhrle, D.; Gitzel, J.; Okura, I.; Aono, S. Photoredox Properties of tetra-2,3-pyridinoporphyrazines (29H,31H- tetrapyrido[2,3-b: 2',3'-g: 2",3"-l: 2''',3'''-q]porphyrazine); *J. Chem. Soc., Perkin Trans.* 2 1985, 1171-8.
30. Weitner, T.; Budimir, A.; Kos, I.; Batinic-Haberle, I.; Birus, M. *J. Chem. Soc., Dalton Trans.* 2010, 39, 11568-11576; c. Budimir, A.; Smuc, T.; Weitner, T.; Batinic-Haberle, I.; Birus, M. *J. Coord. Chem.* 2010, 63, 2750-2765.
31. Stuzhin, P. A.; Vagin, S. I.; Hanack, M. Synthesis and Spectral Properties of Bisaxially Coordinated (Octaphe- nyltetraazaporphyrinato)ruthenium (II) Complexes; *Inorg. Chem.* 1998, 37, 2655-2662.
32. Fitzgerald, J. P.; Kaul, B. B.; Yee, G. T. Vanadium [dicyanoperfluorostilbene]$_2$.yTHF: a molecule-based magnet with $T_c \approx 205$ K; *Chem. Commun.* 2000, 49-50.
33. Anderson, M. E.; Barrett, A. G. M.; Hoffman, B. M. Super-Charged Porphyrazines: Synthesis and Physical Properties of Octacationic Tetraazaporphyrins; *Inorg. Chem.* 1999, 38, 6143-51.
34. Reese, C. B.; Zhang, P. Z. Phosphotriester Approach to the Synthesis of Oligonucleotides: A Reappraisal; *J. Chem. Soc., Perkin Trans.* 1 1993, 2291-301.
35. C. Baird, M. C. Cann, *Environmental Chemistry*, 3rd ed., W.H. Freeman and Co., New York, 2005.
36. *Alternative Disinfectants and Oxidants Guidance Manual* (*EPA 815-R-99-014*), 1999.
37. I. Fabian, G. Gordon, *Inorg. Chem.* 1992, 31, 2144.
38. P. T. Anastas, J. C. Warner, *Green Chemistry: Theory and Practice*, Oxford University Press, 1998.
39. D. Lahaye, J. T. Groves, *J. Inorg. Biochem.* 2007, 101, 1786.
40. A. Q. Lee, B. R. Streit, M. J. Zdilla, M. M. Abu-Omar, J. L. DuBois, *Proc. Nat. Acad. Sci. USA* 2008, 105, 15654.
41. R. G. Kieffer, G. Gordon, *Inorg. Chem.* 1968, 7, 239.
42. N. Jin, M. Ibrahim, T. G. Spiro, J. T. Groves, *J. Am. Chem. Soc.* 2007, 129, 12416.
43. R. H. Holm, J. P. Donahue, *Polyhedron* 1993, 12, 571.
44. H. A. Laitinen, K. W. Boyer, *Anal. Chem.* 1972, 44, 920.
45. N. Jin, J. T. Groves, *J. Am. Chem. Soc.* 1999, 121, 2923.
46. J. T. Groves, J. B. Lee, S. S. Marla, *J. Am. Chem. Soc.* 1997, 119, 6269.
47. *Sampling and Analytical Methods: Chlorine and Chlorine Dioxide in Workplace Atmospheres* (*OSHA method 126SGX*), United States Department of Labor, 2008.
48. a) M. J. Zdilla, A. Q. Lee, M. M. Abu-Omar, *Angew. Chem. Int. Ed.* 2008, 47, 7697; b) M. J. Zdilla, A. Q. Lee, M. M. Abu-Omar, *Inorg. Chem.* 2009, 48, 2260.
49. L. M. Slaughter, J. P. Collman, T. A. Eberspacher, J. I. Brauman, *Inorg. Chem.* 2004, 43, 5198.
50. S. Shahangian, L. P. Hager, *J. Biol. Chem.* 1981, 256, 6034.
51. C. Jakopitsch, H. Spalteholz, P. G. Furtmuller, J. Arnhold, C. Obinger, *J. Inorg. Biochem.* 2008, 102, 293.
52. a) J. T. Groves, S. S. Marla, *J. Am. Chem. Soc.* 1995, 117, 9578; b) S. S. Marla, J. Lee, J. T. Groves, *Proc. Nat. Acad. Sci. USA* 1997, 94, 14243.
53. N. Jin, J. L. Bourassa, S. C. Tizio, J. T. Groves, *Angew. Chem. Int. Ed.* 2000, 39, 3849.
54. G. Peintler, I. Nagypal, I. R. Epstein, *J. Phys. Chem.* 1990, 94, 2954.
55. J. S. Nicoson, D. W. Margerum, *Inorg. Chem.* 2002, 41, 342.
56. H. A. Laitinen, K. W. Boyer, *Anal. Chem.* 1972, 44, 920.
57. *Sampling and Analytical Methods: Chlorine and Chlorine Dioxide in Workplace* Atmospheres (*OSHA method 126SGX*), United States Department of Labor, 2008.

The references cited throughout this application, are incorporated for all purposes apparent herein and in the references themselves as if each reference was fully set forth. For the sake of presentation, specific ones of these references are cited at particular locations herein. A citation of a reference at a particular location indicates a manner(s) in which the teachings of the reference are incorporated. However, a citation of a reference at a particular location does not limit the manner in which all of the teachings of the cited reference are incorporated for all purposes.

It is understood, therefore, that this invention is not limited to the particular embodiments disclosed, but is intended to cover all modifications which are within the spirit and scope of the invention as defined by the appended claims; the above description; and/or shown in the attached drawings.

What is claimed is:

1. A cartridge comprising a housing and at least one of an iron porphyrin catalyst or an iron porphyrazine catalyst in the housing, wherein the cartridge is adapted to allow reactants to contact the at least one of an iron porphyrin catalyst or an iron porphyrazine catalyst, and the cartridge further comprises at least one of the reactants or a source of $ClO_2^-$ in the housing, and the reactants comprise $ClO_2^-$.

2. The cartridge of claim 1, wherein the iron porphyrin catalyst has a structure of formula I:

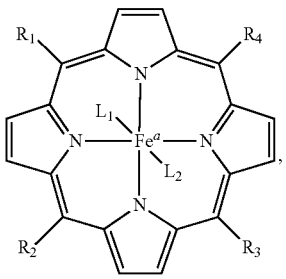

Formula I wherein the a is the oxidation state II, III or IV of the Fe and $R_1$, $R_2$, $R_3$, and $R_4$ are independently selected from the group consisting of TM2PyP, TM4PyP, TDMImP, and TDMBImp, which have a structure of formulas II, III, IV, and V, respectively:

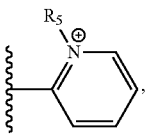

Formula II

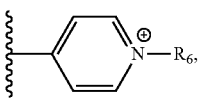

Formula III

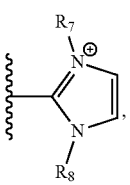

Formula IV

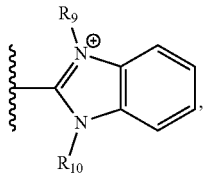

Formula V and at least one of $R_5$, $R_6$, $R_7$, $R_8$, $R_9$, and $R_{10}$ are independently selected from the group consisting of H, methyl, ethyl, propyl, isopropyl, n-butyl, sec-butyl, isobutyl, $CH_2$—$(CH_2)_{n1}$—$CH_3$ where n1=5-20, $CH_2$—$(CH_2)_{n2}$—$CH_2$—X where n2=0-20, —$CH_2(CO)$—$(CH_2)_{n3}$—$CH_2$—X where n3=0-20, —$CH_2$—Ar—X, $(CH_2)_n$—X, $(CH_2)_m$Ar—X, $(CH_2)_m$Ar—Y, $(CH_2)_n$—Y, $CH_2CONH$—Y; $CH_2COO$—Y, $CH_2CO(CH_2)_P$—Y, $(OCH_2CH_2)_m$—Y, $(OCH_2CH_2)_m$—X; $Y_2$—X, $CH_2CH_2OCH_2CH_2OCH_2CH_2OCH_3$, —$CH_2CO_2CH_2CH_3$, alkyl, $CH_2CH_2OCH_3$, $CH_2CH_2OCH_2CH_2OCH_3$, $(CH_2)_n$—X, $(CH_2)_n$—Y, $(CH_2)_n$Ar—X, $(CH_2)_n$Ar—Y, $CH_2CH_2OCH_2CH_2OCH_2CH_2OCH_3$, $CH_2CO_2CH_2CH_3$, $(OCH_2CH_2)_m$—X, $(OCH_2CH_2)_m$—Y, $Y_2$—X, or $Y_2C(Z_1)_3$; where $Z_1$ is $CH_2OCH_2(CH_2)_nX$, $CH_2OCH_2(CH_2)_nY$, or $(CH_2)_nC(O)Y_2C(Z_2)_3$; $Z_2$ is $CH_2OCH_2CH_2C(O)Y_2C(Z_4)_3$; $Z_4$ is $CH_2OCH_2CH_2X$ or $(CH_2)_nC(O)$—$Y_2$—$C(Z_5)_3$; $Z_5$ is $CH_2OCH_2CH_2C(O)Y_2C(Z_6)_3$; $Z_6$ is $CH_2OCH_2CH_2C(O)O(CH_2CH_2O)_mCH_2CH_2O$, $(CH_2)_nOCH_2C(CH_2OH)_3$, $(CH_2)_nOCH_2CH(CH_2OH)_2$, $(CH)_nOCH_2C(CH_2OH)_2(CH_3)$, $(CH_2)_nOCH_2C[CH_2OCH_2C(CH_2OH)_3]_3$, $(CH_2)_nOCH_2C[CH_2OCH_2C(CH_2O[CH_2CH_2O]_mCH_2CH_2OX)_3$, $CH_2CONH$—Y, $CH_2CO$—Y, or $CH_2CO(CH_2)_P$—Y; where Ar is substituted or unsubstituted phenyl, substituted or unsubstituted biphenyl, or substituted or unsubstituted naphthyl and when Ar is the phenyl in —$CH_2$—Ar—X, $(CH_2)_m$Ar—X, or $(CH_2)_m$Ar—Y, the X or Y is attached ortho- meta- or para to the —$CH_2$— attached to pyridoporphyrazine;

n is 1 to 10; m is 1 to 200; p is 1 or 2; X is COOH, COO(alkyl$_1$), $CONH_2$, CONH(alkyl$_1$), CON(alkyl$_1$)$_2$, CO(CH$_2$)$_P$alkyl$_1$, OPO$_3$H$_2$, PO$_3$H$_2$, SO$_3$H, NH$_2$, N(alkyl$_1$)$_2$, or N(alkyl$_1$)$_3$+, where alkyl$_1$ is methyl, ethyl, propyl, butyl, pentyl, hexyl, heptyl, or octyl; Y is OH, (O—CH$_2$CH$_2$)$_m$—W$_1$, or (CH$_2$CH$_2$)$_m$—W$_2$, where W$_1$ is OH or (O—(CH$_2$CH$_2$)$_m$OH), and W$_2$ is O-alkyl; and $Y_2$ is —(CH$_2$)$_n$O—, —(CH$_2$)$_n$NH—, —(CH)$_n$S—; CH$_2$CONH—, CH$_2$COO—, or CH$_2$CO(CH$_2$)$_P$—; and $L_1$ and $L_2$ are, independently absent, halide, oxo, aquo, hydroxo, CN, OPO$_3$H, or alcohol.

3. The cartridge of claim 2, wherein the alkyl is selected from straight-chain or branched-chain alkyl radicals containing from 1 to 22 carbon atoms, methyl, ethyl, n-propyl, isopropyl, n-butyl, isobutyl, sec-butyl, tert-butyl, pentyl, iso-amyl, hexyl, octyl, nonyl, decyl, dodecyl, tetradecyl, hexadecyl, octadecyl, and eicosyl.

4. The cartridge of claim 2, wherein $R_1$, $R_2$, $R_3$, and $R_4$ are TDMBImp.

5. The cartridge of claim 2, wherein $R_1$, $R_2$, $R_3$, and $R_4$ are TM2PyP or $R_1$, $R_2$, $R_3$ and $R_4$ are TM4PyP.

6. The cartridge of claim 1, wherein the iron porphyrazine catalyst has a structure of formula VI:

Formula VI

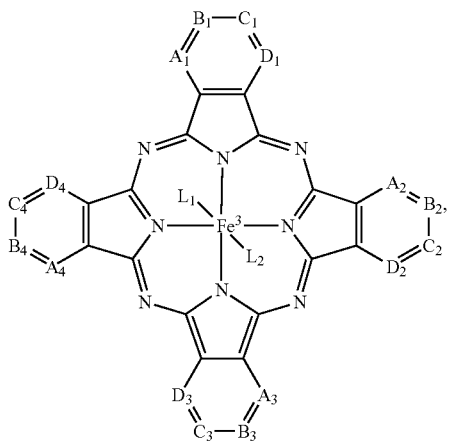

wherein a is the oxidation state II, III or IV of the Fe and each of $A_1$, $A_2$, $A_3$, $A_4$, $B_1$, $B_2$, $B_3$, $B_4$, $C_1$, $C_2$, $C_3$, $C_4$, $D_1$, $D_2$, $D_3$, and $D_4$ are independently selected from $N^+$—$R_n$, N, C—H, C—X, and C—$R_n$;

when $N^+$—$R_n$ is selected, only one in each set of $A_1$, $B_1$, $C_1$, and $D_1$; $A_2$, $B_2$, $C_2$, and $D_2$; $A_3$, $B_3$, $C_3$, and $D_3$; or $A_4$, $B_4$, $C_4$, and $D_4$ is $N^+$—$R_n$;

when N is selected, only one in each set of $A_1$, $B_1$, $C_1$, and $D_1$; $A_2$, $B_2$, $C_2$, and $D_2$; $A_3$, $B_3$, $C_3$, and $D_3$; or $A_4$, $B_4$, $C_4$, and $D_4$ is N;

each $R_n$ is independently selected from the group consisting of H, methyl, ethyl, propyl, isopropyl, n-butyl, sec-butyl, isobutyl, $CH_2$—$(CH_2)_{n1}$—$CH_3$ where n1=5-20, $CH_2$—$(CH_2)_{n2}$—$CH_2$—X where n2=0-20, $CH_2$—(CO)—$(CH_2)_{n3}$—$CH_2$—X where n3=0-20, $CH_2$—Ar—X, $(CH_2)_n$—X; $(CH_2)_m$Ar—X, $(CH_2)_m$Ar—Y, $(CH_2)_n$—Y, $CH_2$CONH—Y; $CH_2$COO—Y, $CH_2$CO—Y, $CH_2$CO$(CH_2)_p$—Y, $(OCH_2CH_2)_m$—Y, $(OCH_2CH_2)_m$—X, $Y_2$—X, $CH_2CH_2OCH_2CH_2OCH_2CH_2OCH_3$, $CH_2CO_2CH_2CH_3$, $CH_2CH_2OCH_3$, $CH_2CH_2OCH_2CH_2OCH_3$, $(CH_2)_n$—Y, $(CH_2)_n$Ar—X, $(CH_2)_n$Ar—Y, and $Y_2C(Z_1)_3$; $Z_1$ is $CH_2OCH_2(CH_2)_nX$, $CH_2OCH_2(CH_2)_nY$, or $(CH_2)_nC(O)Y_2C(Z_2)_3$; $Z_2$ is $CH_2OCH_2CH_2C(O)Y_2C(Z_3)_3$; $Z_3$ is $CH_2OCH_2CH_2X$ or $(CH_2)_nC(O)$—$Y_2$—$C(Z_4)_3$; $Z_4$ is $CH_2OCH_2CH_2C(O)Y_2C(Z_5)_3$; and $Z_5$ is $CH_2OCH_2CH_2C(O)O(CH_2CH_2O)_mCH_2CH_2O$, $(CH_2)_nOCH_2C(CH_2OH)_3$, $(CH_2)_nOCH_2CH(CH_2OH)_2$, $(CH_2)_nOCH_2C(CH_2OH)_2(CH_3)$, $(CH_2)_nOCH_2C[CH_2OCH_2C(CH_2OH)_3]_3$, $(CH_2)_nOCH_2C[CH_2OCH_2C(CH_2O[CH_2CH_2O]_mCH_2CH_2OX)_3$, $CH_2CONH$—Y, $CH_2CO$—Y, or $CH_2CO(CH_2)_p$—Y; where Ar is substituted or unsubstituted phenyl, substituted or unsubstituted biphenyl, or substituted or unsubstituted naphthyl and when Ar is the phenyl in —$CH_2$—Ar—X, $(CH_2)_m$Ar—X, or $(CH_2)_m$Ar—Y, the X or Y is attached ortho- meta- or para to the —$CH_2$— attached to pyridoporphyrazine;

n is 1 to 10; m is 1 to 200; p is 1 or 2; X is COOH, COO(alkyl$_1$), CONH$_2$, CONH(alkyl$_1$), CON(alkyl$_1$)$_2$, CO(CH$_2$)$_p$alkyl$_1$, OPO$_3$H$_2$, PO$_3$H$_2$, SO$_3$H, NH$_2$, N(alkyl$_1$)$_2$, or N(alkyl$_1$)$_3$+, where alkyl$_1$ is methyl, ethyl, propyl, butyl, pentyl, hexyl, heptyl, or octyl; Y is OH, (O—$CH_2CH_2)_m$—$W_1$, or $(CH_2CH_2)_m$—$W_2$; $W_1$ is OH or (O—$(CH_2CH_2)_m$OH); $W_2$ is O-alkyl; and $Y_2$ is —$(CH_2)_nO$—, —$(CH_2)_nNH$—, —$(CH_2)_nS$—; $CH_2CONH$—, $CH_2COO$—, or $CH_2CO(CH_2)_p$—; and $L_1$ and $L_2$ are independently absent, halide, oxo, aquo, hydroxo, CN, OPO$_3$H, or alcohol.

7. The cartridge of claim 6, wherein in the O-alkyl the alkyl is selected from straight-chain or branched-chain alkyl radicals containing from 1 to 22 carbon atoms, methyl, ethyl, n-propyl, isopropyl, n-butyl, isobutyl, sec-butyl, tert-butyl, pentyl, iso-amyl, hexyl, octyl, nonyl, decyl, dodecyl, tetradecyl, hexadecyl, octadecyl, and eicosyl.

8. The cartridge of claim 1, wherein the cartridge comprises the reactants, and the reactants.

9. The cartridge of claim 8, wherein the $ClO_2^-$ is in the form of at least one substance selected from the group consisting of chlorite salts.

10. The cartridge of claim 8, wherein the $ClO_2^-$ is in the form of at least one substance selected from the group consisting of sodium chlorite, potassium chlorite, calcium chlorite and magnesium chlorite.

11. The cartridge of claim 8, wherein the $ClO_2^-$ is mixed with a solid filler.

12. The cartridge of claim 8, wherein the $ClO_2^-$ is adsorbed on at least one substance selected from the group consisting of clay, silica, alumina and organic polymers.

13. The cartridge of claim 1, wherein at least one of the iron porphyrin catalyst or the iron porphyrazine catalyst is adsorbed on a solid support.

14. The cartridge of claim 13, wherein the solid support includes a substance selected from the group consisting of clay, silica, alumina, glass beads, functionalized polystyrene or organic polymers.

15. The cartridge of claim 1 comprising the source of $ClO_2^-$, wherein the at least one of the iron porphyrin catalyst or the iron porphyrazine catalyst and the source of $ClO_2^-$ are separated by an interface.

16. The cartridge of claim 15, wherein the interface is a solid material configured to allow mixing of the at least one of the iron porphyrin catalyst or the iron porphyrazine catalyst with the source of $ClO_2$ upon mechanical disruption of the interface.

17. The cartridge of claim 16, wherein the mechanical disruption includes breaking of the solid material.

18. The cartridge of claim 16, wherein the mechanical disruption includes dissolution of the solid material.

19. The cartridge of claim 1 comprising the source of $ClO_2^-$, wherein the housing includes a first compartment and a second compartment, and the at least one of an iron porphyrin catalyst or an iron porphyrazine catalyst is in the first compartment and the source of $ClO_2^-$ is in the second compartment.

20. The cartridge of claim 19, wherein at least one of the iron porphyrin catalyst or the iron porphyrazine catalyst is adsorbed on a solid support.

21. The cartridge of claim 20, wherein the solid support includes a substance selected from the group consisting of clay, silica, alumina, glass beads, functionalized polystyrene and organic polymers.

22. The cartridge of claim 16, wherein the source of $ClO_2^-$ is a chlorite salt.

* * * * *

UNITED STATES PATENT AND TRADEMARK OFFICE
CERTIFICATE OF CORRECTION

PATENT NO. : 11,242,248 B2
APPLICATION NO. : 16/400277
DATED : February 8, 2022
INVENTOR(S) : John T. Groves and Roy Xiao It is certified that error appears in the above-identified patent and that said Letters Patent is hereby corrected as shown below:

In the Claims

In Claim 2, at Column 46, Lines 29 and 30, delete "$CH_2OCH_2CH_2C(O)O(CH_2CH_2O)_mCH_2CH_2O$" and insert --$CH_2OCH_2CH_2C(O)O(CH_2CH_2O)_mCH_2CH_2O^-$-- therefor.

In Claim 6, at Column 47, Line 11, in Formula VI, delete "$Fe^3$" and insert --$Fe^a$-- therefor.

In Claim 6, at Column 47, Line 31, after the word "each", delete "R" and insert --$R_n$-- therefor.

In Claim 6, at Column 47, Line 44, delete "$(CH_2),C(O)Y_2C(Z_2)_3$" and insert --$(CH_2)_nC(O)Y_2C(Z_2)_3$-- therefor.

In Claim 6, at Column 47, Lines 47 and 48, delete "$CH_2OCH_2CH_2C(O)O(CH_2CH_2O)_mCH_2CH_2O$" and insert --$CH_2OCH_2CH_2C(O)O(CH_2CH_2O)_mCH_2CH_2O^-$-- therefor.

In Claim 8, at Column 48, Line 15, after the first instance of the word "reactants", delete ", and the reactants".

Signed and Sealed this
Twentieth Day of December, 2022

*Katherine Kelly Vidal*
Katherine Kelly Vidal
*Director of the United States Patent and Trademark Office*